(12) United States Patent
Svanborg et al.

(10) Patent No.: US 9,085,643 B2
(45) Date of Patent: Jul. 21, 2015

(54) BIOLOGICALLY ACTIVE COMPLEX AND ITS PREPARATION

(75) Inventors: Catharina Svanborg, Lund (SE); Kenneth Hun Mok, Dublin (IE); Maria Trulsson, Lund (SE); Ann-Kristin Mossberg, Loddekopinge (SE); Petter Storm, Lund (SE); Chin Shing Ho, Lund (SE)

(73) Assignee: HAMLET PHARMA AB (SE)

( * ) Notice: Subject to any disclaimer, the term of this patent is extended or adjusted under 35 U.S.C. 154(b) by 0 days.

(21) Appl. No.: 13/988,878

(22) PCT Filed: Nov. 24, 2011

(86) PCT No.: PCT/GB2011/052310
§ 371 (c)(1),
(2), (4) Date: Nov. 4, 2013

(87) PCT Pub. No.: WO2012/069836
PCT Pub. Date: May 31, 2012

(65) Prior Publication Data
US 2014/0051636 A1    Feb. 20, 2014

(30) Foreign Application Priority Data

Nov. 24, 2010 (GB) .................................. 1019936.2
Nov. 24, 2010 (GB) .................................. 1019937.0

(51) Int. Cl.
| | | |
|---|---|---|
| A61K 38/16 | (2006.01) | |
| C07K 14/00 | (2006.01) | |
| A61P 35/00 | (2006.01) | |
| C07K 14/76 | (2006.01) | |
| A61K 31/201 | (2006.01) | |
| C12Q 1/18 | (2006.01) | |
| G01N 33/50 | (2006.01) | |
| G01N 33/68 | (2006.01) | |

(52) U.S. Cl.
CPC ............... *C07K 14/76* (2013.01); *A61K 31/201* (2013.01); *A61K 38/16* (2013.01); *C12Q 1/18* (2013.01); *G01N 33/5011* (2013.01); *G01N 33/6872* (2013.01)

(58) Field of Classification Search
CPC ....... A61K 31/201; A61K 38/16; C12Q 1/18; G01N 33/5011; G01N 33/6872; C07K 14/76
See application file for complete search history.

(56) References Cited

U.S. PATENT DOCUMENTS

| | | | | |
|---|---|---|---|---|
| 7,053,185 B1 * | 5/2006 | Svanborg et al. | ............. | 530/366 |
| 2003/0055105 A1 | 3/2003 | Ito et al. | | |
| 2012/0028883 A1 | 2/2012 | Svanborg et al. | | |

FOREIGN PATENT DOCUMENTS

| | | | |
|---|---|---|---|
| WO | 99/26979 A1 | 6/1999 | |
| WO | 99/27967 A1 | 6/1999 | |
| WO | 01/17524 A1 | 3/2001 | |
| WO | 03/074547 A2 | 9/2003 | |
| WO | WO 2007/049905 A1 * | 5/2007 | ............... C07K 7/06 |
| WO | 2008/058547 A2 | 5/2008 | |
| WO | 2008/138348 A1 | 11/2008 | |
| WO | 2010/079362 A1 | 7/2010 | |
| WO | 2010/131237 A1 | 11/2010 | |
| WO | 2012/069836 A2 | 5/2012 | |

OTHER PUBLICATIONS

Water, from http://www.biology-online.org/dictionary/Water, pp. 1-3, accessed Apr. 24, 2014.*
Glycerol, from http://www.naturalwellbeing.com/learning-center/Glycerol, pp. 1-3, accessed Apr. 24, 2014.*
Lipid Metabolism, from http://oregonstate.edu/dept/biochem/hhmi/hhmiclasses/biochem/lectnoteskga/lecturenotes0 . . . , pages 1-5, accessed Apr. 24, 2014.*
Glucagon-like peptide-1-Amphiuma tridactylum, from http://www.ncbi.nlm.nih.gov/protein/AAB37528.1, p. 1, accessed Sep. 29, 2014.*
Ethanol Injection, from http://www.hopkinsmedicine.org/se/util/display_mod.cfm?MODULE=/se-server/mod/mod . . . , page 1, accessed Sep. 29, 2014.*
Oleic acid, from http://pubchem.ncbi.nlm.nih.gov/summary/summary.cgi?cid=445639, p. 1, accessed Sep. 30, 2014.*
Abbott et al., "Microbial Transformation of A23187, a Divalent Cation Ionophore Antibiotic", Antimicrobial Agents and Chemotherapy, 1979, pp. 808-812, vol. 16, No. 6.
Abramoff et al., "Image Processing with ImageJ", Biophotonics International, Jul. 2004, 7 pgs.
Aits et al., "HAMLET (human α-lactalbumin made lethal to tumor cells) triggers autophagic tumor cell death", Int. J. Cancer, 2009, pp. 1008-1019, vol. 124.
Anderson et al., "Functional Identification of Calcium Binding Residues in Bovine α-Lactalbumin", Biochemistry, 1997, pp. 11648-11654, vol. 36, No. 39.
Arcangeli et al., "Targeting Ion Channels in Cancer: A Novel Frontier in Antineoplastic Therapy", Current Medicinal Chemistry, 2009, pp. 66-93, vol. 16, No. 1.

(Continued)

*Primary Examiner* — Julie Ha
*Assistant Examiner* — Li Ni Komatsu

(57) ABSTRACT

A biologically active complex comprising either a polypeptide having the sequence of a variant of a naturally occurring protein, wherein said polypeptide is at least partially unfolded as compared to the said naturally occurring protein; or a peptide of up to 50 amino acids, for instance a fragment of the naturally occurring protein or a variant thereof; and a pharmaceutically acceptable salt of a fatty acid or lipid. The complexes of the invention demonstrate a novel mode of action, that gives rise to opportunities for the development of further active agents and screening methods.

15 Claims, 30 Drawing Sheets

(56) References Cited

OTHER PUBLICATIONS

Chua et al., "A novel normalization method for effective removal of systematic variation in microarray data", Nucleic Acids Research, 2006, pp. e38, 7 pgs., vol. 34, No. 5.
Cobb, "MAP kinase pathways", Progress in Biophysics & Molecular Biology, 1999, pp. 479-500, vol. 71.
Correa-Meyer et al., "Cyclic stretch activates ERK1/2 via G proteins and EGFR in alveolar epithelial cells", Am. J. Physiol. Lung Cell Mol. Physiol., 2002, pp. L883-L891, vol. 282.
Cuenda et al., "p38 MAP-Kinases pathway regulation, function and role in human diseases", Biochimica et Biophysica Acta, 2007, pp. 1358-1375, vol. 1773.
Dennis et al., "DAVID: Database for Annotation, Visualization, and Integrated Discovery", Genome Biology, 2003, P3, 19 pgs., vol. 4, No. 5.
Fabian et al., "A small molecule—kinase interaction map for clinical kinase inhibitors", Nature Biotechnology, 2005, pp. 329-336, vol. 23, No. 3.
Fast et al., "Stability of HAMLET—A kinetically trapped α-lactalbumin oleic acid complex", Protein Science, 2005, pp. 329-340, vol. 14, No. 2.
Fischer et al., "Human α-Lactalbumin Made Lethal to Tumor Cells (HAMLET) Kills Human Glioblastoma Cells in Brain Xenografts by an Apoptosis-Like Mechanism and Prolongs Survival", Cancer Research, 2004, pp. 2105-2112, vol. 64.
GB Search Report from related Application No. GB1019937.0, dated Mar. 24, 2011, 5 pgs.
Gustafsson et al., "Treatment of Skin Papillomas with Topical α-Lactalbumin—Oleic Acid", The New England Journal of Medicine, 2004, pp. 2663-2672, vol. 350, No. 26.
Hakansson et al., "Apoptosis induced by a human milk protein", PNAS, 1995, pp. 8064-8068, vol. 92.
Huang et al., "Cell tension, matrix mechanics, and cancer development", Cancer Cell, 2005, pp. 175-176, vol. 8.
Huff et al., "Pathological and functional amyloid formation orchestrated by the secretory pathway", Current Opinion in Structural Biology, 2003, pp. 674-682, vol. 13.
International Search Report and Written Opinion from related application, PCT/GB2011/052310, dated Jun. 26, 2012, 13 pgs.
International Search Report and Written Opinion from related application, PCT/GB2010/050024, dated Apr. 7, 2010, 13 pgs.
Irizarry et al., "Exploration, normalization, and summaries of high density oligonucleotide array probe level data", Biostatistics, 2003, pp. 249-264, vol. 4, No. 2.
Karpman et al., "Apoptosis of Renal Cortical Cells in the Hemolytic-Uremic Syndrome: in Vivo and in Vitro Studies", Infection and Immunity, 1998, pp. 636-644, vol. 66, No. 2.
Kuwajima, "The molten globule state of α-lactalbumin", Faseb J., 1996, pp. 102-109, vol. 1.
Mok et al., "HAMLET, protein folding, and tumor cell death", Biochemical and Biophysical Research Communications, 2007, pp. 1-7, vol. 354, No. 1.

Mossberg et al., "Bladder cancers respond to intravesical instillation of HAMLET (human α-lactalbumin made lethal to tumor cells)", International Journal of Cancer, 2007, pp. 1352-1359, vol. 121.
Mossberg et al., "HAMLET Treatment Delays Bladder Cancer Development", The Journal of Urology, 2010, pp. 1590-1597, vol. 183.
Owens et al., "Differential regulation of MAP kinase signalling by dual-specificity protein phosphatases", Oncogene, 2007, pp. 3203-3213, vol. 26.
Peng et al., "Local Structural Preferences in the α-Lactalbumin Molten Globule", Biochemistry, 1995, pp. 3248-3252, vol. 34.
Pettersson et al., "α-Lactalbumin species variation, HAMLET formation, and tumor cell death", Biochemical and Biophysical Research Communications, 2006, pp. 260-270, vol. 345, No. 1.
Pfeil, "Is thermally denatured protein unfolded? The example of α-lactalbumin", Biochimica et Biophysica Acta, 1987, pp. 114-116, vol. 911.
Rammer et al., "BAMLET Activates a Lysosomal Cell Death Program in Cancer Cells", Molecular Cancer Therapeutics, 2010, vol. 9, No. 1, Abstract Only.
Schulman et al., "Different Subdomains are Most Protected From Hydrogen Exchange in the Molten Globule and Native States of Human α-Lactalbumin", Journal of Molecular Biology, 1995, pp. 651-657, vol. 253, No. 5.
Svanborg et al., "HAMLET Kills Tumor Cells by an Apoptosis-Like Mechanism—Cellular, Molecular, and Therapeutic Aspects", Advances in Cancer Research, 2003, pp. 1-29, vol. 88.
Svensson et al., "Molecular Characterization of α-Lactalbumin Folding Variants That Induce Apoptosis in Tumor Cells", The Journal of Biological Chemistry, 1999, pp. 6388-6396, vol. 274, No. 10.
Svensson et al., "Conversion of α-lactalbumin to a protein inducing apoptosis", PNAS, 2000, pp. 4221-4226, vol. 97, No. 8.
Vukojevic et al., "Lipoprotein Complex of Equine Lysozyme with Oleic Acid (ELOA) Interactions with the Plasma Membrane of Live Cells", Langmuir, 2010, pp. 14782-14787, vol. 26, No. 18.
Wang et al., "Stress-Induced Phosphorylation and Activation of the Transcription Factor CHOP (GADD153) by p38 MAP Kinase", Science, 1996, pp. 1347-1349, vol. 272, No. 5266.
Wolf et al., "Multi-step pericellular proteolysis controls the transition from individual to collective cancer cell invasion", Nature Cell Biology, 2007, pp. 893-904, vol. 9, and Supplementary Information.
Xia et al., "Opposing Effects of ERK and JNK-p38 MAP Kinases on Apoptosis", Science, 1995, pp. 1326-1331, vol. 270, No. 5240.
Yoshida et al., "XBP1 mRNA is Induced by ATF6 and Spliced by IRE1 in Response to ER Stress to Produce a Highly Active Transcription Factor", Cell, 2001, pp. 881-891, vol. 107.
Notice of Allowance regarding related U.S. Appl. No. 13/143,785, dated Apr. 2, 2014, 16 pgs.
Non-Final Office Action from related U.S. Appl. No. 13/143,785, dated Sep. 16, 2013, 10 pgs.

* cited by examiner

| Cell type | EGTA | Inhibitor | % responding cells | |
|---|---|---|---|---|
| | | | Early Peak | Late Peak |
| Carcinoma | - | None | 57 | 100 |
| | - | Amiloride | 100 | 89 |
| | - | BaCl₂ | 0 | 25 |
| | - | GdCl₃ | 0 | 100 |
| | + | None | 60 | 32 |
| | + | Amiloride | 0 | 0 |
| | + | BaCl₂ | 0 | 0 |
| | + | GdCl₃ | 0 | 0 |
| | | | | |
| Healthy, differentiated | - | None | 100 | 0 |
| | - | Amiloride | 60 | 40 |
| | - | BaCl₂ | 25 | 75 |
| | - | GdCl₃ | 0 | 0 |
| | + | None | 100 | 22 |
| | + | Amiloride | 0 | 0 |
| | + | BaCl₂ | 0 | 0 |
| | + | GdCl₃ | 86 | 0 |

Differentially expressed genes in lthe p38 signalling pathway in HAMLET-treated A498 Kidney Carcinoma cells.

A

B

A) Global transcriptional changes

B) Healthy kidney cells

C) Carcinoma kidney cells

Conversion chromatography:

Designated peptides are highlighted in bold

Alpha 1

Alpha 2

Beta

BIOLOGICALLY ACTIVE COMPLEX AND ITS PREPARATION

CROSS-REFERENCE TO RELATED APPLICATIONS

This application is a U.S. National Stage Application of PCT International Application No. PCT/GB2011/052310, filed Nov. 24, 2011 and claims priority to GB Application No. 1019937.0, filed Nov. 24, 2010, and GB Application No. 1019936.2, filed Nov. 24, 2010, the disclosure of each is hereby incorporated by reference in its entirety.

FIELD OF THE INVENTION

The present invention relates to biologically active complexes that have therapeutic activity in particular in the treatment of tumours or as antibacterial or antiviral agents. The present invention further relates to methods of treating tumors and cancers, in particular to methods for selectively targeting tumor cells in preference to healthy cells, as well as to compositions and reagents for use in these methods. In addition, the invention relates to screening methods for identifying suitable reagents for use in the methods.

BACKGROUND OF THE INVENTION

There has been much interest of late in the production of complexes that involve partially unfolded proteins and lipids. These proteins may have drastically different properties and particularly biological properties than the corresponding proteins in a fully folded state. The gain of new, beneficial function upon partial protein unfolding and fatty acid binding is a remarkable phenomenon, and may reflect a significant generic route of functional diversification of proteins via varying their conformational states and associated ligands. Thus, in addition to alternative splicing of mRNA transcripts, post-translational modifications and changes in tertiary structure of specific domains, partial unfolding of a previously native protein is becoming recognized as a mechanism to generate functional diversity. This may be due to a cellular response to unfolded proteins and to the lipid cofactor, which defines their altered properties. However, this response may be different in for instance tumour cells, which means that they may give rise to therapeutic potential. In order to form stable moieties, the unfolded proteins are frequently modified in some way, and in particular may be bound to cofactors such as fatty acid cofactors. The complexes formed in this way may be stable and give rise to therapeutic options.

HAMLET (human alpha-lactalbumin made lethal to tumor cells) is one such example of a new family of tumoricidal molecules, with remarkable properties. Formed from partially unfolded α-lactalbumin and with oleic acid as an integral constituent (Svensson et al., 2000 PNAS 97: 4221-4226), HAMLET was discovered by serendipity when studying the ability of human milk to prevent bacteria from binding to cells (Hakansson et al., 1995 Proc. Natl. Acad. Sci. USA 92: 8064-8068). Early in vitro experiments showed that HAMLET displays broad anti-tumor activity with a high degree of tumor selectivity and subsequent therapeutic studies have confirmed HAMLET's tumoricidal activity and relative selectivity for tumor tissue in vivo. In a placebo controlled clinical study, topical HAMLET administration removed or reduced the size of skin papillomas (Gustafsson et al., 2004 New England Journal of Medicine 350: 2663-2672) and in patients with bladder cancer, local instillations of HAMLET caused rapid death of tumor cells but not of healthy tissue surrounding the tumor (Mossberg et al., 2007 Int. J. Cancer: 121: 1352-1359). Therapeutic efficacy of HAMLET in bladder cancer was recently demonstrated in a murine bladder cancer model (Mossberg et al., 2010 The Journal of Urology 183: 1590-1597) and HAMLET treatment delayed tumor progression and led to increased survival in a rat glioblastoma xenograft model without evidence of cell death in healthy brain tissue (Fischer et al., 2004 Cancer Research 64: 2105-2112). HAMLET thus appears to identify death pathways that are conserved in tumor cells, thereby distinguishing them from healthy, differentiated cells.

Complexes using equine lysozyme and oleic acid have also been found to produce cell death (Vukojevic et al. Langmuir, 2010, 26(18) 14782-14787), suggesting that different, unfolded proteins can become cytotoxic when coupled to a suitable cofactor.

Ion channels are membrane proteins that sense alterations in membrane tension or cellular environment, and their activation has been proposed to catalyze several signaling cascades, including ER stress, p38 MAP kinases, small GTPases, PI3K/Akt and NFkB as well as $Ca^{2+}$ dependent pathways, mainly in sensory cells or muscle cells involved in mechanical responses.

Channels are present in most cell types, including bacteria, however and recently, ion channel perturbations have been proposed to promote malignant transformation, tumorigenesis and metastasis (see for example Huang, S., and Ingber, D. E. (2005). Cancer Cell 8, 175-176; Wolf, K et al., (2007). Nat Cell Biol 9, 893-904, and Arcangeli, A et al. (2009). Curr Med Chem 16, 66-93) suggesting immediate relevance of such channels for cancer cell homeostasis.

Specifically, the applicants have identified one example of a molecule that acts as an ion channel activator with tumor specificity and propose that the broad death response of tumor cells and certain bacteria to this and other agonists with similar target specificity involves the perturbation of ion channels, which are conserved throughout evolution. The de-differentiation of tumor cells may thus involve the reversion to a more "primitive" ion channel repertoire, which may be targeted by such agonists. This tumor-selective death through ion channel perturbation is particularly relevant, especially in view of the molecules already documented protective effects against tumors in patients and animal models.

The applicants investigated the activation of ion sensitive and if signaling triggered by such channels might distinguish the death response of tumor cells from the survival response of healthy, differentiated cells. Rapid $Na^+$ and $K^+$ fluxes followed by mobilization from of intracellular $Ca^{2+}$ stores was detected in carcinoma cells.

Inhibition of cell death by Amiloride and $BaCl_2$, which block $Na^+$ and $K^+$ fluxes, suggested that death is triggered through the combined activation of mechanosensitive channels and potassium channels and inhibition of ER stress induction and the p38-dependent death response suggested that ion fluxes directly activate downstream signaling pathways that execute carcinoma cell death. Healthy, differentiated cells, in contrast, showed a weak and transient $Ca^{2+}$ response under similar treatment and but no p38 activation and instead, an innate immune response accompanied their survival. It is possible that tumor selectivity in vivo may thus rely on ion channel perturbations and a p38 MAPK death response, accompanied by a beneficial innate immune response in surrounding tissues.

Defective ion channel signaling deregulates mechanisms of cell-cycle control, DNA-damage repair, apoptosis, adhesion and migration (Huang and Ingber, 2005 Cancer Cell 8, 175-176; Wolf et al., 2007 Nat Cell Biol 9, 893-904). The relationship of ion channel function to cancer has therefore received increasing attention, and ion channels are becoming established as modulators of signals that promote oncogenic transformation. Understanding of ion channel aberrations in cancer progression is therefore essential and controlling their function may constitute an important new approach to cancer therapy. Targeting of ion channels in cancer cells has been proposed as a future therapeutic option (Arcangeli et al., 2009, Curr. Med Chem 16, 66-93), as has the control of mechanosensitive- and other ion channels, which are overexpressed in carcinoma cells. Despite this proposed usefulness, the therapeutic potential of ion channel modulators remains underexploited, due, in part, to side effects reflecting lack of tumor specificity.

The applicants have now identified substances with ion channel activator activity with tumor specificity and propose that the broad death response of tumor cells and certain bacteria can involve the perturbation of ion channels, which are conserved throughout evolution. The de-differentiation of tumor cells may thus involve the reversion to a more "primitive" ion channel repertoire that is targeted by these substances.

While oncogenic transformation and cancer cell function require ion channel support, ion channel variability and complexity is considerable. Ion channel-encoding genes are frequently over-expressed in human cancers, due to gene amplifications, epigenetic regulation or splice variants of channel encoding genes but except for KCNRG, encoding a $K^+$ channel-regulating protein with tumor suppressor properties (ref), tumor-specific mutations in ion channel genes have not been reported. In addition, though most human cancer cells show altered $Ca^{2+}$ wave dynamics, cancer-specific alterations in the "spatio-temporal nature" of $Ca^{2+}$ waves or ion channel expression profiles have largely not been identified (Arcangeli et al., 2009). In specific cell types, siRNA mediated inhibition of individual ion channels has been found efficient, but due to the complexity, knockdown of individual channels is often insufficient to obtain loss of function and to reproduce a phenotype relevant for cancer. The use of pharmacologic channel inhibitors therefore remains crucial for defining the general involvement of different functional classes of ion channels, even though each inhibition does not fully define a specific channel type.

Within these technical limitations, our results show that it is possible to perturb tumor cell membranes, leading to ion fluxes, depolarization and the opening of ion channels in such a manner as to discriminate tumor cells from healthy, differentiated cells. Resulting tumor cell death and morphological changes were shown to be ion channel-dependent, using pharmacological inhibitors and a link between ion channel activation and cell death was suggested by genome wide transcriptomic analysis, showing that channel blockade reduced the number of differentially expressed genes in treated carcinoma cells from about 400 to 40. Transcriptional regulation of the top scoring ER stress, p38, and Ras pathways was inhibited by the channel blockers, as was the phosphorylation of corresponding proteins and inhibition of ion channel activation prevented carcinoma and lymphoma cell death.

Our recent studies in artificial vesicles and tumor cell membrane models suggested that mechanosensitive channels are opened by treatment, as well. Mechanosensitive channels are gated by lipid bilayer deformation forces arising from local or global assymetries in transbilayer pressure or in bilayer curvature. Fluorescence imaging showed that an accumulation of the administered substance in receptor-free phospholipid membranes and perturbs their structure by elongation. Similar results were obtained with plasma membrane vesicles from tumor cells, which formed tube-like membrane invaginations after substance exposure. Furthermore, the applicants have found during some treatments, transient pores form in artificial lipid bilayers at physiological pH, possibly explaining the observed membrane leakage. Thus, in addition to ion channel activation, direct permeabilisation of carcinoma cell membranes might activate cell death.

The signaling profile in carcinoma cells was consistent with patterns previously observed after physiological activation of mechanical, stretch-induced channels in a variety of cell types. Mechanical membrane perturbations have been shown to perturb ERK1/2 via G proteins and especially p38 signaling (Correa-Meyer et al., 2002, Am. J. Physiol. Lung Cell Mol. Physiol. 282: L883-L891). JNK and p38 are also key mediators of signals stimulated by various stresses and are mainly responsible for responses such as stress-dependent apoptosis and inflammatory responses. HAMLET shifted the MAPK signaling profile of tumor cells from the ERK1/2 to the p38 pathway, and thus from proliferation to death. In mammals, MAPKs are divided into three major groups, ERKs, JNKs/stress-activated protein kinases, and p38, based on their degree of homology, biological activities, and phosphorylation motifs (Cobb, 1999 Progress in Biophysics & Molecular Biology 71, 479-500). MKK3 and MKK6 activate p38 MAP kinases by phosphorylation at Thr180 and Tyr182 and activated p38 MAP kinases phosphorylate and activate MAPKAP kinase 2 and phosphorylate the transcription factors ATF-2, Max and MEF2. Subsequent phosphorylation of p53 and CHOP, among other targets, leads to the activation of cell death mechanisms, including mitochondrial permeabilisation, caspase activation and DNA fragmentation, which has been shown to occur in some treated carcinoma cells. In addition, Hsp27 phosphorylation mediates cytoskeletal rearrangements, potentially explaining the change in morphology that we observed in carcinoma cells exposed to some treatment.

Changes in cytoplasmic $Ca^{2+}$ concentrations may compromise the ability of the ER to correctly fold proteins, thereby eliciting the unfolded protein response. HAMLET activated all three main branches of the unfolded protein response and in addition a number of ER stress related genes were transcriptionally upregulated, including ATF4 and BIP. The activation of eIF2α in response to HAMLET may act as an "emergency break" to prevent further protein synthesis when the folding capacity of the ER is compromised. HAMLET treatment also triggered ATF6 cleavage and an increase in spliced XBP1, both acting to induce the transcription of a diverse set of chaperones and other ER-stress regulated genes, to augment the ER protein folding capacity. The inhibition by amiloride of the transcriptomic ER stress response and of eIF2α phosphorylation indicates that ion channel activation is an essential trigger of the ER stress response to HAMLET. In addition, the experiments reported hereinafter suggest that HAMLET interacts directly either with ER chaperones or the ER stress sensors as HAMLET has been shown to interact directly with proteasomes, which play a crucial role in ER stress and the unfolded protein response. HAMLET may also indirectly perturb the protein folding capability of carcinoma cells by decreasing ATP levels and by causing mitochondrial damage and permeabilization.

In healthy differentiated cells, HAMLET targeted innate immune signaling pathways involved in innate immunity and transiently suppressed p38 signaling. Although this immune response was low or absent in tumor cells, similar immune response pathways were strongly regulated in carcinoma cells under p38-specific inhibition, implying that these are not completely separate cellular response strategies. The mobilization intracellular Ca$^{2+}$ by HAMLET in both carcinoma cells and healthy cells might indicate that this activation mechanism is shared, though of different magnitude. But the subsequent ion channel response was mainly observed in the carcinoma cells, which, however, suggests that this is the critical step to trigger cell death, a hypothesis also supported by the rescue effects of the ion channel blockers. This innate immune response would ideally serve to activate macrophages and other cells that scavenge and digest the remnants of apoptotic cells at sites of tissue damage and provide a suitable immune environment for cancer cell removal.

We speculate that the ability to selectively kill a broad range of tumor cells combined with the innate immune response of healthy differentiated cells gives rise to low toxicity in clinical studies as well as other beneficial effects. The p38 effector response in tumor cells accompanied by a beneficial innate immune response in surrounding tissue may serve as a two-tiered approach to killing cancer cells while maintaining tissue integrity.

The identification of the ion channel repertoire opens up a range of specific therapeutic options that will be expected to provide enhanced cancer therapies. Investigation of that repertoire has allowed the applicants to determine specific elements that can give rise to new therapeutic actives that form an aspect of the invention as described further below.

SUMMARY OF THE INVENTION

According to the present invention, there is provided a biologically active complex comprising a polypeptide having the sequence of a variant of a naturally occurring protein, wherein said polypeptide is at least partially unfolded as compared to the said naturally occurring protein for example as a result of a modification of at least one cysteine residue; or a peptide of up to 50 amino acids; and a pharmaceutically acceptable salt of a fatty acid or lipid.

For example, the polypeptide present in the complex may have the sequence of a variant of α-lactalbumin or a variant of lysozyme.

As used herein, the term "biologically active" means that the complex has a biological activity, which is different from—or stronger than the individual components. In particular, the complex is able to induce cell death in particular selectively in tumour cells and/or has a bactericidal or antiviral effect not seen with the native protein including for example monomeric α-lactalbumin forms, although other therapeutic effects may be available.

The term "polypeptide" used herein includes proteins and peptides including long peptides.

Suitable peptides for use in the complex of the invention may be a fragment of the polypeptide or of the naturally occurring protein. The term "fragment" as used herein refers to any portion of the given amino acid sequence which will form a complex with the similar activity to complexes including the complete protein sequence such as an α-lactalbumin or lysozyme amino acid sequence. Fragments may comprise more than one portion from within the full-length protein, joined together. Portions will suitably comprise at least 5 and preferably at least 10 consecutive amino acids from the basic sequence.

Suitable fragments will include deletion mutants comprising at least 10 amino acids, for instance at least 20, more suitably at least 50 amino acids in length or analogous synthetic peptides with similar structures. They include small regions from the protein or combinations of these.

In a particular embodiment, there is provided a biologically active complex comprising a peptide of no more than 50 amino acids, and a pharmaceutically acceptable salt of a fatty acid or lipid.

The peptide has no more than 50 amino acids, and in particular may have from 10-45 amino acids. Such complexes are easier to prepare and the starting materials are less costly. For instance, peptides may be prepared using conventional methods for the production of peptides. The complexes formed may be easier to handle and formulate for administration, due to the smaller molecular weight.

It is suitably derived from a naturally occurring protein or a variant thereof. Suitable proteins are those identified as being active in such complexes, such as alpha-lactalbumin, beta-lactoglobulin or lysosyme. In particular, the peptide is a fragment of alpha-lactalbumin and specifically a fragment of the alpha domain of alpha-lactalbumin. In a particular embodiment, the peptide comprises amino acids of the Alpha 1 (residues 1-40) or Alpha 2 (residues 81-123) of human alpha-lactalbumin, or analogous regions of other alphalactalbumins such as bovine alpha-lactalbumin.

The peptide suitably contains no elements that give rise to folding and therefore suitably lacks amino acids that give rise to intramolecular bonding such as cysteine residues. In particular, where the peptide is derived from a naturally occurring protein, any cysteine residues are replaced by other amino acids such as alanine.

Thus in a particular embodiment, the complex comprises amino acids of the Alpha 1 (residues 1-40) or Alpha 2 (residues 81-123) of human alpha-lactalbumin wherein the cysteines are replaced with other amino acids such as alanine, to prevent any intra-molecular bonding.

Thus the peptide may be of SEQ ID NO 3 or SEQ ID NO 4

```
                                            (SEQ ID NO 3)
KQFTKXELSQLLKDIDGYGGIALPELIXTMFHTSGYDTQA (SEQ ID NO 4)
LDDDITDDIMXAKKILDIKGIDYWLAHKALXTEKLEQWLXEKL
``` where X is an amino acid residue other than cysteine.

A particular example of such sequences are those of SEQ ID NO 5 or SEQ ID NO 6.

```
                                            (SEQ ID NO 5)
KQFTKAELSQLLKDIDGYGGIALPELIATMFHTSGYDTQA (SEQ ID NO 6)
LDDDITDDIMAAKKILDIKGIDYWLAHKALATEKLEQWLAEKL
```

Other peptides may also be used in the complex and the suitability may be tested by determining whether complexes with a fatty acid salt are active, for instance in opening potassium ion channels and/or killing cells using methods as described hereinafter.

For instance, suitable fragments of α-lactalbumin are those described above which are derived solely from the alpha domains (FIG. 20), but others that may be selected include the region, which forms the alpha or the beta domains or the interface between the alpha and the beta domains, in human α-lactalbumin, defined by amino acids 34-38 and 82-86 in the structure. Thus suitable fragments will include these regions, and preferably the entire region from amino acid 40-105 of the native protein. However, other active fragments may be found.

The expression "variant" refers to proteins or polypeptides having a similar biological function but in which the amino acid sequence differs from the base sequence from which it is derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions are possible provided that these do not interrupt the function of the DNA binding domain polypeptides.

Broadly speaking, fewer non-conservative substitutions will be possible without altering the biological activity of the polypeptides.

Determination of the effect of any substitution (and, indeed, of any amino acid deletion or insertion) is wholly within the routine capabilities of the skilled person, who can readily determine whether a variant polypeptide retains the fundamental properties and activity of the basic protein. For example, when determining whether a variant of the polypeptide falls within the scope of the invention, the skilled person will determine whether complexes comprising the variant retain biological activity (e.g tumour cell death) of complexes formed with unfolded forms of the native protein and the polypeptide has at least 60%, preferably at least 70%, more preferably at least 80%, yet more preferably 90%, 95%, 96%, 97%, 98%, 99% or 100% of the native protein.

The level of sequence identity is suitably determined using the BLASTP computer program with the native protein sequences as the base sequence. This means that native protein sequences form the sequence against which the percentage identity is determined. The BLAST software is publicly available at <blast.ncbi.nlm.nih.gov/Blast.cgi> (accessible on 12 Mar. 2009).

The protein may comprise lysozyme and in particular equine lysozyme.

However, in a particular embodiment, the polypeptide is based upon the sequence of human α-lactalbumin but α-lactalbumin from other sources, including bovine or ovine α-lactalbumin may be used as the base protein.

In a particularly preferred embodiment, the polypeptide comprises a recombinant protein having the sequence of α-lactalbumin or a fragment thereof but which lacks intra-molecular disulfide bonds or cross-links. By ensuring that the recombinant protein lacks intra-molecular disulfide crosslinks, the molecule will be three-dimensionally non-native and completely inactive in terms of its original endogenous biological activity. This may be achieved for example by changing cysteine residues in the native α-lactalbumin to other residues, in particular alanine residues, although other means, for example by adding thiol compounds, or altering the pH of the protein may be considered. Preferably all cysteine residues will be changed to other residues, such as alanine residues. In particular the recombinant protein is based upon the sequence of human α-lactalbumin but α-lactalbumin from other sources, including bovine or ovine α-lactalbumin may be used to derive the recombinant protein.

In a particular embodiment, the polypeptide is a recombinant protein having the sequence of native mature α-lactalbumin but which has all of the cysteines found at positions 6, 28, 61, 73, 77, 91, 111 and 120 in the full length sequence of mature human α-lactalbumin mutated to other amino acids, such as alanine, which do not give rise to disulphide bridges. Thus a particular of a protein that may be utilised in accordance with the invention comprises a protein of SEQ ID NO 1.

(SEQ ID NO 1)
KQFTKAELSQLLKDIDGYGGIALPELIATMFHTSGYDTQAIVENNESTEYGLFQISNKLWAKSSQ

VPQSRNIADISADKFLDDDITDDIMAAKKILDIKGIDYWLAHKALATEKLEQWLAEKL where the bold type indicates positions of mutations of cysteines in native human α-lactalbumin.

As reported in WO2010079362, additional amino acid residues, for example up to 20 amino acids, may be attached at N and/or C terminal of the protein, if convenient, for example for expression purposes. Thus in particular, a recombinant protein as shown in SEQ ID NO. 1 but with an additional methionine at the N-terminus (SEQ ID NO 2 shown below) has been used in the method of the invention.

(SEQ ID NO 2)
MKQFTKAELSQLLKDIDGYGGIALPELIATMFHTSGYDTQAIVENNESTEYGLFQISNKLWAKSS

QVPQSRNIADISADKFLDDDITDDIMAAKKILDIKGIDYWLAHKALATEKLEQWLAEKL

Variants of the polypeptide may comprise or consist essentially of an amino acid sequence with at least 70% identity, for example at least 75%, 80%, 85%, 90%, 91%, 92%, 93%, 94%, 96%, 97%, 98% or 99% identity to a native protein sequence such as an alphalactalbumin or lysozyme sequence.

The polypeptide used in the complex is suitably in pure form, and is suitably prepared using conventional methods of peptide synthesis or by recombinant expression. In particular, DNA encoding the required recombinant α-lactalbumin can be inserted into suitable expression vectors such as plasmids, which can then be employed to transform host cells, for example, prokaryotic cells such as *E. coli* or eukaryotic cells such as particular insect cells using conventional methods.

In particular the salt of fatty acid or lipid present in the complex of the invention is a water soluble salt. Particular examples of suitable salts may include alkali or alkaline earth metal salts. In a particular embodiment, the salt is an alkali metal salt such as a sodium- or potassium salt.

Suitably fatty acids or lipids include those known to provide biologically active complexes. These include fatty acids, for example as described in WO2008058547.

Particular examples of fatty acids or lipids that form the basis of the salts used in the present invention are those having from 4-30, for example from 6 to 28, such as from 8 to 26 carbon atoms. In particular embodiments, the fatty acid or lipid has from 10 to 24, such as from 12 to 22, for example from 14 to 20 carbon atoms. In particular, the fatty acid or lipid will have 16, 17, 18 or 20 carbon atoms. The fatty acids may be saturated or unsaturated.

In particular however, the complexes of the invention utilize salts of acids having 18 carbon atoms. A specific example is a salt of oleic acid, and in particular a salt of C18:1 oleic acid of formula $CH_3(CH_2)_7CH=CH(CH_2)_7COOH$ or $CH_3(CH_2)_7CH=CH(CH_2)_7COO^-$.

The complex may be prepared using methods similar to those described for example in WO99/26979 and WO2008/138348, the content of which is incorporated herein by reference.

According to a further aspect of the present invention there is provided a method for preparing a biologically active complex as described above. Said method may comprise combining together polypeptide having the sequence of a variant of a naturally occurring protein, wherein said polypeptide is at least partially unfolded as compared to the said naturally occurring protein; or a peptide of up to 50 amino acids; with a salt of a fatty acid or lipid under conditions in which they form a biologically active complex.

When a peptide of up to 50 amino acids is used in the complex, the preparation may be carried out simply by mixing together a suitable peptide and an oleate, for example in a solution such as an aqueous solution. The ratio of oleate: peptide added to the mixture is suitably in the range of from 20:1 to 1 to 1, but preferably an excess of oleate is present, for instance in a ratio of oleate:peptide of about 5:1. The mixing can be carried out at a temperature of from 0-50° C., conveniently at ambient temperature and pressure. This simple preparation method provides a particular advantage for the use of such peptides in the complexes. The methods can be carried out in situ, when required for treatment. Thus kits may be provided comprising peptides and salts for mixing immediately prior to administration. Such kits, and reagents for use in the kits form a further aspect of the invention. Peptides are suitably synthetic peptides although they may be prepared by recombinant DNA technology.

Where the complex comprises a larger polypeptide, the preparation method may have to be different. In particular, the invention provides a method for preparing a biologically active complex comprising a polypeptide having the sequence of a naturally occurring protein or a variant, wherein said polypeptide is at least partially unfolded as compared to the said naturally occurring protein; or a fragment of any of these and a pharmaceutically acceptable salt of a fatty acid or lipid, said method comprising combining together a polypeptide having the sequence of a naturally occurring protein or a variant thereof, wherein said polypeptide is at least partially unfolded as compared to the said naturally occurring protein or a variant or fragment thereof, with a salt of a fatty acid or lipid in the presence of an ion exchange material under conditions in which they form a biologically active complex, provided that when the naturally occurring protein is alphalactalbumin, it is human alphalactalbumin.

Suitable polypeptides are as described above and in particular have the sequence of human alphalactalbumin or lysozyme or a variant or fragment thereof.

Use of a salt, and in particular a water soluble salt of the fatty acid or lipid means that the preparation method is facilitated since aqueous solutions may be formed for instance for application to ion exchange columns and the like.

Methods for preparing complexes comprising a polypeptide will be analogous to those used to prepare HAMLET and related complexes for example in WO9926979, WO2008058547, WO2008138348 and WO2010079362. In all these cases, the active complex is formed by contacting a protein with a fatty acid or lipid, and in particular oleic acid, under specific conditions such as ion exchange conditions and recovering active product. In to produce complexes according to the present invention, a solution comprising a salt of a fatty acid or lipid will be used instead of pure oleic acid. The protein is generally in a non-native folding state and in particular is partly unfolded or in a molten globule state, which may require pre-treatment in some instances. The use of a salt solution addresses a particular problem of the prior art in that the fatty acid or lipid used is not water soluble, making handling difficult. Salts may be water soluble and thus avoid this problem.

WO2010/131237 describes methods for producing biologically active complexes by contacting a protein such as alphalactalbumin, beta-lactoglobulin and lysozyme, with an excess of a water soluble salt of a fatty acid in the presence of globular protein denaturing conditions. They report also that when attempts were made to produce these complexes with a bovine alphalactalbumin using a chromatographic column in the manner previously described for the production of HAMLET, yields were significantly lower. The applicants have also found that such products may be prepared instead with water soluble salts of fatty acids to produce highly effective complexes without loss of activity but with a greater ease of production. Thus it appears that the presence of a protonated moiety is not essential for the formation of stable complexes.

However, they have also found that when the protein applied to a column is human alphalactalbumin, and the column has been pretreated or conditioned using a solution of a salt of oleic acid, yields are comparable or better than those achieved using oleic acid. This is surprising in the light of the disclosure of WO2010/131237.

Furthermore, salts of fatty acids and in particular oleates have been found to have intrinsic activity in activating the ion channels found to be relevant to the activity of HAMLET. Hence it may be expected that the use of such salts may be beneficial in a clinical capacity or as a component of new therapeutic entities. Some such entities form a further aspect of the invention.

The polypeptide used in the process is in an unfolded state and therefore, if subject to folding, they may require a preliminary treatment step to unfold them. This may be achieved for instance under acidic conditions and similar states are formed at neutral pH upon removal of the tightly bound $Ca^{2+}$-ion by a chelating agent such as EDTA (ethylene diamine tetraacetic acid), by reduction of the disulfide bonds, or at elevated temperatures (Pfeil, 1987 Biochim Biophys Acta, 911:114-116; Kuwajima, 1996 Faseb J. 10:102-109; Schulman et al., 1995 J. Mol. Biol. 253, 651-657).

However, by use of a polypeptide which is synthesised according to the sequence of a protein which lacks intra-molecular disulfide bonds or cross-links, there is no need for pretreatment steps, for example by treatment with a calcium chelating agent such as EDTA, subjecting the material to low pH or high temperature, in order to remove calcium and increase the amount of molten globule-like material present.

In particular, when using the method of the invention, high yields of biologically active complex are obtained conveniently, The polypeptide as defined above is active when mixed with the lipid, The unfolded protein is suitably contacted with the salt of the fatty acid or lipid under conditions which allow ion exchange to take place in particular on an ion exchange column, specifically an anion exchange column such as a DEAE-Trisacryl M column (available from BioSepra, Villeneuf, France). The column is suitably "pre-conditioned" with a salt of the fatty acid such as sodium oleate, before the protein is applied to it. This may be achieved by eluting or conditioning the column first with the salt, which is suitably in the form of an aqueous solution. Suitably the salt solution is eluted through a column containing new unused or reconditioned ion exchange material such as DEAE Trisacryl. Suitable elution buffers include Tris-HCl and NaCl with a pH of 8.5. The amount of salt solution applied to the column in this way may be small depending upon factors such as the size of the column and the volume of recombinant protein required to be converted to biologically active complex. For example, it has been found that only 10 mg of oleic acid can be used to condition a column of 14 cm×1.6 cm.

After the polypeptide has been applied to the column (for example in solution in a suitable buffer), it is then eluted with a linear salt gradient, and the fraction eluting at high salt (0.7-1 M NaCl or equivalent) is isolated.

Alternatively, as described in WO2008138348, the polypeptide may be mixed with a solution of the fatty acid or lipid prior to contact with an ion exchange medium, in particular by elution down an ion exchange column.

Thus in a particular embodiment, the invention provides a method of producing a biologically active complex, said method comprising contacting a polypeptide having the sequence of α-lactalbumin or variant thereof which lacks intra-molecular disulfide bonds (crosslinks), with a salt of oleic acid on an anion exchange column under conditions in which a biologically active complex is formed, eluting the column with a salt gradient and isolating the complex from a fraction eluting at high salt concentration.

The expression "high salt concentration" refers to concentrations of salts with cations such as halides and in particular chlorides at concentrations in excess of 0.5M, for example in excess of 0.75M and in particular at about 1M. The concentration required may vary depending upon the salt used, but in a particular embodiment, the salt is NaCl, and suitably 0.7-1M NaCl.

Suitably the salt of oleic acid used in the process is in pure form.

A pre-treated column can be used repeatedly to convert numerous fractions of a natural as well as recombinant protein having the sequence of α-lactalbumin or a fragment thereof to biologically active complex as described above. Once the column is exhausted or the conversion rate drops to unacceptable levels, the pre-treatment step can be repeated in order to restore the complex production activity.

A further aspect of the invention comprises an ion exchange medium that has been pretreated with a solution, suitably an aqueous solution, of a salt of a fatty acid or lipid, in particular oleic acid, for use in a process as described above.

Suitable ion exchange mediums are anionic exchange resin, which may be strong or weak anion exchangers. For instance, in a particular embodiment, the ion exchange medium may be DEAE Trisacryl but alternatives include DEAE Ceramic, Capto Q, DEAE Sepharose Q, Sepharose XL, Q Sepharose XL, Source 3OQ or Unosphere Q. In a particular embodiment, the ion exchange medium is a strong Quaternary ammonium (Q) based resin. Particle sizes suitably range from 40-165 microns. In particular, the ion exchange medium is in the form of a conventional ion exchange column.

The complexes obtained as described using human alpha-lactalbumin and sodium oleate has been found to be biologically active in that it has activity in inducing tumour cell-death for instance by apoptosis and/or have a bactericidal effect that is at least equal to that obtained with other biologically active complexes such as HAMLET. Furthermore, it has been found that salts and in particular oleate salts such as sodium oleate appear to have some inherent tumoricidal effect. Therefore the inclusion of this in the complex may give rise to activity increases.

However, the salts may also have utility therapeutics, for instance in combination with other anti-cancer therapeutics including complexes. The use of such salts in this way, and pharmaceutical compositions for the treatment of cancer containing such salts, form yet further aspects of the invention.

Furthermore, it has been found that complexes of this general type may target specifically cell nuclei and so they may be used to effectively 'carry' reagents into the nuclei of cells to maximize their effect. This is particularly useful where the complex specifically targets a tumour cell for instance. Thus the complexes may further comprise a secondary reagent which is combined with the complex such that it is carried into the nucleoplasm of cells which are susceptible to the complex. Analogous complexes are described for instance in WO 99/27967.

The said secondary reagent may be coupled by conjugation or by covalent bonding for example by way of a linking or spacer group as would be understood in the art. Enzymatic reactions can mediate or facilitate the coupling.

Recombinant production techniques allow also the possibility that the polypeptide of the complex could be produced in the form of a fusion protein with the said secondary reagent.

Examples of said secondary reagents include cytoxins such as known chemotherapeutic reagents used for the treatment of cancer, microbial toxins such as diptheria toxin and monoclonal antibodies. Alternatively, the said secondary reagent comprises a labelling agent such as biotin or radioactive labels such as $^{125}$I. For example, a labelling group can be introduced into a protein using an enzymatic reaction or by having a labelled building stone (such as radioactive isotopes e.g. $^{14}$C, $^{35}$S,) within the protein. $^{125}$I-labelling can be performed enzymatically by coupling $^{125}$I to the protein with the help of lactoperoxidase. Biotinylation of the protein is performed by letteing D-biotinoyl-ε-aminocaproic acid-N-hydroxysuccinimide ester react with the protein by forming a stable amide bond to free amino groups in the protein.

Protein may also be labelled by adding radioactive amino acid during the production of a recombinant protein.

Depending upon the nature of the said secondary reagent, the complex of the invention can be used in the diagnosis and/or treatment of cancer. For this purpose, the complex is suitably formulated as a pharmaceutical composition.

Thus, complexes as described above and/or oleate salts also as described above, may be formulated into useful pharmaceutical compositions by combining them with pharmaceutically acceptable carriers in the conventional manner. Such compositions form a further aspect of the invention.

The compositions in accordance with this aspect of invention are suitably pharmaceutical compositions in a form suitable for topical use, for example as creams, ointments, gels, or aqueous or oily solutions or suspensions. These may include the commonly known carriers, fillers and/or expedients, which are pharmaceutically acceptable.

Topical solutions or creams suitably contain an emulsifying agent for the protein complex together with a diluent or cream base.

The daily dose of the complex varies and is dependant on the patient, the nature of the condition being treated etc. in accordance with normal clinical practice. As a general rule from 2 to 200 mg/dose of the biologically active complex is used for each administration.

In a further aspect of the invention, there is provided a method for treating cancer which comprises administering to a patient in need thereof, a biologically active complex as described above.

In particular, the complex may be used to treat cancers such as human skin papillomas, human bladder cancer and glioblastomas. In the latter case, administration may be by infusion as is known in the art.

The invention further provides the biologically active complex as defined above for use in therapy, in particular in the treatment of cancer.

Furthermore, it has been found that use of a salt of a fatty acid instead of the fatty acid itself in the production leads to an enhanced yield of biologically active complex, which is quite unexpected.

However, as mentioned above, the identification of the ion channel repertoire opens up a range of specific therapeutic options that will be expected to provide enhanced cancer therapies.

Thus according to a further aspect of the invention there is provided a method for selectively targeting cancer cells which comprises applying to a patient in need thereof
(i) a reagent that selectively modulates ion channels in a cellular membrane and is inhibited by Amiloride or comparative substances; and/or
(ii) a reagent that selectively modulates potassium channels in a cellular membrane and is inhibited by barium chloride ($BaCl_2$) or comparative substances; in combination with
(iii) a reagent that causes cell death at least in tumor cells.

The applicants have found that these particular channels may be more susceptible to modulation in tumor cells than they are in healthy cells and that therefore, by specifically targeting these channels, the selectivity of cytotoxic agents for tumor cells may be increased by co-administration of these substances, thereby reducing the risk of side effects.

As used herein, the term "selectively modulates" means that the reagent acts on or activates a limited number of ion channels only. In doing so, the reagent will be able to have an therapeutic impact on the cell but also by limiting the effects to those channels that are particularly sensitive in tumour cells, this will minimize non-specific effects on healthy cells. In the case of reagent (i) above, such reagents may be identified by virtue of the fact that they are inhibited by Amiloride (3,5-diamino-6-chloro-N-(diaminomethylene)pyrazine-2-carboxamide) or other comparative substances. In the case of reagent (ii) above, such reagents may be identified by virtue of the fact that they are inhibited by $BaCl_2$ or other comparative substances.

As used herein, the expression "comparative substances" refers to channel blockers with comparable activity or substances that modulate similar ion channels in a similar manner to the reference compound. Generally however, the reagents for use in the invention will be able to be identified with reference to the ability of the reference compounds to inhibit the ion channel modulation using conventional methods, for instance as illustrated hereinafter in the examples.

Suitably the reagents (i) and (ii) do not modulate or open mechanosensitive channels in the sense that they are not inhibited by Gadolinium chloride ($GdCl_3$), or general $Ca^{2+}$ channels as illustrated by their being inhibited by ruthenium red (ammoniated ruthenium oxychloride), or large conductance $Ca^{2+}$ activated potassium channels as illustrated by inhibition by tetrandrine (6,6',7,12-tetramethoxy-2,2'-dimethyl-1 beta-berbaman).

In a particular embodiment, reagents (i), (ii) and/or (iii) may comprise a single reagent which will be other than HAMLET or known therapeutic analogues thereof. Analogues of HAMLET are known for example from WO03074547, the content of which is incorporated herein by reference.

A particular form of single reagent that may achieve this function is a biologically active complexes as described above.

However, this aspect of the invention may be fulfilled by combination therapies, in which for instance, a reagent which is effective relatively non-specific cytotoxic agents are associated with a reagent that fulfills the requirement of (i) and/or (ii) above or a combination of reagents that achieve this effect. The cytotoxic agents (iii) may be associated with the reagents of (i) and/or (ii) by being linked for example covalently linked to the molecules. However, association by means of complex formation or other hydrogen bonding effects may also suffice.

However, examples of such reagents (i) and/or (ii) may include unfolded protein-lipid complexes (other than HAMLET), antibodies, small molecules, siRNAs or shRNAs, lipids or lipid salts. The reagents may be known ion channel modulators or suitable reagents may be identified using suitable screening methods, for example as described below.

In particular, the cytotoxic agent is one that interacts with the p38 pathway to bring about the killing effect.

Other aspects of the invention include a composition for selectively targeting cancer cells, said composition comprising
(i) a reagent that selectively modulates ion channels in a cellular membrane and is inhibited by Amiloride or comparative substances; and/or
(ii) a reagent that selectively modulates potassium channels in a cellular membrane and is inhibited by barium chloride ($BaCl_2$) or comparative substances; in combination with
(iii) a reagent that causes cell death at least in tumor cells.

Such compositions may comprise a single composition or, where the components are individual components, they may be packaged separately for sequential or concurrent administration. The compositions will generally further comprise pharmaceutically acceptable carriers as is conventional in the art. They include pharmaceutically acceptable solid or liquid diluents.

In a particularly preferred embodiment, the compositions are pharmaceutical compositions in a form suitable for topical use, for example as creams, ointments, gels, or aqueous or oily solutions or suspensions. These may include the commonly known carriers, fillers and/or expedients, which are pharmaceutically acceptable.

Topical solutions or creams suitably contain an emulsifying agent for the protein complex together with a diluent or cream base.

Furthermore, the invention provides a method for identifying reagents that may be useful in the above methods and compositions, the method comprising applying a test reagent to a cell; determining the effect on ion channels in the presence and absence of Amiloride or a comparative substance; and/or in the presence or absence of $BaCl_2$ or comparable molecules; and identifying those reagents whose activity is inhibited by the presence of at least one of Amiloride or $BaCl_2$.

The effect on ion channels may be determined for instance by co-administration of an indicator that is able to permeate cells when ion channels are open. Once present in the cells, such indicators react in the cellular environment so as to develop a detectable signal. One such indicator is FLUXOR™ available from Tecan Group, Switzerland.

Suitably, the cell used in the test is a tumour cell that has been found to be particularly susceptible to reagents that modulate ion channels in this way. However, the fact that this channel repertoire is shared by bacteria may mean that the cells used in the screen method may be bacterial cells since in effect, bacterial cells may provide a mimic of susceptible tumour cells in this instance.

In order to ensure optimum selectivity for tumour cells, in a particular embodiment, the test is carried out also in the presence and absence of at least one inhibitor selected from gadolinium, tetrandrine and ruthenium red, and those compounds where the presence or absence of the inhibitor does not affect the cell permeability in these instances may be selected as a preferred candidate for further evaluation.

Suitable test reagents include small molecules and chemical moieties as well as unfolded protein-lipid complexes (other than HAMLET), antibodies, small molecules, siRNAs or shRNAs, lipids or lipid salts.

While oncogenic transformation and cancer cell function require ion channel support, ion channel variability and complexity is considerable. Ion channel-encoding genes are frequently over-expressed in human cancers, due to gene amplifications, epigenetic regulation or splice variants of channel encoding genes. Except KCNRG, encoding a K+ channel-regulating protein with tumor suppressor properties, tumor-specific mutations in ion channel genes have not been reported, however. In addition, most human cancer cells show altered Ca2+ wave dynamics and but cancer-specific alterations in the "spatio-temporal nature" of Ca2+ waves or ion channel expression profiles have largely not been identified (Arcangeli et al., supra. 2009) but several approaches have been discussed in the literature. In specific cell types, siRNA mediated inhibition of individual ion channels has been found efficient, but due to the complexity, knockdown of individual channels is often insufficient to obtain loss of function and a distinct phenotype. The use of pharmacologic channel inhibitors therefore remains crucial for defining the general involvement of different functional classes of ion channels. With this in mind, the results illustrated hereinafter suggest that the perturbation of tumor cell membranes and opening of certain ion channels, as demonstrated by HAMLET, can be used as a mechanism for discriminating tumor cells from healthy, differentiated cells. This finding may be used to enhance the selectivity and reduce side effects in many chemotherapeutic situations.

The recorded $Ca^{2+}$ and $K^+$ fluxes and inhibition of cell death by Amiloride and $BaCl_2$ suggested that both $Na^+/$ mechanosensitive channels and potassium channels are opened by HAMLET. This pattern of ion channel activation is consistent with our recent studies in artificial vesicles and tumor cell membrane models. Fluorescence imaging showed that HAMLET accumulates in receptor-free phospholipid membranes and perturbs their structure by elongation. Similar results were obtained with plasma membrane vesicles from tumor cells, which formed tube-like membrane invaginations after HAMLET exposure. Furthermore, there is evidence that HAMLET forms pores in artificial lipid bilayers explaining why HAMLET induces membrane leakage at physiologic pH in addition to ion channel activation, direct permeabilisation of carcinoma cell membranes by HAMLET might start a channel-independent $Ca^+$ mobilization. This would explain why cell death was not inhibited by Gadolinium chloride ($GdCl_3$), which inhibits MSC channels, by Ruthenium red, which is a general $Ca^{2+}$ inhibitor or Tetrandrine, which inhibits large conductance, $Ca^{2+}$ activated potassium channels.

This complex mechanism of action was further supported by the ionophore experiments, demonstrating that HAMLET does not completely permeabilize the membrane or cause necrotic cell death. This is essential for the understanding of the complex, as cell membranes are perturbed by lipids and an overload of oleic acid has been shown to cause cell lysis. In this study, oleic acid alone did not show ion channel activating activity at concentrations relevant for the HAMLET complex, emphasizing the need for both the unfolded protein and the lipid to achieve these specific effects on ion channels and signaling.

Unfolded protein species that form amyloid have, in some cases, shown cytotoxic activity, which has been explained by pore-formation in cell membranes. Furthermore, the cellular spectrum of amyloid oligomers is very different from that of HAMLET, however, with toxicity for healthy tissues being a major problem. We thus speculate that the tumoricidal effects of HAMLET may reflect the combined effects on mechanosensitive and $Ca^{2+}/K^+$ activated channels, against a background of transient membrane permeabilisation.

HAMLET was shown to shift the MAPK signaling profile of tumor cells from the ERK1/2 to the p38 pathway, and thus from proliferation to cell death. These results are consistent with reported effects of ion channels on cellular response pathways. In mammals, MAPKs are divided into three major groups, ERKs, JNKs/stress-activated protein kinases, and p38, based on their degree of homology, biological activities, and phosphorylation motifs. JNK and p38 are key mediators of stress signals stimulated by various stresses such as UV and γ-irradiation, osmotic stress, and heat shock; pro-inflammatory cytokines such as tumor necrosis factor-α and interleukin-1β; and chemotherapeutic drugs and seem to be responsible mainly for protective responses, stress-dependent apoptosis, and inflammatory responses.

In healthy differentiated cells, HAMLET targeted signaling pathways involved in innate immunity and transiently suppressed p38 signaling. Although this immune response was low or absent in tumor cells, similar immune response pathways were strongly regulated in carcinoma cells under p38-specific inhibition, suggesting that these are not completely separate cellular response strategies. The mobilization of intracellular $Ca^2$ by HAMLET in both carcinoma cells and healthy cells might indicate that this activation mechanism is shared, albeit of different magnitude. The subsequent ion channel response was mainly observed in the carcinoma cells, however, suggesting that this is the critical step to trigger cell death, a hypothesis also supported by the rescue effects of the ion channel blockers. This innate arm of the immune response would ideally serve to activate macrophages and other cells that scavenge and digest the remnants of apoptotic cells at sites of tissue damage and provide a suitable immune environment for cancer cell removal. We speculate that HAMLET's ability to selectively kill a broad range of tumor cells combined with the innate immune response of healthy differentiated cells may explain the low toxicity of HAMLET in clinical studies as well as its beneficial effects. The p38 effector response in tumor cells accompanied by a beneficial innate immune response in surrounding tissue may serve as a two-tiered approach to killing cancer cells while maintaining tissue integrity.

The invention will now be particularly described by way of example with reference to the accompanying drawings which show the results of experiments as set out below.

The experiments giving rise to the invention will now be particularly described by way of illustration and example.

(A) The transcriptional response to HAMLET is qualitatively different in normal cells (RPTEC), as shown by the heat map of genes with a log 2 fold change >2 at any time point. (B) The number of differentially expressed genes (log 2 fold change ≥2) was reduced compared to carcinoma cells. (C) Seven innate immunity-related genes are upregulated in normal cells, 75 minutes after HAMLET treatment. Two genes, p38 and MKK3/6 are downregulated. (D) Confirmation of the innate immune response to HAMLET. Elevated TNF, IL-8 and IL-6 levels in supernatants of normal, differentiated cells, but not in carcinoma cells treated with HAMLET (21-42 μM, 6 h). Data are means±SEMs of triplicates from 3 independent experiments. (E, F) Difference in phosphorylation of p38 between normal differentiated cells (HRTEC) and kidney carcinoma cells, visualized by phospho-specific antibodies.

Figure 7:
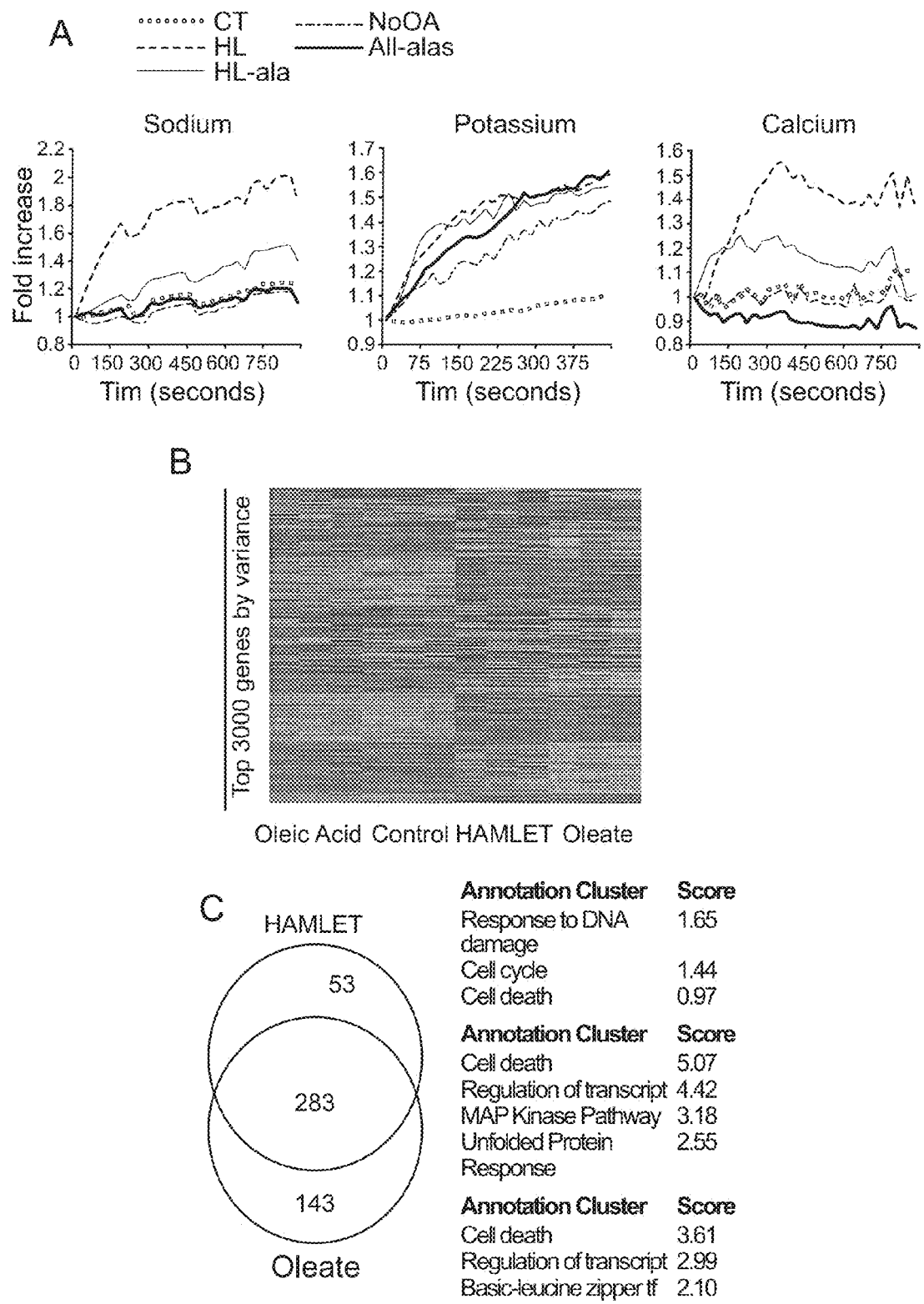
Figure 7:
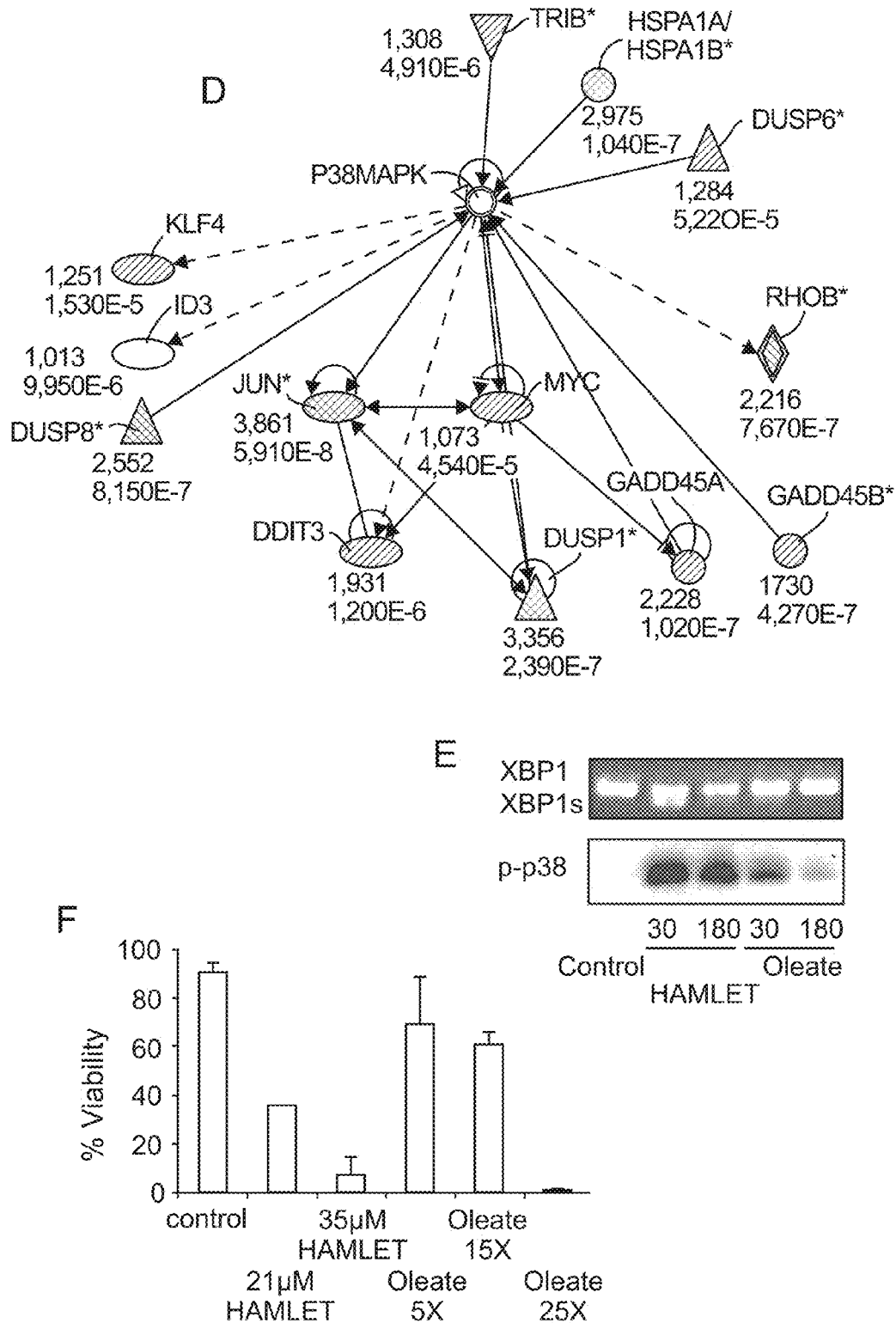

FIG. 7. (A) Ion fluxes induced by HAMLET (35 μM) or it constituents (35 μM All-ala α-lactalbumin or 175 μM sodium oleate) were quantified by fluorometry, as described. Both constituents showed independent, ion channel activating activity. The partially unfolded α-lactalbumin$^{all-ala}$ mutant triggered K$^+$ fluxes comparable to HAMLET and weaker Na$^+$ or Ca$^{2+}$ fluxes. Oleate triggered K$^+$ fluxes, but effects on Na$^+$ or Ca$^{2+}$ fluxes were low. (B) The global transcriptional response to HAMLET was studied by microarray and the top 3000 genes by variance visualized in a Heatmap. HAMLET and oleate caused a very similar transcriptional response whereas oleic acid was similar to untreated controls. Darker bands=high expression, lighter bands=low. (C) Differentially expressed genes (log 2-fold change of greater than 1 compared to PBS-treated control cells and adjusted p-value <0.05) were very similar between HAMLET and oleate treated cells. (D) Using Ingenuity Pathway Analysis p38 and genes associated with p38 were visualized in a signaling network and shown to be upregulated by HAMLET or oleate. (E) HAMLET and oleate caused splicing of XBP1, indicative of ER stress, as well as phosphorylation of p38. (F) Concentrations of oleate corresponding to 15× that of HAMLET (35 μM) were not tumoricidal.

Figure 8:
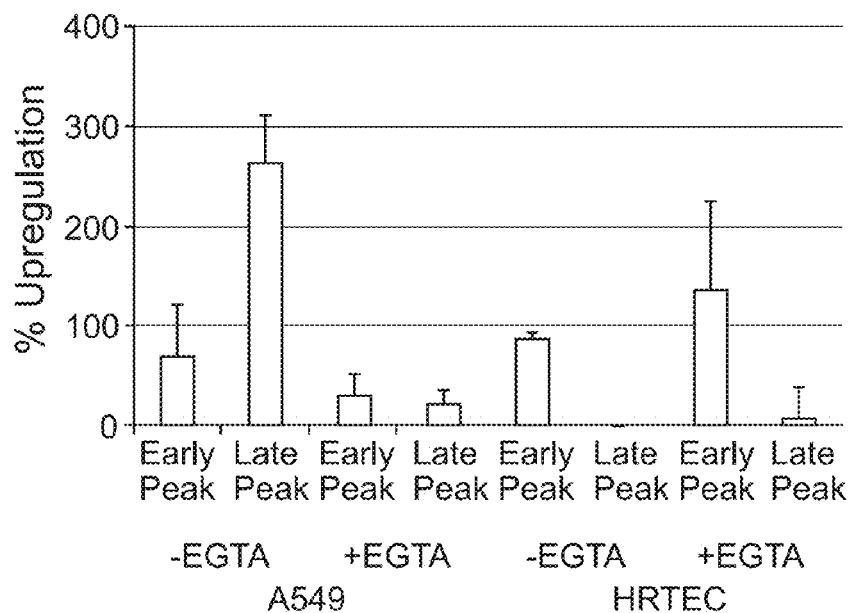

FIG. 8. Magnitude of Ca2+ peaks with different inhibitors. Carcinoma cells (A549) and healthy, differentiated cells (HRTEC) were pretreated with inhibitors and calcium-free media as indicated. The magnitude of the first and second Ca2+ peaks were quantified using the LSM Software.

Figure 9:
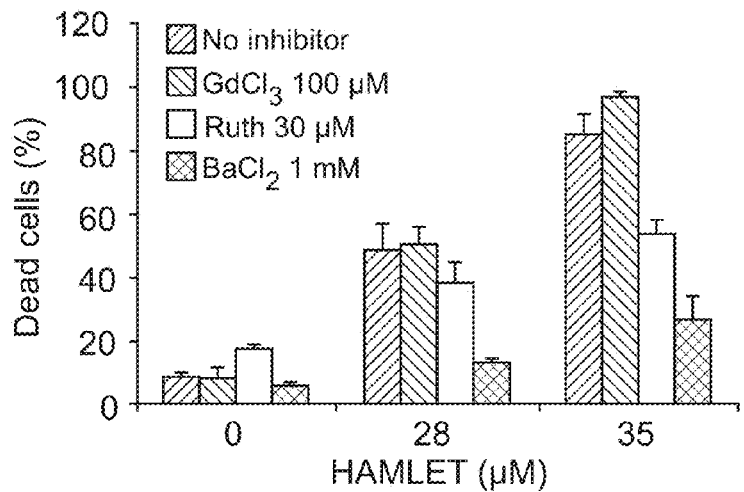
Figure 9:
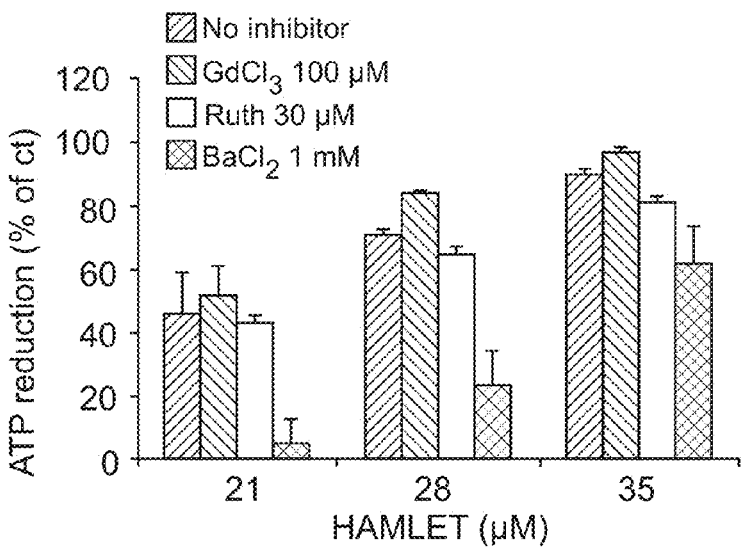
Figure 9:
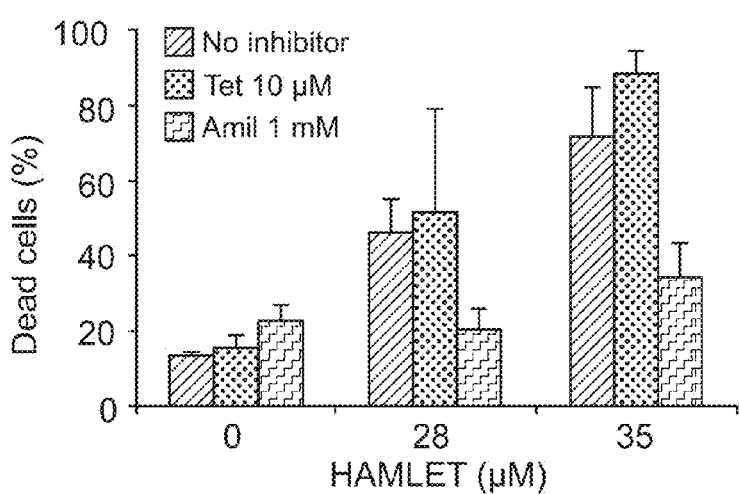
Figure 9:
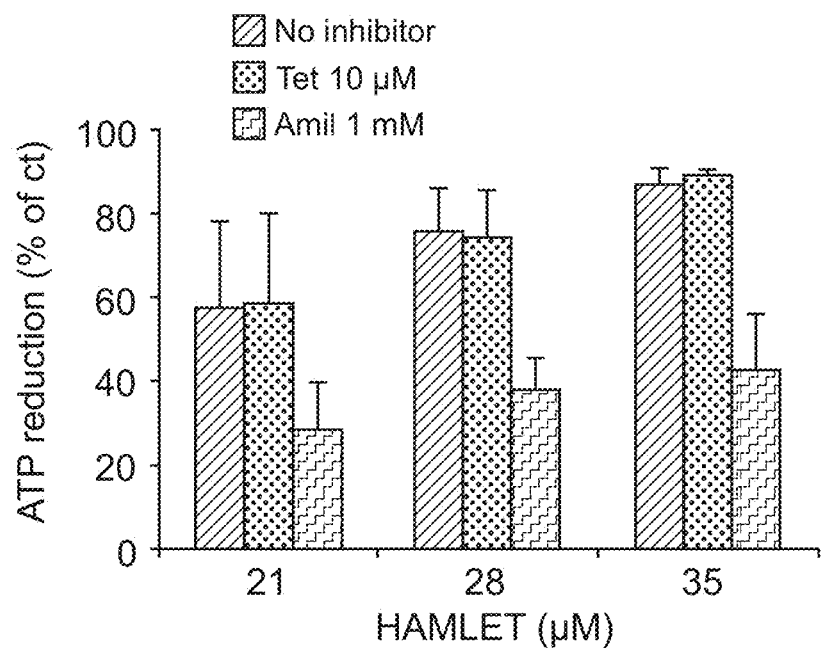
Figure 9:
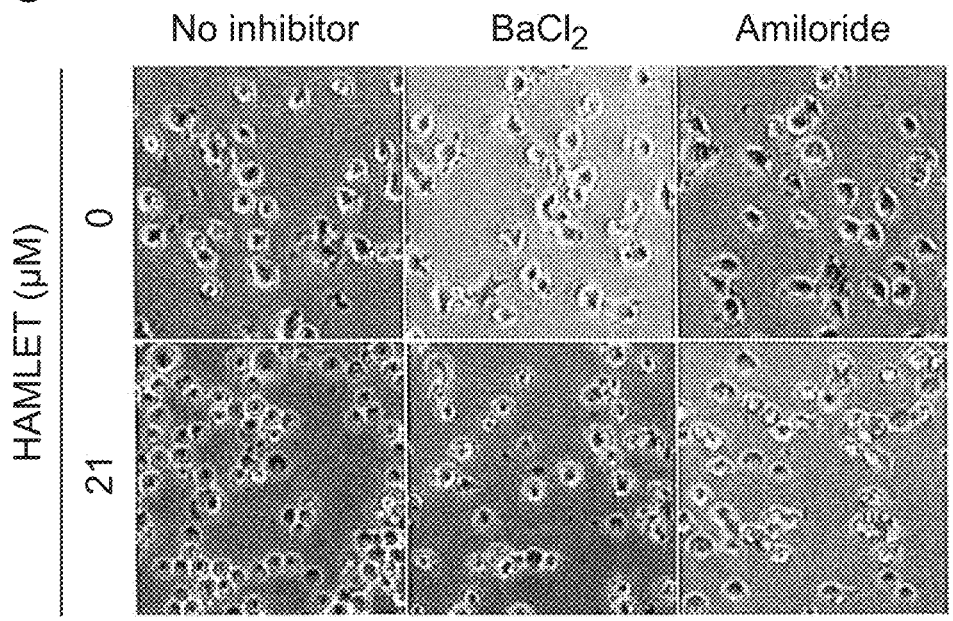
Figure 9:
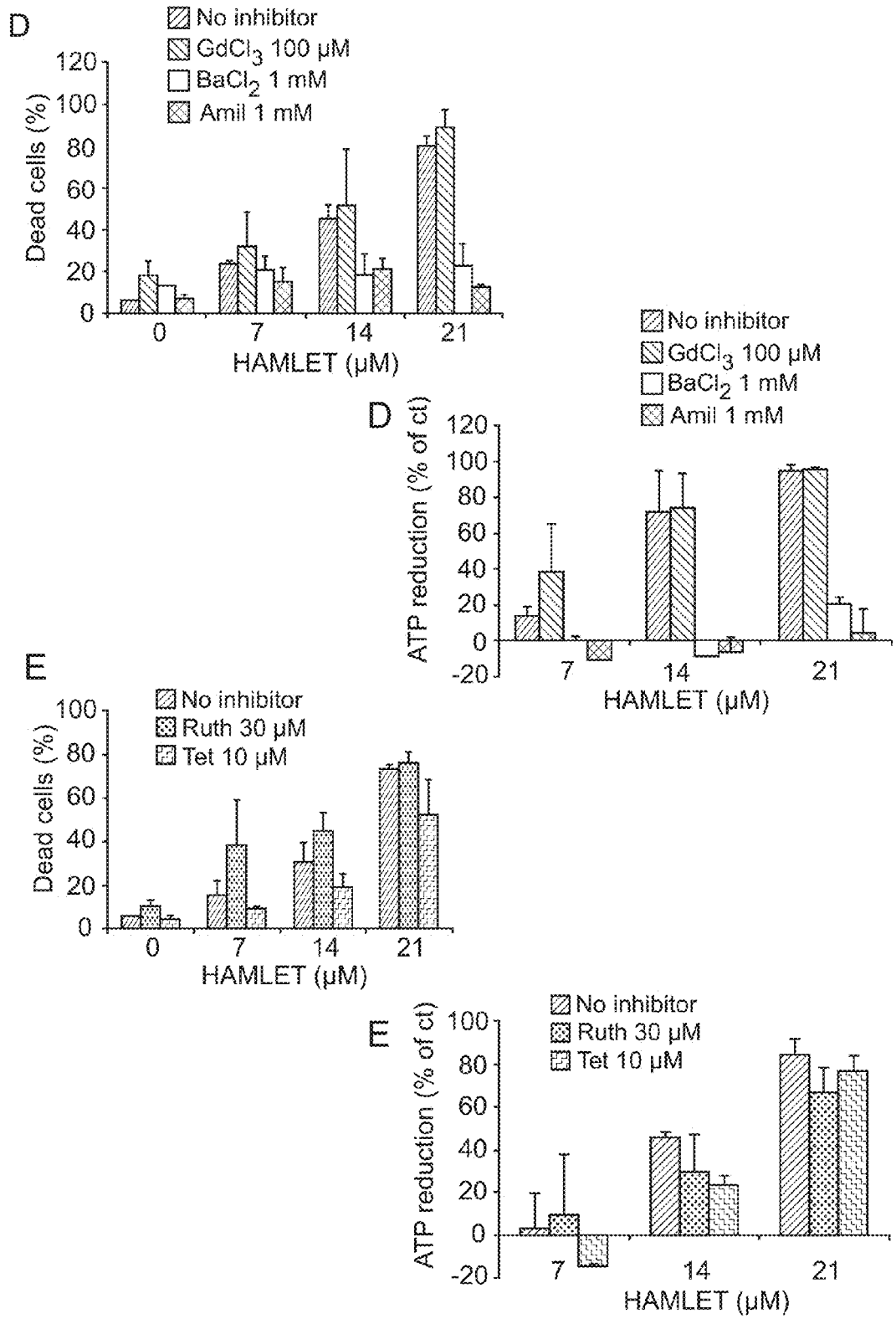

FIG. 9. Ion channel inhibitors rescue cells from HAMLET induced cell death.
(A, B) HeLa cells were pre-incubated with ion channel inhibitors as indicated and treated with HAMLET (21-35 μM) for three hours. Cell death was quantified by trypan blue assay and ATP levels (upper and lower, respectively). (C) The results of some tests were visualized by confocal microscopy. (D, E) Jurkat Lymphoma cells were pre-incubated with ion channel inhibitors as indicated and treated with HAMLET (21-35 μM) for three hours. Cell death was quantified by trypan blue assay and ATP levels (upper and lower, respectively).

Figure 10:
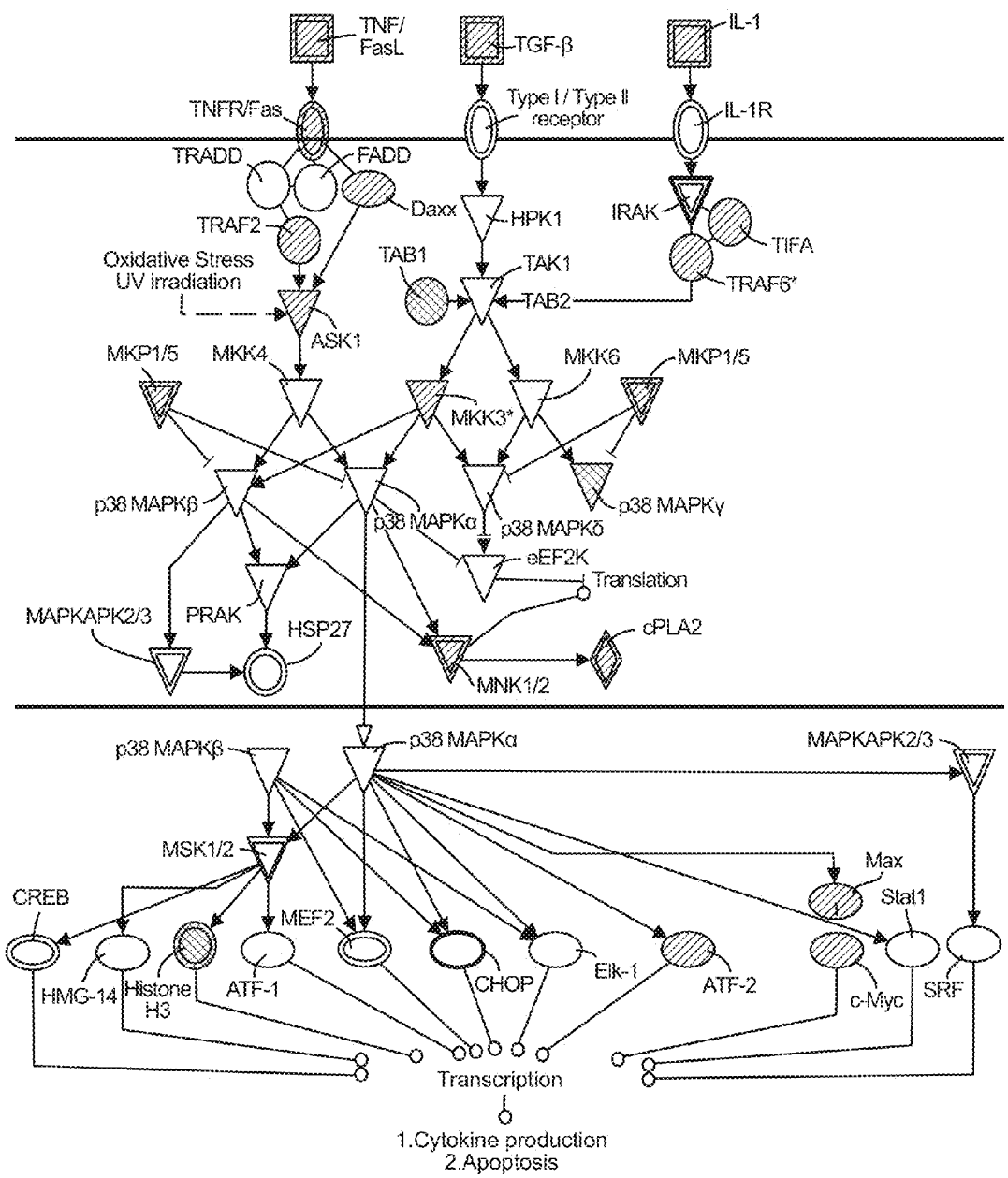

FIG. 10. Differential expression of genes in the p38 signalling pathway.
A498 human kidney carcinoma cells were exposed to HAMLET for three hours and differentially expressed genes were functionally categorized using Ingenuity Pathway Analysis. The p38 signaling pathway was identified as the top-scoring pathway.

Figure 11:
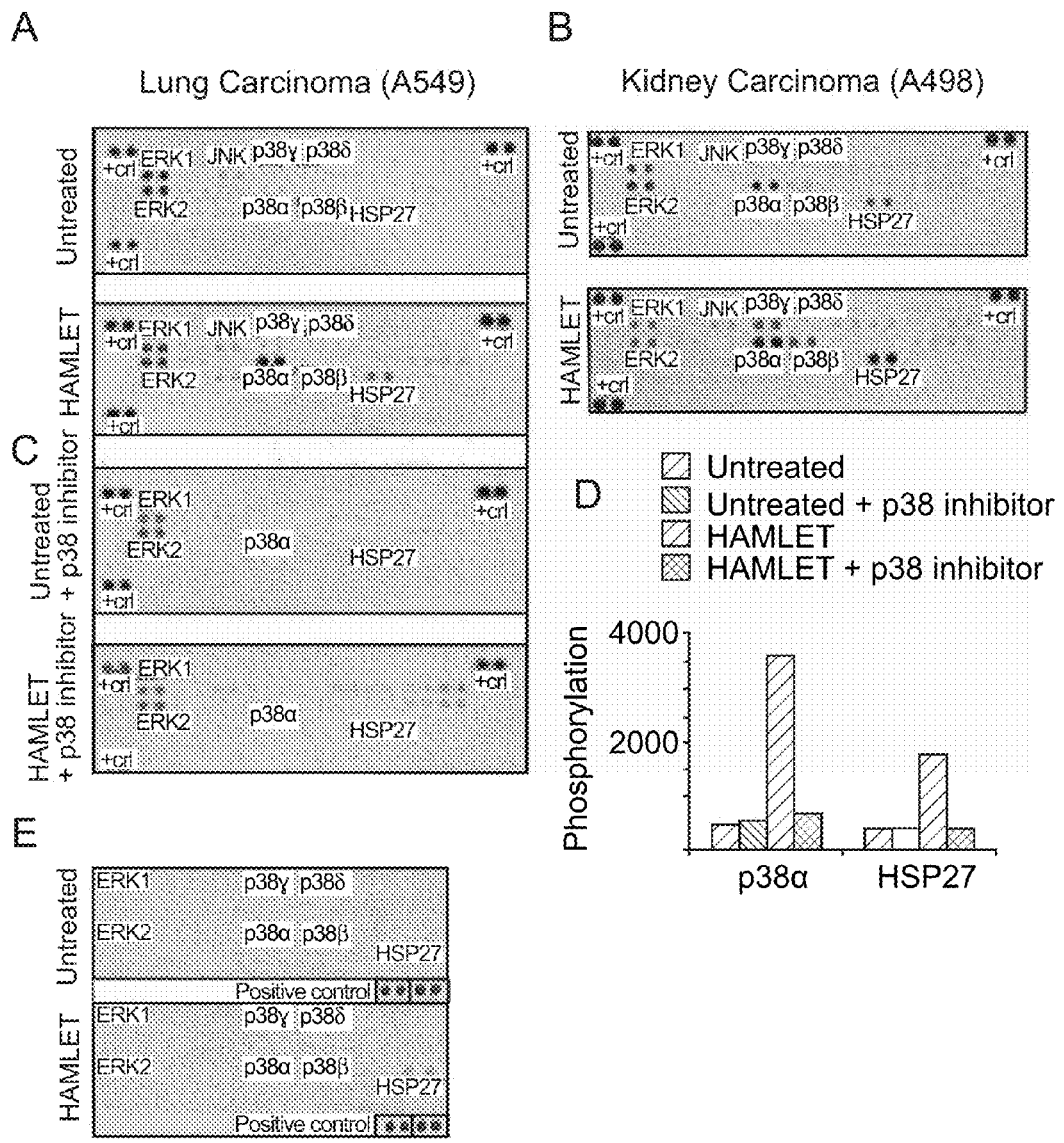

FIG. 11. MAPK phosphorylation in response to HAMLET.
(A) Lung carcinoma cells respond to HAMLET by phosphorylating p38α, p38β and p38γ as well as the downstream target HSP27. ERK1/2 were dephosphorylated. Lysates of cells exposed to HAMLET (35 μM) for 30 minutes. Membranes with phospho-specific antibodies were probed with protein lysates from HAMLET- or PBS-treated (control) carcinoma cells. Protein phosphorylation was quantified using ImageJ. Data are mean±SD. (B) Kidney carcinoma cells downregulate ERK1/2 and activate p38 in response to HAMLET. (C) p38 inhibition by SB202190 abrogates phosphorylation of p38 and HSP27. Cells were preincubated with SB202190 (20 μM, 30 minutes) and HAMLET-treated (35 μM, 30 minutes). (D) Healthy, differentiated cells do not activate p38 in response to HAMLET. Pediatric kidney cells in primary culture were treated with HAMLET (49 μM, 30 minutes).

Figure 12:
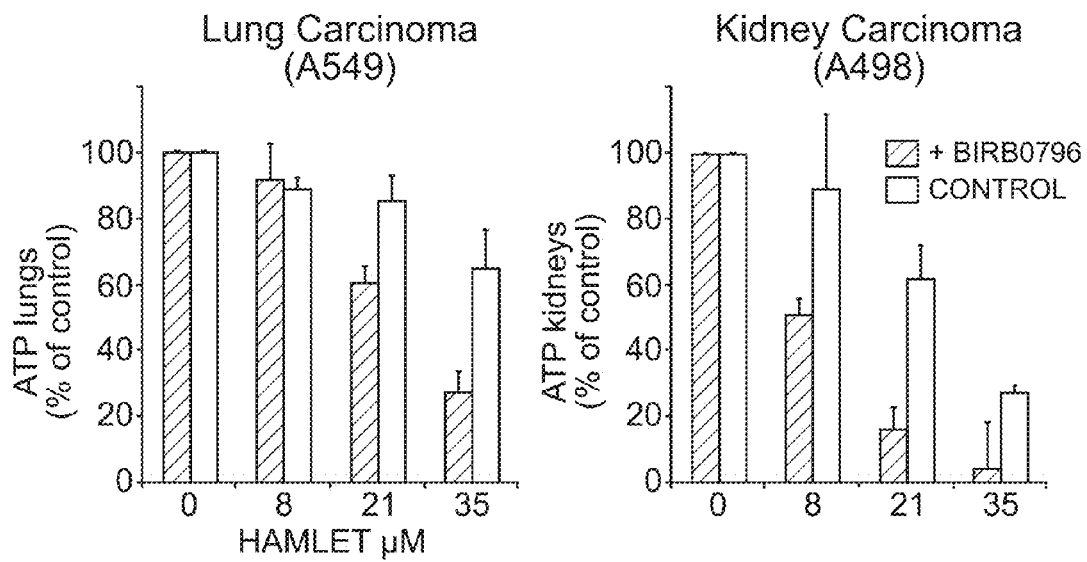
Figure 12:
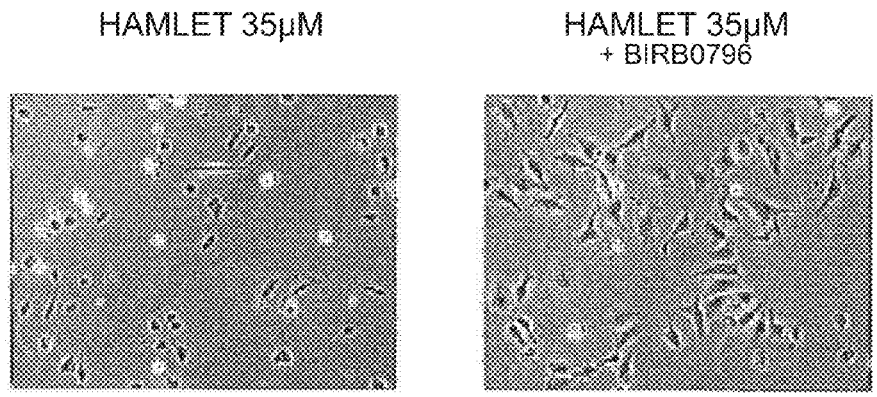

FIG. 12. BIRB796 rescues tumor cells from HAMLET induced cell death.
(A, B) p38 inhibition (BIRB796, 10 μM) rescued carcinoma (A549 and A498) cells from death in response to HAMLET (7-35 μM, 3 h). Viability was quantified by ATP levels. (B) BIRB796 (10 μM) diminishes the morphological changes associated with HAMLET induced cell death (35 μM, 3 h).

Figure 13:
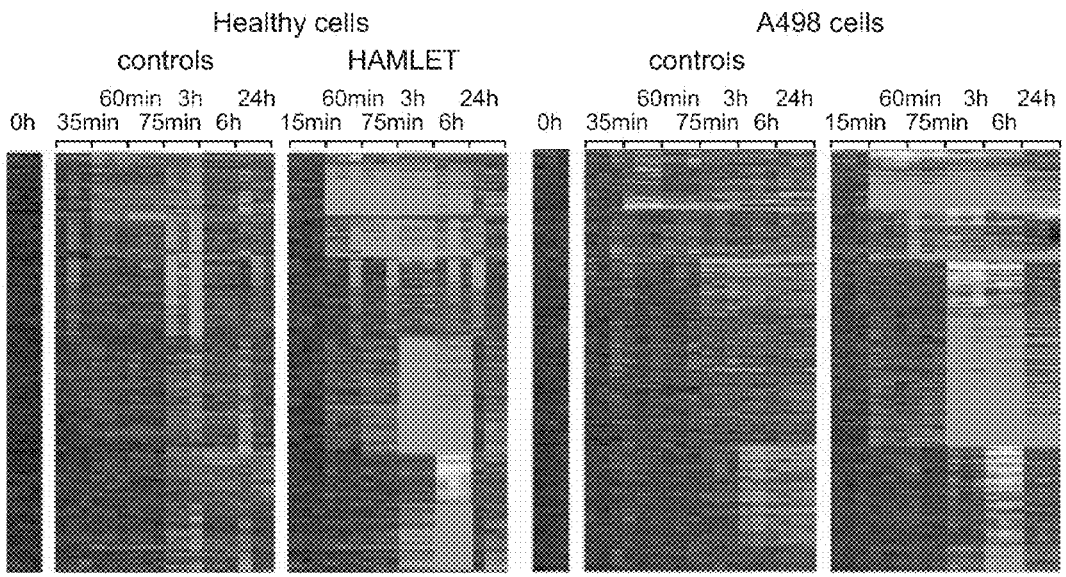
Figure 13:
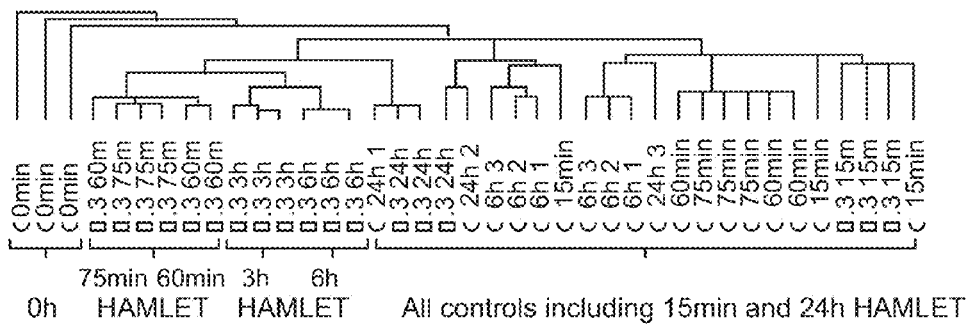
Figure 13:
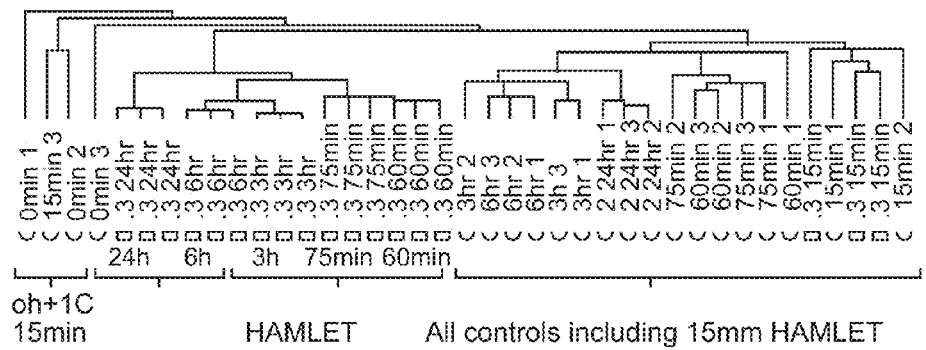

FIG. 13. Global transcriptional response in healthy, differentiated and tumor cells.
(A) Heat map of global transcriptional response in HAMLET-treated A498 kidney carcinoma cells and healthy kidney cells. Carcinoma cells showed a stronger induction of gene expression than the healthy cells. (B, C) Hierarchical clustering of all samples from healthy kidney cells and A498 kidney carcinoma cells, respectively. Healthy kidney cells showed a normalization of expression 24 hours after HAMLET exposure. This was not the case for A498 kidney carcinoma cells, where several pathways remained activated.

Figure 14A:
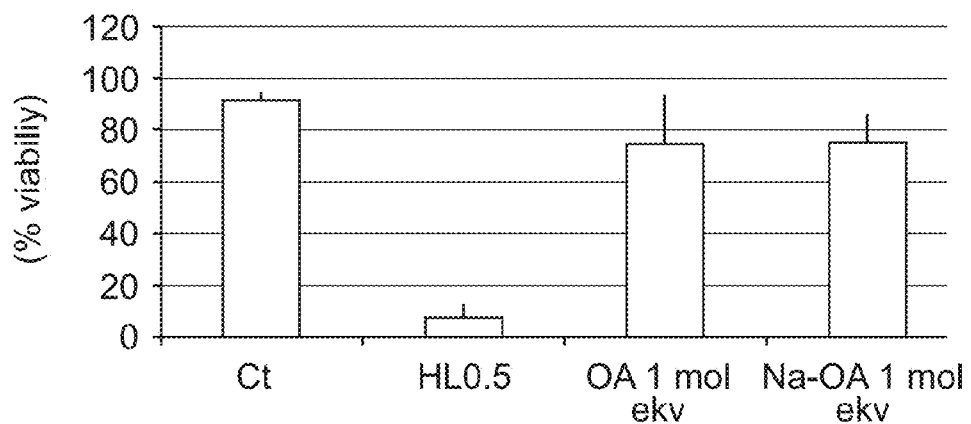
Figure 14B:
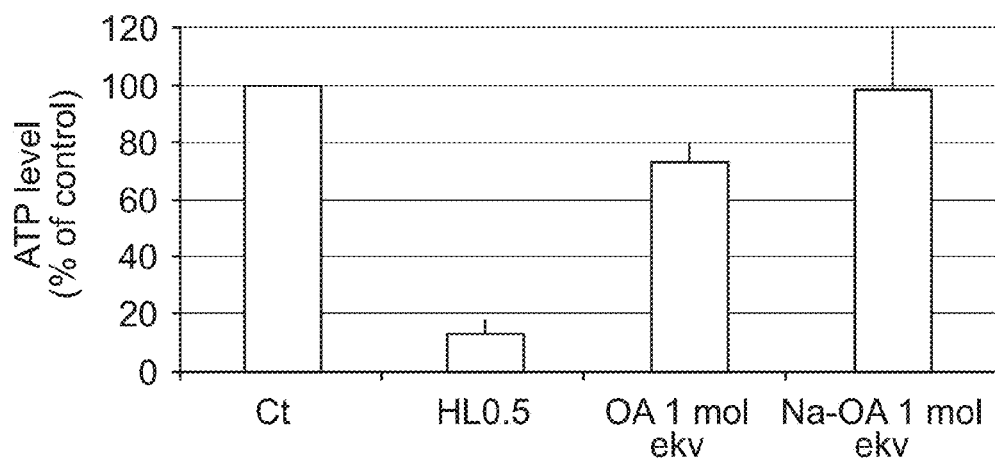

FIG. 14 is a series of graphs showing the results of a A549 cell death assay as described below, where FIG. 14A shows the results of a trypan blue viability test and FIG. 14B shows the results of an assessment of the ATP values, where Ct is the control, HL is HAMLET, OA is oleic acid and Na-OA represents sodium oleate.

Figure 15A:
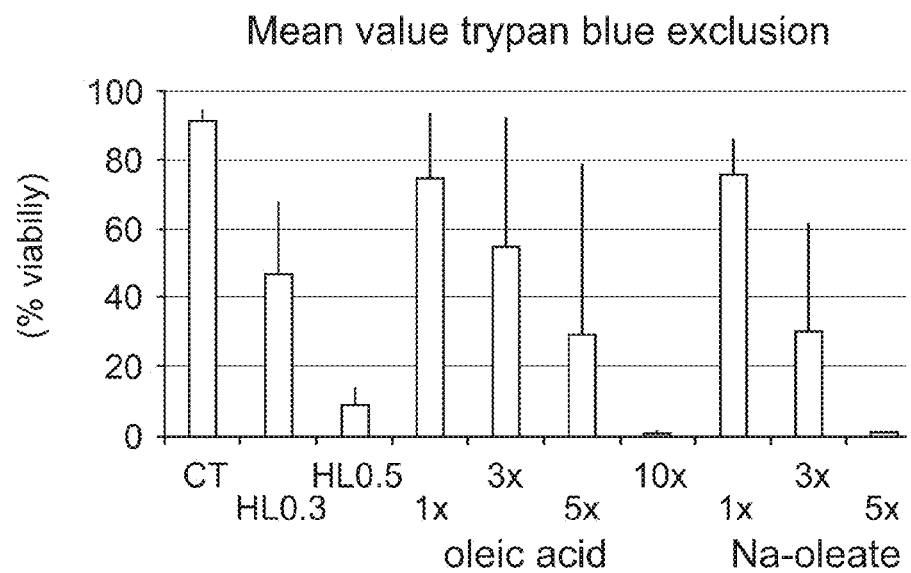
Figure 15B:
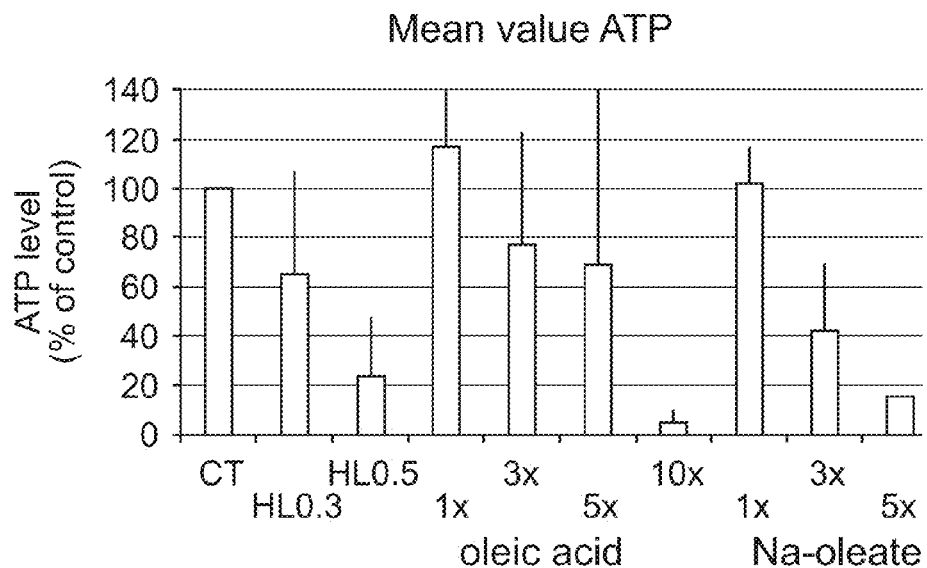

FIG. 15 is a series of graphs from a cell death assay similar to that associated with FIG. 14 but with a view to determining a dose response, where FIG. 15A shows the results of a trypan blue viability test and FIG. 15B shows the results of an assessment of the ATP values, where Ct is the control and HL is HAMLET.

Figure 16A:
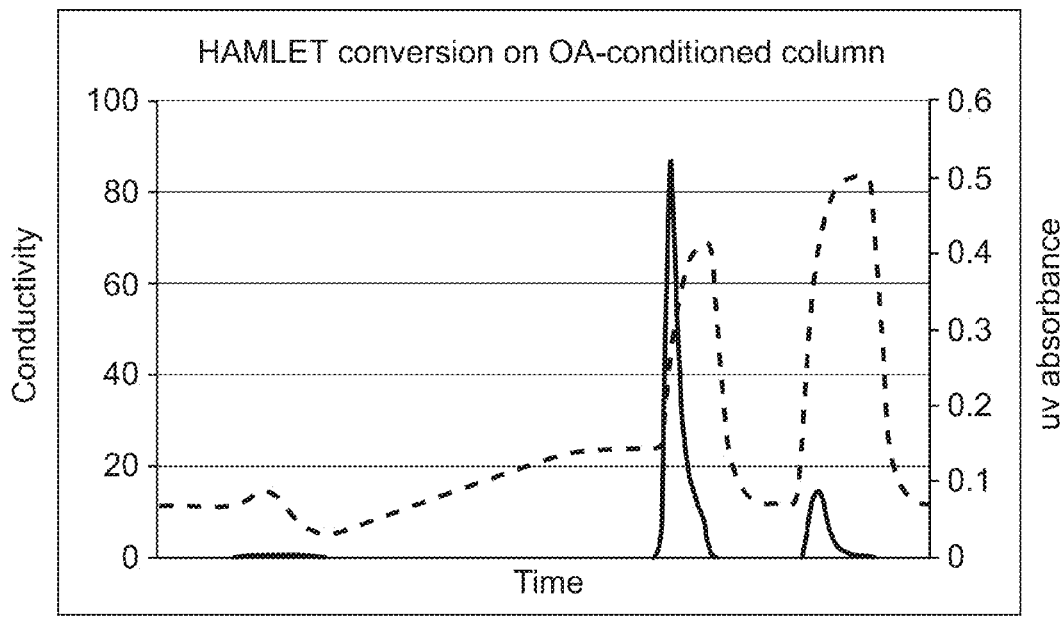
Figure 16B:
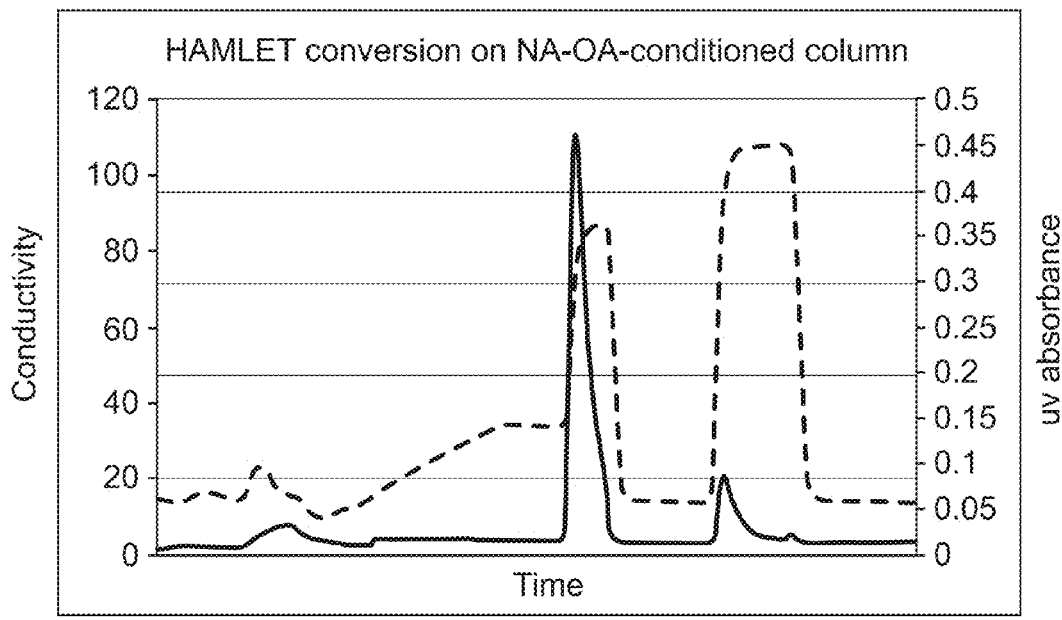

FIG. 16 shows the results of HAMLET production using columns conditioned with oleic acid (FIG. 16A) or sodium oleate (FIG. 16B).

Figure 17:
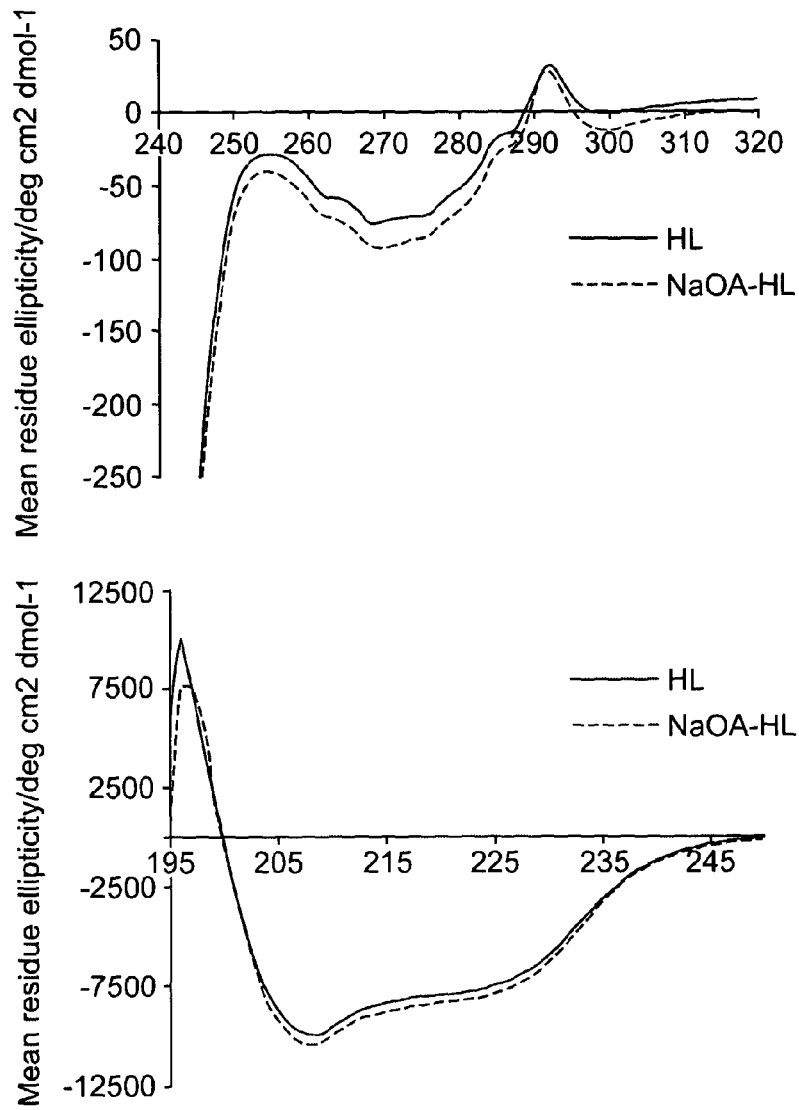

FIG. 17 shows the results of far- and near-UV CD spectra collected on HAMLET and NaOA-HAMLET.

Figure 18:
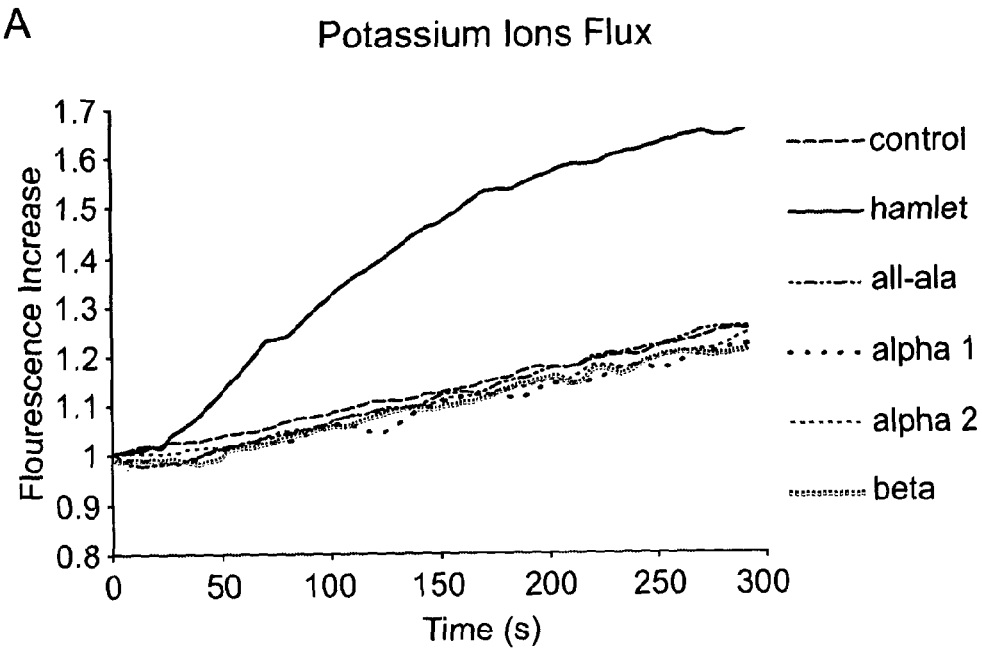
Figure 18:
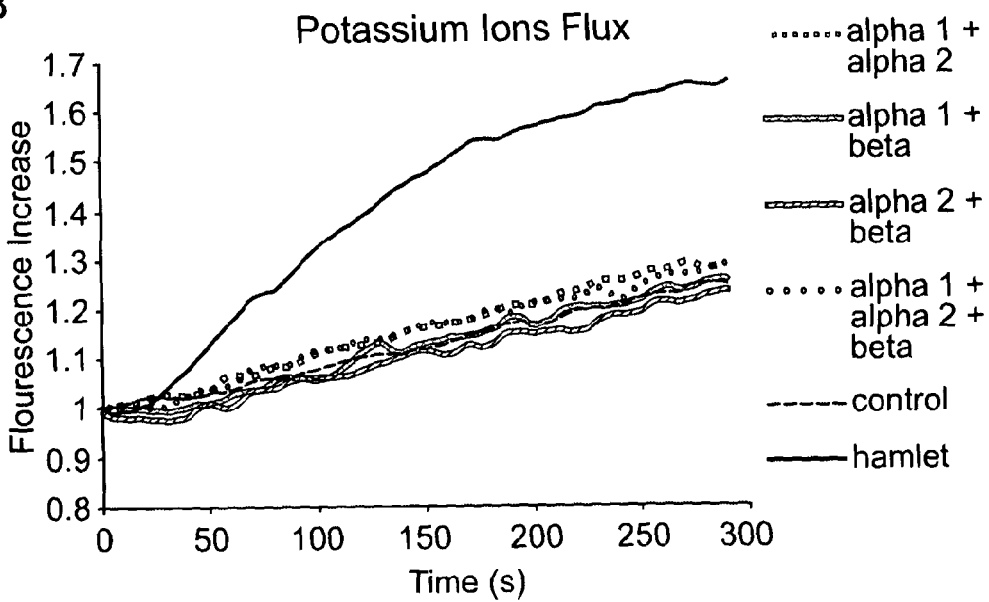
Figure 18:
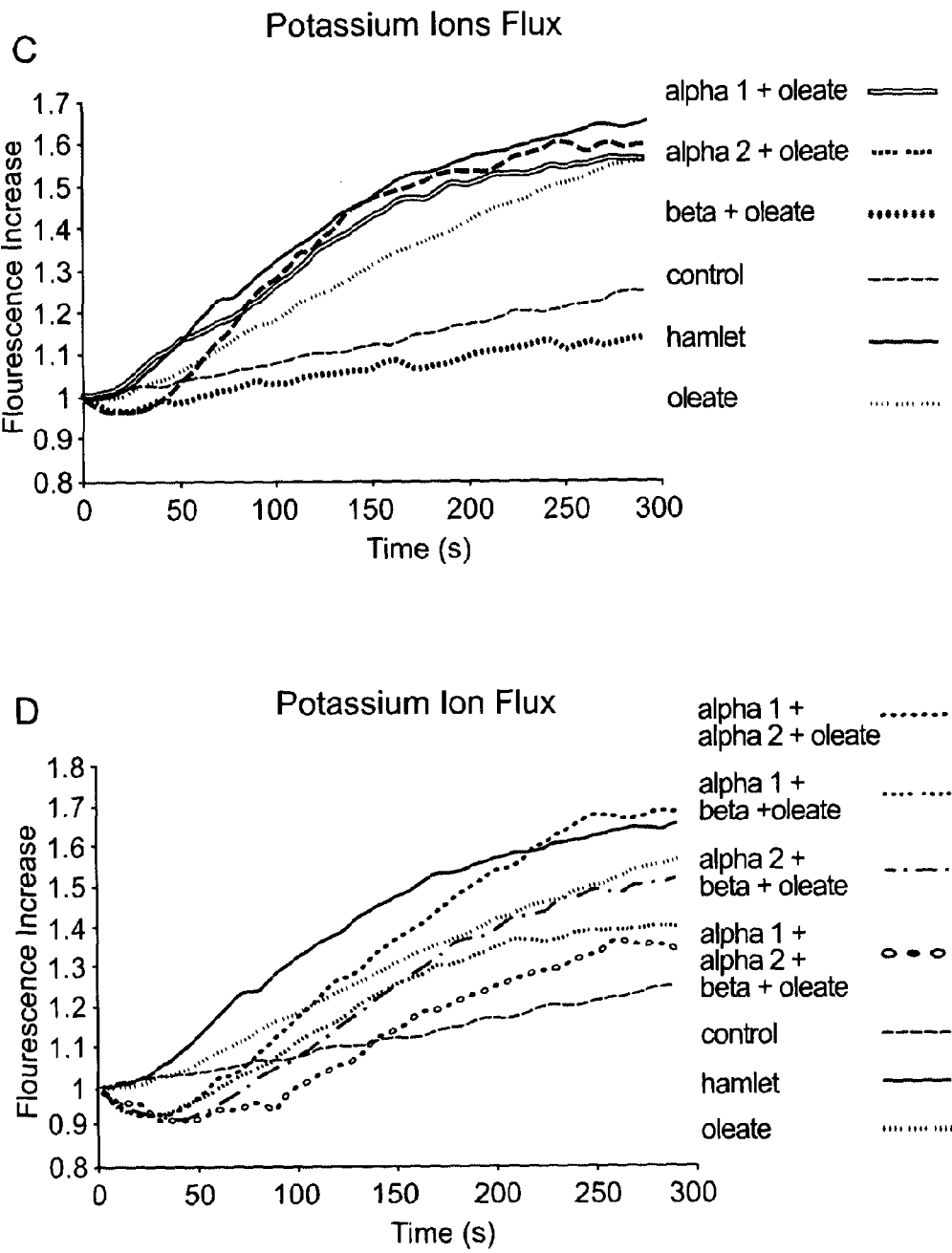

FIG. 18 shows the results of the studies on the impact of substances including complexes in accordance with the invention on potassium ion channels. (A) shows potassium channel activity in A549, lung carcinoma cell lines using Thallium (Tl$^+$) indicator when treated with HAMLET, a cysteine-free version of HAMLET (all-ala) and α-lactalbumin peptides where alpha 1 consisted of residues 1-40, beta consisted of residues 41-80, and alpha 2 consisted of residues 81-123) alone. (B) shows the results of a similar test carried out using mixtures of the peptides as indicated. (C) shows the results of a similar test carried out using the individual peptides combined with sodium oleate. (D) shows the results when mixtures of peptides together with oleate were used as compared to HAMLET and oleate alone.

Figure 19:
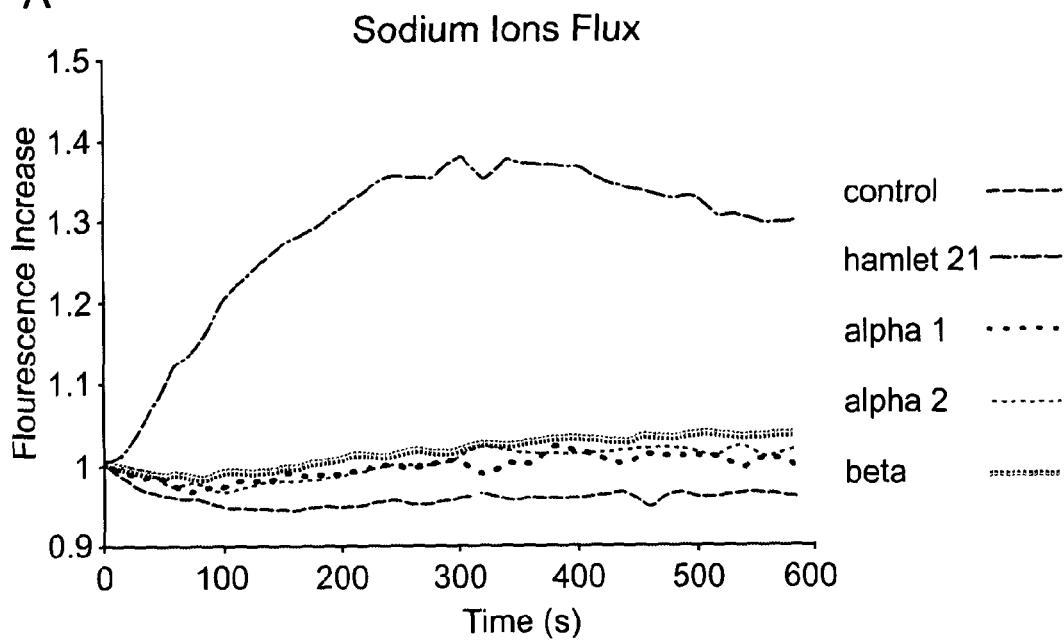
Figure 19:
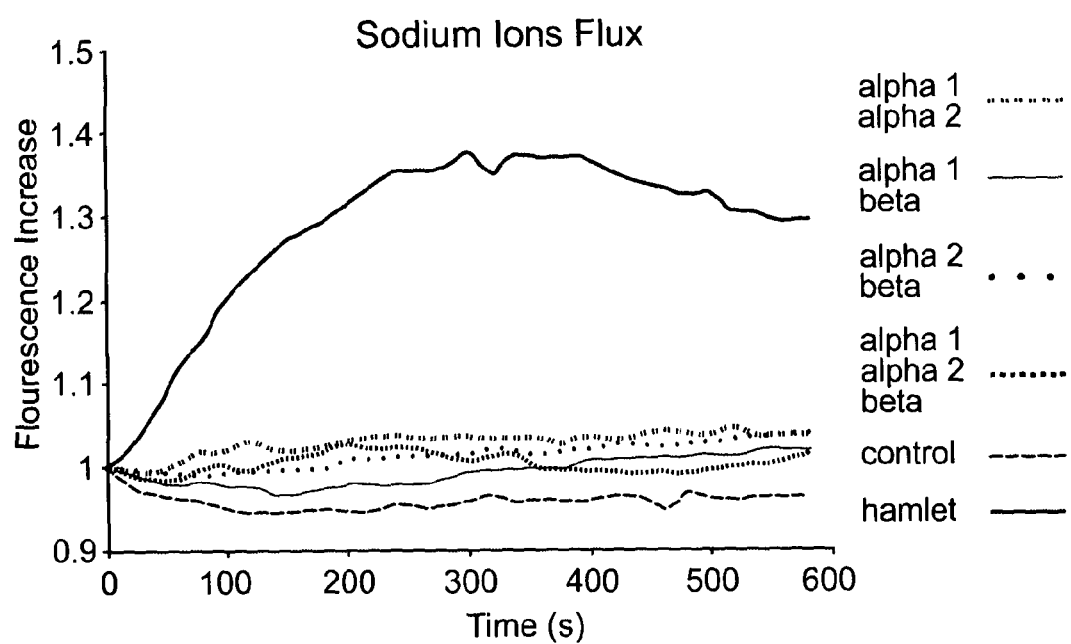
Figure 19:
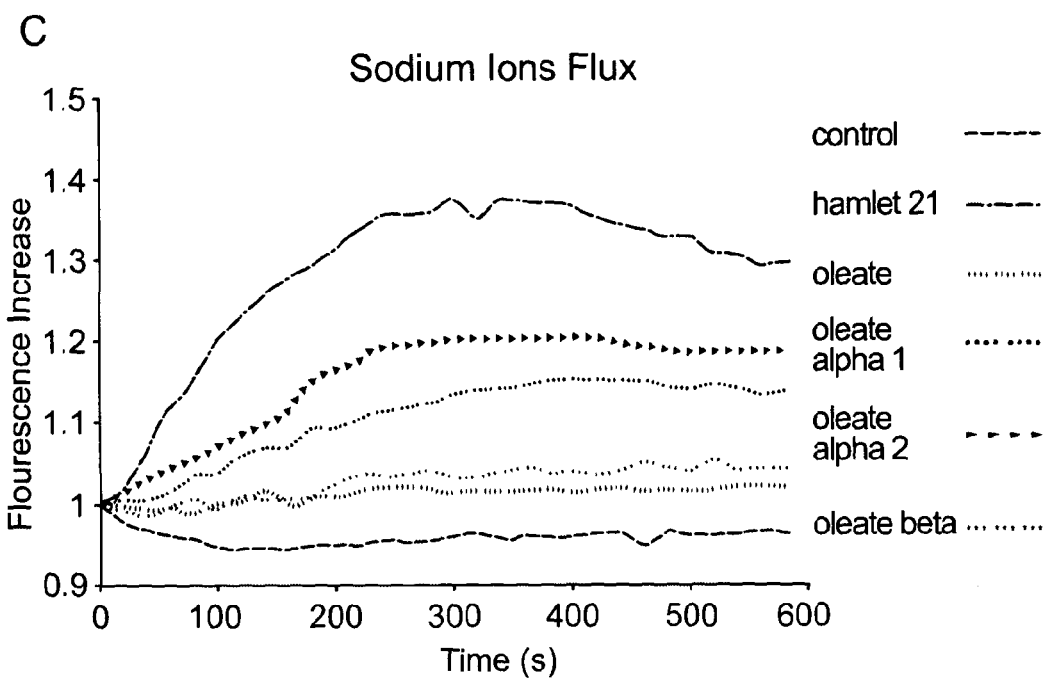
Figure 19:
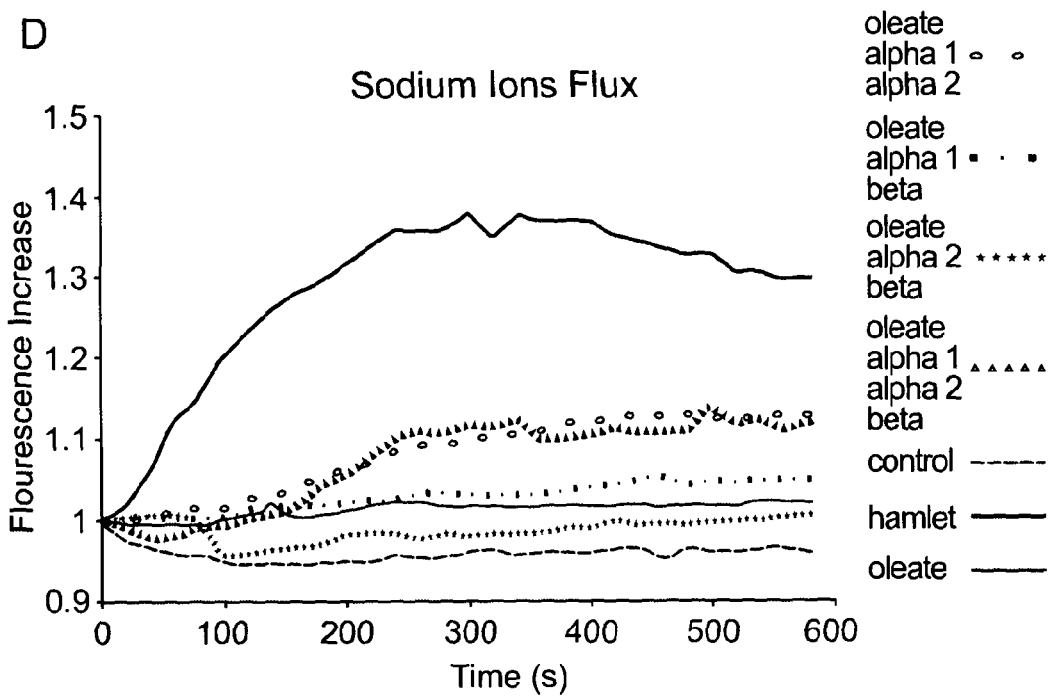

FIG. 19 shows the results of the studies on the impact of substances including complexes in accordance with the invention on sodium ion channels, wherein sodium influx in Jurkat cells was measured using CoroNa Green Sodium indicator as described below. (A) shows the results obtained when the cells were treated with the peptides alone. (B) shows the results obtained when mixtures of peptides were applied. (C) shows the results obtained with individual peptides combined with oleate. (D) shows the results obtained when mixtures of peptides together with oleate were used as compared to HAMLET.

Figure 20:
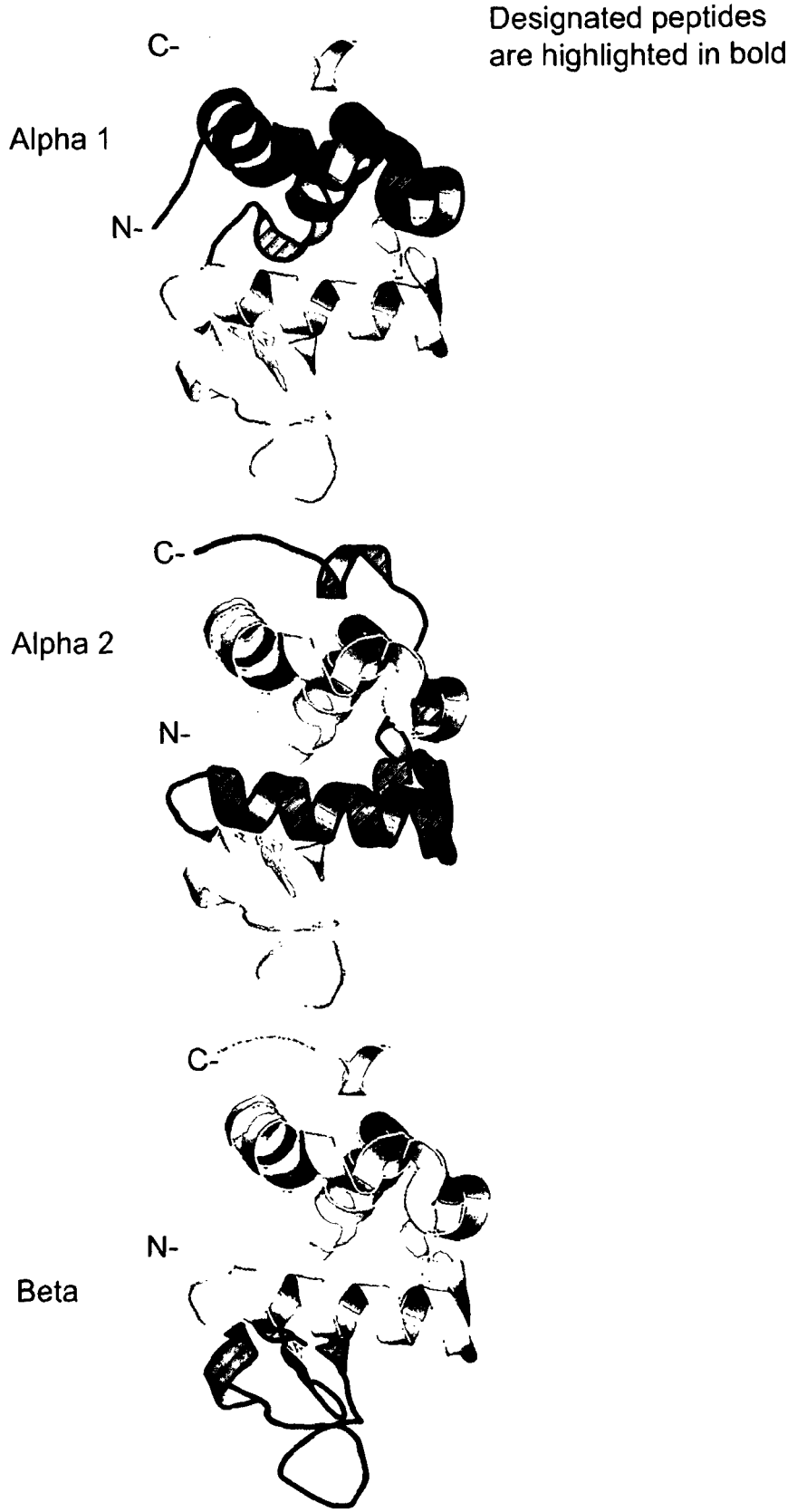

FIG. 20 shows the structure of alphalactalbumin with the individual domains highlighted.

Figure 21:
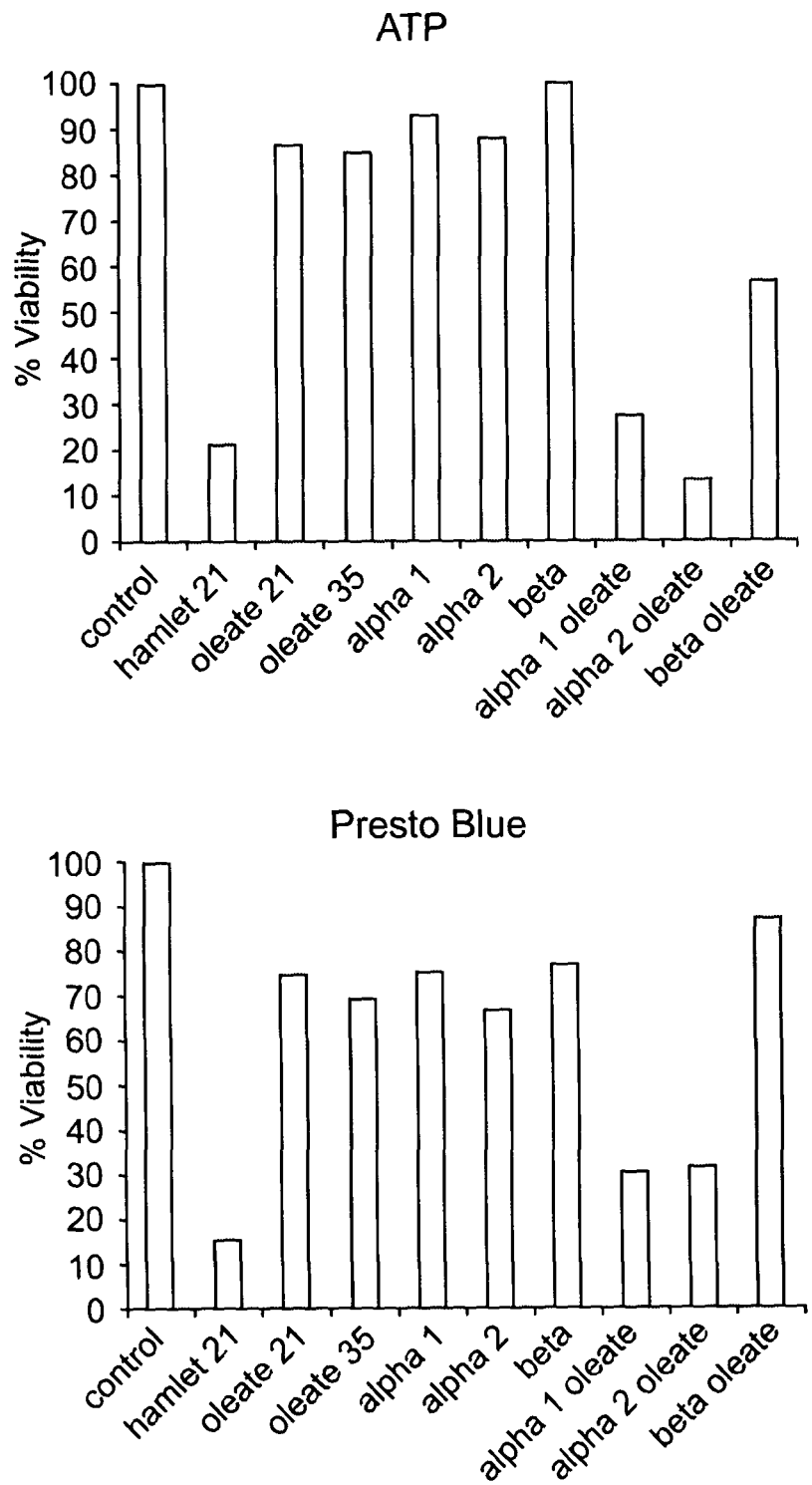

FIG. 21 shows the results of a cell death assay carried out on Jurkat cells and using various substances as specified in the Figure including complexes of the invention and components thereof, where the upper panel shows the results of a ATP viability test and the lower panel shows the results of a PrestoBlue viability test.

DETAILED DESCRIPTION OF THE INVENTION

Example 1

Materials and Methods
HAMLET Production

HAMLET was produced as previously described (Svensson et al., (2000). Proc Natl Acad Sci USA 97, 4221-4226). Native α-lactalbumin was purified from human milk by hydrophobic interaction chromatography. The protein was unfolded with EDTA, subjected to ion-exchange chromatography on a matrix pre-conditioned with oleic acid and eluted with high salt. HAMLET was lyophilized after purification.
Cells T-cell lymphoma cells (Jurkat), lung (A549), ovarian (HeLa) and kidney (A498) carcinoma cells (ATCC) were cultured in RPMI-1640 with non-essential amino acids (1:100), 1 mM sodium pyruvate, 50 µg/ml, gentamicin (Gibco), and 5% (A549 and A498) or 10% (HeLa and Jurkat) fetal calf serum (FCS), respectively. Human renal epithelial cells (HRTEC) were kindly provided by Dr. Diana Karpman (Lund University, Lund, Sweden) and cultured in DMEM/F12 with 15% FCS (Karpman et al., 1998, Infection and Immunity 66: 636-644). IRB approval was obtained from the Medical Ethics Committee of the Lund University Medical Faculty, Lund, Sweden (decision number LU 456-96). Primary RPTEC cells (human renal proximal tubule epithelial cells) were purchased from Lonza and cultured in DMEM-F12 supplemented with NEAA, sodium pyruvate, gentamicin, glutamax and 15% FBS (Gibco).
Ion Fluxes The FLUXOR™ potassium ($K^+$) channel assay was performed on the TECAN infinite F200 (Tecan Group, Switzerland), according to the manufacturer's instructions (Invitrogen). Briefly, this involved FLUXOR™ loading buffer (Hank's Balanced Saline Solution, (HBSS) buffered with 20 mM HEPES and pH adjusted to 7.4 with NaOH. POWERLOAD™ concentrate and water-soluble Probenecid were used respectively to enhance the dye solubility and retention, respectively. Media were removed from the cell plates manually, and 80 µL of loading buffer containing the FLUXOR™ dye mix was applied to each well. Once inside the cell, the nonfluorescent AM ester form of the FLUXOR™ dye is cleaved by endogenous esterases into a thallium-sensitive indicator. The dye was loaded for 60 minutes at room temperature and then removed with the supernatant. After washing with dye-free PBS buffer, a final volume of 80 µL assay buffer containing water-soluble probenecid was added. Cells received one of the following channel inhibitors: 3.3 µL per well of 30 mM amiloride, 3.0 µL of 32 mM $BaCl_2$, 1.8 µL of 5.4 mM gadolinium, 3 µL 3.2 mM tetrandrine and 2.3 µL of 2.6 mM ruthenium red, and were then incubated at room temperature (23-25° C.) for 30 minutes to allow equilibration of the test compounds. Prior to injection, stimulation buffer was prepared from the chloride-free buffer and thallium reagents provided in the kit as well as HAMLET, to achieve a final added concentrations of 2 mM free TI+ and 35 µM HAMLET after 1:5 dilution upon injection of the stimulus buffer onto cells that had been loaded with FLUXOR™ dye.
Cell Death Assay Cells were detached from cell culture flasks with versen (0.2 g EDTA in 200 ml $H_2O$ and 800 ml PBS), washed with PBS and resuspended in serum-free RPMI-1640. HAMLET dissolved in PBS was incubated with cells ($0.5×10^6$/ml for A549, A498 and HeLa cells; $1×10^6$/ml for Jurkat) at 37° C. FCS was added after 1 hour. Cell death was quantified by trypan blue exclusion (Chroma Gesellschaft Schmid & Co) or by measuring ATP levels (ATPlite Kit, PerkinElmer, Infinite 200, Tecan). Light images were captured using the HOLOMONITOR™ M2 digital holographic microscope (Phase Holographic Imaging AB, Lund, Sweden).
Inhibitors and RNAi For studies with inhibitors, cells were pretreated for 30 minutes. Inhibitors used were Gadolinium chloride ($GdCl_3$, 100 µM), Barium chloride ($BaCl_2$, 1 mM), Ruthenium red (30 µM), tetrandrine (10 µM) and amiloride (1 mM), all from Sigma Aldrich. For p38 inhibition, SB202190 (20 µM, Sigma Aldrich) or BIRB796 (10 µM, Axon Medchem) dissolved in DMSO was used. The wells were washed twice with PBS and new medium with inhibitor was added. For RNA interference, FlexiTube siRNA Premixes against MAPK11 (SI00606053), MAPK14 (SI00300769) and All Star Negative Control siRNA (SI03650318) from Qiagen was used. A549 forward was transfected using 25 nM final siRNA concentration in 24-well plate. After 48 hours, knockdown was examined by Western blot (anti-p38, 1:1000, Cell Signalling) and RT-PCR (MAPK14, QT00079345, QIAGEN).
RT-PCR and XBP1 Splicing RNA was prepared with the RNeasy Mini Kit (QIAGEN, Hilden, Germany) and treated with DNAse I (QIAGEN). cDNA was synthesized using the Superscript III first strand RT-PCR system (Invitrogen). PCR of spliced and un-spliced XBP1 was as described (Yoshida et al., 2001 Cell 107: 881-891). Real-time PCR was performed on a Rotorgene 2000 instrument (Corbett Life Science, Sydney, Australia) using TaqMan Gene Expression Assays (Applied BioSystems) CHOP/DDIT3 (Hs01090850), IL6 (Hs00985639), IL8 (Hs00174103) and TNFα (Hs00174128). GAPDH (Hs99999905_m1) was used for normalization.
Live Cell Imaging For live cell imaging, cells were pre-treated with SB202190 for 30 minutes, nuclei were stained with Hoechst 33342 (Invitrogen) and Alexa-Fluor 568-labeled HAMLET (10% labeled HAMLET, Molecular Probes) was added in serum-free medium. FCS was added after 1 hour. Fluorescence was detected with pinhole settings corresponding to 1 airy unit. The cells were kept at 37° C., 5% $CO_2$ and examined unfixed by LSM510 DUO confocal microscopy (Carl Zeiss).
Western Blot and Cytokine Quantification Equal volumes of lysates were separated by SDS-PAGE on 4-12% Bis-Tris gels (Invitrogen) and blotted onto PVDF membranes. For other Western blots, 200,000 cells were allowed to adhere overnight in a 6-well plate. After HAMLET treatment the cells were washed with PBS and lysed in M-PER lysis buffer (Pierce) containing Complete protease inhibitor cocktail and PhosSTOP phosphatase inhibitor cocktail (both from Roche). The detached cells were collected by centrifugation. The lysates were cleared by centrifugation and protein concentrations were measured using the DC Protein Assay (Bio-Rad Laboratories, Hercules, Calif.). Equal amounts of protein were separated by SDS-PAGE on 4-12% Bis-Tris gels (Invitrogen) and blotted onto PVDF membranes (GE Healthcare). Membranes were saturated with BSA (GAPDH) or nonfat dry milk (phospho-p38, p38, phospho-ERK1/2, ERK1/2) and incubated with anti-p38, anti-phospho-p38, anti-ERK1/2, anti-phospho-(Thr202/Tyr204)-p44/42 (all 1:500-1000, Cell Signaling Technology), anti-ATF6 (1:1000, IMG-273, Imgenex), anti-phospho-eIF2a (Ser51), (1:500, Cell Signaling Technology) or anti-GAPDH (1:3000-5000, Novus Biologicals) antibodies followed by horseradish peroxidase-conjugated anti-rabbit (1:1000, DakoCytomation, Glostrup, Denmark) or anti-mouse (1:40000-50000, Novus Biologicals) antibodies for staining. Bound antibodies were detected with ECL Plus Western Blotting Reagent (GE Healthcare, Little Chalfont, UK) and GelDoc equipment (Bio-Rad Laboratories, Hercules, Calif.). If required, membranes were stripped with Restore Western Blot Stripping Buffer (Pierce, Rockford, Ill.), blocked and reprobed with new antibodies. MAP kinase phosphorylation was analyzed on a Human Phospho-MAPK array (Proteome Profiler Array, R&D Systems) as per the manufacturer's instruction. Band and spot intensities were quantified using ImageJ (Abramoff et al., July 2004, Biophotonics International). Cytokine quantification (IL6, IL8, TNFα) was performed on an IMMULITE 1000 immunoassay system (Siemens Diagnostics).

Transcriptomics

For the microarray analysis with ion channel inhibitors, 200,000 A549 cells/well were allowed to adhere overnight on a 6-well plate. After 1 hour of HAMLET treatment, the cells were lysed and RNA was extracted using the RNeasy Mini Kit (QIAGEN). The samples were sent to AROS Applied Biotechnology (Århus, Denmark) for analysis. Data was preprocessed using RMA implemented in the free software packages "affy" as provided by R and Bioconductor (<www.r-project.org>). Differentially expressed genes were identified using empirically Bayes adjusted t-statistics and characterized using the Functional Annotation Clustering Tool in the Database for Annotation, Visualization and Integrated Discovery (DAVID), (Dennis et al., 2003 Genome Biology 4(5): P3) and Ingenuity Pathway Analysis (Ingenuity Systems). All microarray data were registered into NCBI's Gene Expression Omnibus (GEO) database (<www.ncbi.nlm.nih.gov/projects/geo>) with accession numbers GSE23772.

For the extended microarray analysis, gene expression was assessed by whole genome Illumina microarrays (HumanHT-12 Expression BeadChip). Data was normalized using cross-correlation (Chua et al., 2006 Nucleic Acids Research 34: e38). Genes with a log 2 fold change ≥1.2 in tumor cells and ≥2.0 in healthy, differentiated cells at any time point were regarded as differentially expressed (Benjamini-Hochberg adjusted p-value <0.05).

Statistical Analysis

Repeated measures ANOVA was performed with InStat software (version 3.06, GraphPad, San Diego, Calif.).

Results

Ion Channel Activation by HAMLET; Difference Between Carcinoma Cells and Normal, Differentiated Cells.

Figure 1:
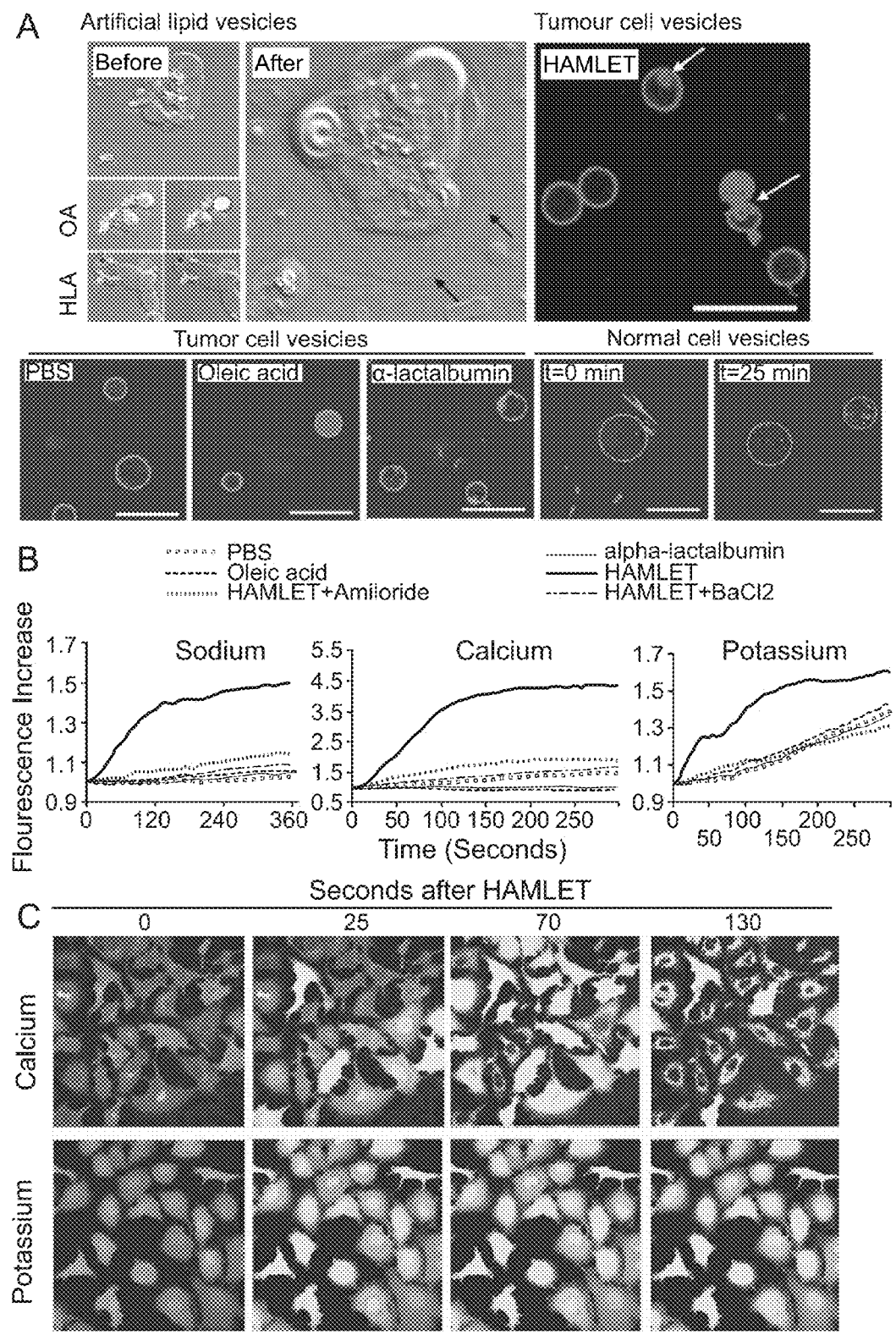
FIG. 1. HAMLET alters the morphology of lipid vesicles by membrane elongation and induces ion fluxes in tumor cells.
(A, upper panels) Bright-field micrographs showing glass-adherent egg yolk vesicles before and after a 40-minute exposure to HAMLET, α-lactalbumin (HLA) or oleic acid (OA). Morphology was recorded by differential interference contrast microscopy. Scale bar 20 μM. At T=0, the vesicles were rigid, with predominantly rounded morphology. Following HAMLET exposure, unilamellar structures were more prominent and the membranes were elongated (see black arrows). The morphology of vesicles treated with HLA or OA was unchanged. (A, Lower panels) Effect of HAMLET on PMVs from lung carcinoma cells. PMVs on glass-bottom dishes were exposed to HAMLET, HLA or OA and stained with Nile red for confocal microscopy. Following HAMLET exposure, membrane invaginations were detected in tumor cells but not in normal, differentiated cells. As a control PMVs from healthy, differentiated cells on glass-bottom dishes were also exposed to HAMLET and stained with Nile red. No changes in membrane composition were detected. (B) By flourometry, the fluxes of $Ca^{2+}$, $K^+$ and $Na^+$ were shown to be HAMLET specific, as PBS, α-lactalbumin or oleic acid had no effect. Amiloride or $BaCl_2$ inhibited the $Ca^{2+}$ fluxes. For effects of other ion channel inhibitors, see FIG. 8. (C) HAMLET triggers $K^+$ and $Ca^{2+}$ fluxes, visualized by real time confocal imaging of lung carcinoma cells, loaded with the $Ca^{2+}$ fluorophore Fluo-4 AM or the $K^+$ fluorophore FLUXOR™.

To examine if HAMLET modulates ion channel activity in tumor cells, we first quantified changes in intracellular $Ca^{2+}$ and K. Lung carcinoma cells were first preloaded with the Fluo-4 $Ca^{2+}$ fluorophore Fluo-, exposed to HAMLET (35 μM) and examined by real time confocal microscopy for changes in fluorescence intensity (FIG. 1A). The $Ca^{2+}$ ionophore A23187, which acts as a $Ca^{2+}$ shuttle across cell membranes, was used as a positive control (Abbott et al., 1979 Antimicrobial Agents and Chemotherapy 16, 808-812).

HAMLET triggered a rapid, step-wise increase in intracellular $Ca^{2+}$ (FIG. 1A), starting after about 30 seconds, with a second peak after about 100 seconds, but with considerable heterogeneity. The ionophore caused a more drastic and sustained increase in intracellular $Ca^{2+}$ levels than HAMLET (31% of the ionophore, FIG. 1B) and involved all cells compared to about 50% of the cells exposed to HAMLET. The ionophore also triggered immediate changes in carcinoma cell morphology indicating membrane rupture and necrosis (FIG. 1B). The morphological changes in HAMLET-treated cells occurred more gradually and with different characteristics implying that the initial membrane perturbation mechanism differs between HAMLET and the ionophore. To distinguish $Ca^{2+}$ mobilization from intracellular stores from the influx of extracellular $Ca^{2+}$, EGTA was then added to the cell medium. The early increase in intracellular $Ca^{2+}$ in response to HAMLET (35 μM) was insensitive to EGTA, but the subsequent $Ca^{2+}$ response was inhibited by EGTA, as was the response to the ionophore (Table 1), suggesting that HAMLET triggers $Ca^{2+}$ release from intracellular stores, followed by opening of ion channels. $K^+$ fluxes across tumor cell membranes were subsequently quantified under the same experimental conditions, using the fluorophore FluxOR™, which fluoresces after thallium has entered cells through $K^+$ channels. HAMLET rapidly opened the $K^+$ channels in carcinoma cells (FIG. 1D).

Changes in $Ca^{2+}$ and $K^+$ levels were subsequently examined in healthy, differentiated cells in primary culture, previously shown to survive HAMLET challenge (Hakansson et al., 1995; Svanborg et al., 2003 Advances in Cancer Research 88: 1-29). Human renal tubular epithelial cells (HRTEC) were preincubated with Fluo-4 as described, exposed to HAMLET (35 μM) and examined by real time confocal microscopy. HAMLET mobilized a weak and transient $Ca^{2+}$ response in HRTECs, which lasted for about 90 seconds compared to the prolonged response to HAMLET in carcinoma cells (p<0.00, FIG. 1C) and was insensitive to EGTA treatment, revealing that $Ca^{2+}$ can be mobilized from intracellular stores by HAMLET also in healthy cells but that the subsequent effects on ion channels are weak or absent (FIG. 1D). No change in morphology was observed, but the $Ca^{2+}$ ionophore, gave rise to a rapid and sustained increase in $Ca^{2+}$ and a rapid change of morphology occurred, with necrotic characteristics, demonstrating that this response was intact in healthy cells, if properly stimulated.

The results, especially the prolonged $Ca^{2+}$ response and the magnitude of $K^+$ channel activation, suggest that ion channel activation by HAMLET distinguishes carcinoma cells from healthy, differentiated cells.

Ion Channel Inhibitors Modify $Ca^{2+}$ and $K^+$ Fluxes in Response to HAMLET.

To further characterize ion channel activation by HAMLET, carcinoma cells were pretreated with defined channel blockers. Amiloride is a sodium channel inhibitor with effects on mechanosensitive channels, barium chloride ($BaCl_2$) is a general $K^+$ channel inhibitor, gadolinium chloride ($GdCl_3$) inhibits mechanosensitive channels, Ruthenium red is a general $Ca^{2+}$ inhibitor and tetrandrine inhibits large conductance, $Ca^{2+}$ activated $K^+$ channels. The carcinoma cells were preincubated with Fluo-4 as described above, pretreated with each of the channel inhibitors for 30 minutes, exposed to HAMLET (35 μM) and examined by real time confocal imaging. Furthermore, cells treated with EGTA were compared to cells with intact extracellular $Ca^{2+}$ levels, to distinguish the early peak from the subsequent influx of $Ca^{2+}$ (FIG. 1B, Table in FIG. 8).

The first, EGTA insensitive $Ca^{2+}$ peak in carcinoma cells was inhibited by amiloride, $BaCl_2$ and $GdCl_3$, illustrating an effect of HAMLET on both mechanosensitive and voltage gated channels in carcinoma cells. The $K^+$ flux was strongly inhibited by $GdCl_3$, implying that mechanosensitive channels might be involved (FIG. 1E), while amiloride and $BaCl_2$ gave intermediate inhibition. In healthy cells, $GdCl_3$ had no effect on the healthy cells, however, indicating a difference in mechanosensing between carcinoma cells and healthy, differentiated cells. the low $K^+$ signal after HAMLET challenge was further reduced by the channel blockers (FIG. 1E).

These results show that HAMLET activates $Ca^{2+}$ and $K^+$ channels, preferentially in carcinoma cells, implying that opening of the $Ca^{2+}$ and $K^+$ channels might be an essential component of carcinoma cell responses to HAMLET. Inhibition of $K^+$ channels by $BaCl_2$ and of $Ca^{2+}$ channels by Ruthenium red and tetrandrine showed that these channels are activated together. The inhibitory effects of amilioride and $GdCl_3$ suggested that MSCs might be perturbed by HAMLET, in addition to $Ca^{2+}$ dependent $K^+$ channels.

Ion Channel Inhibition Prevents HAMLET-Induced Cell Death.

Figure 2:
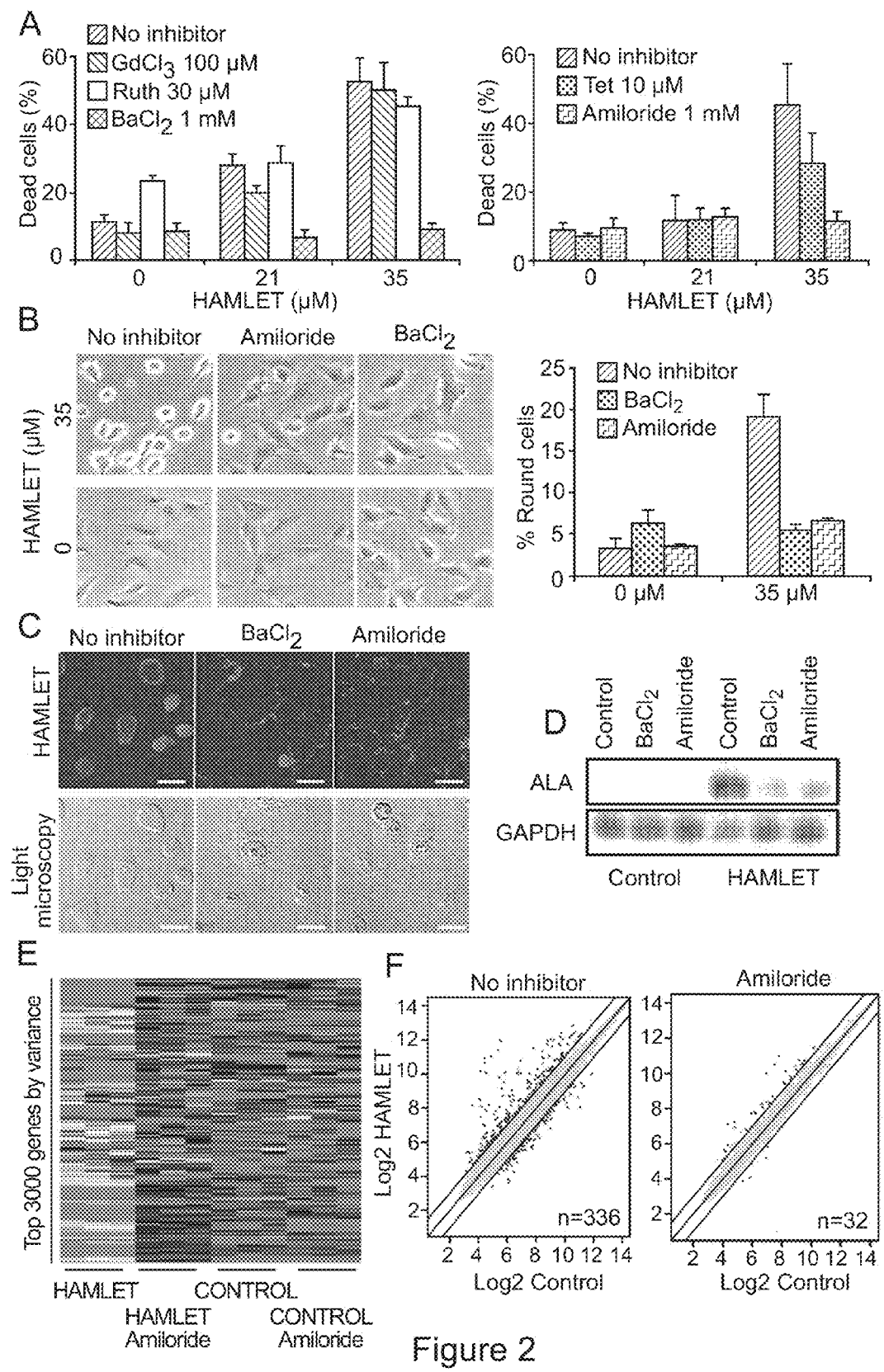
FIG. 2. Ion channel inhibitors rescue carcinoma cells from death and block HAMLET uptake and morphologic change.
(A) Viability of lung carcinoma cells after exposure to HAMLET (21 or 35 μM, 3 h), quantified by trypan blue exclusion. The tumoricidal effect of HAMLET was inhibited by amiloride or $BaCl_2$ but $GdCl_3$, Ruthenium Red and tetrandrine showed no effect (means+SEMs, two to three experiments). (B) $BaCl_2$ and amiloride prevented carcinoma cells from changing their morphology in response to HAMLET (Mean of two images in one experiment+SEMs). (C) Internalization of Alexa-fluor labeled HAMLET by tumor cells (35 μM, 1 hour), visualized by confocal microscopy. Amiloride or $BaCl_2$ inhibited internalization, leaving HAMLET associated with the cell surface. (D) Western blot of cell lysates confirming the reduction in cell-associated HAMLET by amiloride and $BaCl_2$ (35 μM, 1 hour, detected with anti-α-lactalbumin antibodies). GAPDH was the loading control. (E) The transcriptomic response to HAMLET requires functional ion channels. Amiloride markedly reduced the global transcriptional response to HAMLET in lung carcinoma cells. (F) The number of differentially expressed genes (log 2 fold change >1 and FDR-adjusted p-value <0.05) was greatly reduced by amiloride.

To examine if functional ion channels are important for the tumoricidal activity of HAMLET, A549 lung carcinoma cells in suspension were pretreated with the channel inhibitors for 30 minutes and exposed to increasing concentrations of HAMLET for three hours. In the absence of inhibitors, a rapid, dose-dependent lethal response to HAMLET was detected, as measured by trypan blue exclusion (FIG. 2A, B) and ATP levels (FIG. 2A, B). Amiloride and $BaCl_2$ markedly reduced cell death, but $GdCl_3$, Ruthenium red and tetrandrine had no effect on viability. The rescue effect of amiloride and $BaCl_2$ was confirmed in ovarian carcinoma cells (HeLa cells) and lymphoma cells (Jurkat cells), under the conditions described above (FIGS. 9 and 10). The inhibitors showed similar efficacy as observed in lung carcinoma cells, implying that perturbations of ion channels might occur broadly in carcinoma and lymphoma cells, in response to HAMLET. The rescue effect of amiloride and $BaCl_2$ was sustained in carcinoma cells for 24 hours, when 44% of the control cells had died, while cells pretreated with $BaCl_2$ or amiloride were still viable (13 and 8%, respectively, FIG. 11). The rescue effect and the difference in activity between the inhibitors was similar for adherent cells and cells in suspension exposed to HAMLET (21 and 35 µM) for 3 hours, suggesting that extracellular matrix interactions were not directly involved in the death response (FIGS. 2C and 9).

To examine if the HAMLET-induced change in carcinoma cell morphology was modified by the channel inhibitors, lung carcinoma, kidney carcinoma and lymphoma cells were exposed to HAMLET in the presence or absence of ion channel inhibitors and examined by light microscopy (FIG. 2C and Supplemental fig). After pretreatment with amiloride or $BaCl_2$, carcinoma cells maintained their normal morphology. In contrast, $GdCl_3$, Ruthenium red or tetrandrine did not prevent the morphological changes in response to HAMLET.

The above results demonstrate that ion channel activation is essential for the tumoricidal response to HAMLET in carcinoma cells and for the morphological changes accompanying death. In particular, they indicate the involvement of $Ca^{2+}$ and $K^+$ dependent channels but not Tetranidrine.

HAMLET-Induced Transcription is Greatly Reduced by Amiloride.

To understand the mechanisms of carcinoma cell death and the contribution of ion channel activation, the global transcriptional response to HAMLET was examined, using whole genome arrays. A549 lung carcinoma cells were exposed to HAMLET (21 µM) for one hour and cells pretreated with amiloride were compared to cells in medium alone. The raw data was normalized using RMA (Irizarry et al., 2003 Biostatistics 4: 249-264) and found to be of excellent quality with high replicate correlation (>0.99) and NUSE values close to 1. An unbiased global overview of transcription was obtained by performing a hierarchical clustering of the top 3000 genes by variance and was visualized in a heatmap (FIGS. 2D and 13). Genes with empirical Bayes adjusted p-values <0.05 and log 2 fold changes >1 were considered differentially expressed and were functionally characterized using Database for Annotation, Visualization and Integrated Discovery, (Dennis et al., 2003) and Ingenuity Pathway Analysis.

Figure 3:
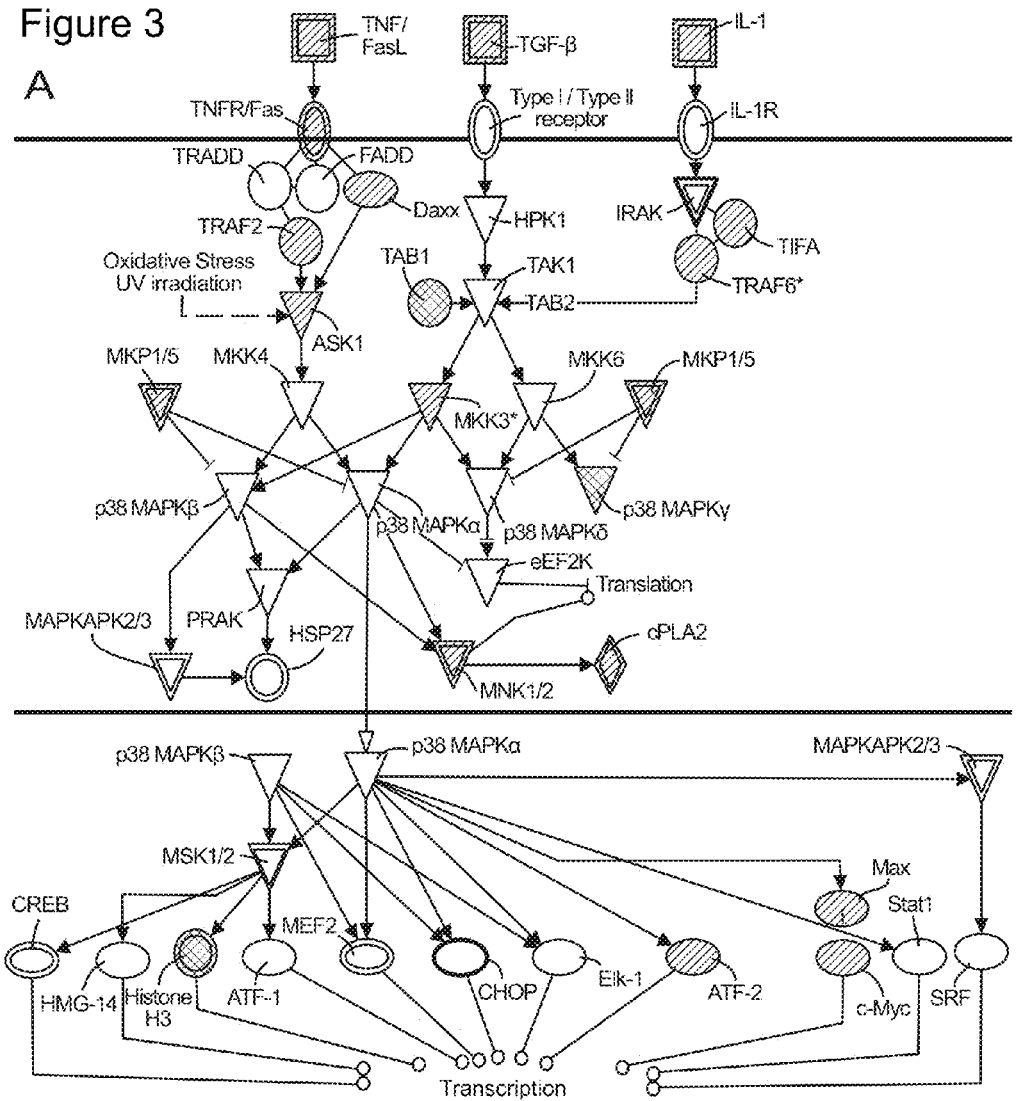
FIG. 3. HAMLET activates the p38-signaling pathway.
(A) Transcriptional changes were identified in HAMLET-treated A549 lung carcinoma cells. Three hundred sixty-seven genes showed a minimum log 2-fold change of 1.2 compared to PBS-treated control cells, with a Benjamini-Hochberg adjusted p-value <0.05. Ten genes in the p38 pathway were upregulated three hours after HAMLET treatment (21 μM) of lung carcinoma cells (A549), as marked in the canonical pathway. (B, C) Heat map (triplicate for each time period) and log 2 ratios of differentially expressed genes in the p38 pathway, 1, 3, 6 and 24 hours after HAMLET exposure. (D, E) Increased p38α, β, γ and HSP27 and reduced ERK1/2 phosphorylation in kidney (D) and lung (E) carcinoma cells exposed to HAMLET (35 μM, 30 minutes). Membranes with phospho-specific antibodies were probed with protein lysates from HAMLET- or PBS-treated (control) carcinoma cells. Protein phosphorylation was quantified using ImageJ. Data are mean±SEM of 3 experiments. (F) Dose- and time-dependent p38 phosphorylation in response to HAMLET. Blots of protein lysates were probed with antibodies specific for phosphorylated p38 (Thr180/Tyr182). Lung carcinoma cells were treated with HAMLET and compared to PBS-treated negative controls. Membranes were stripped and reprobed with total p38 and GAPDH antibody as a loading control.
Figure 3:
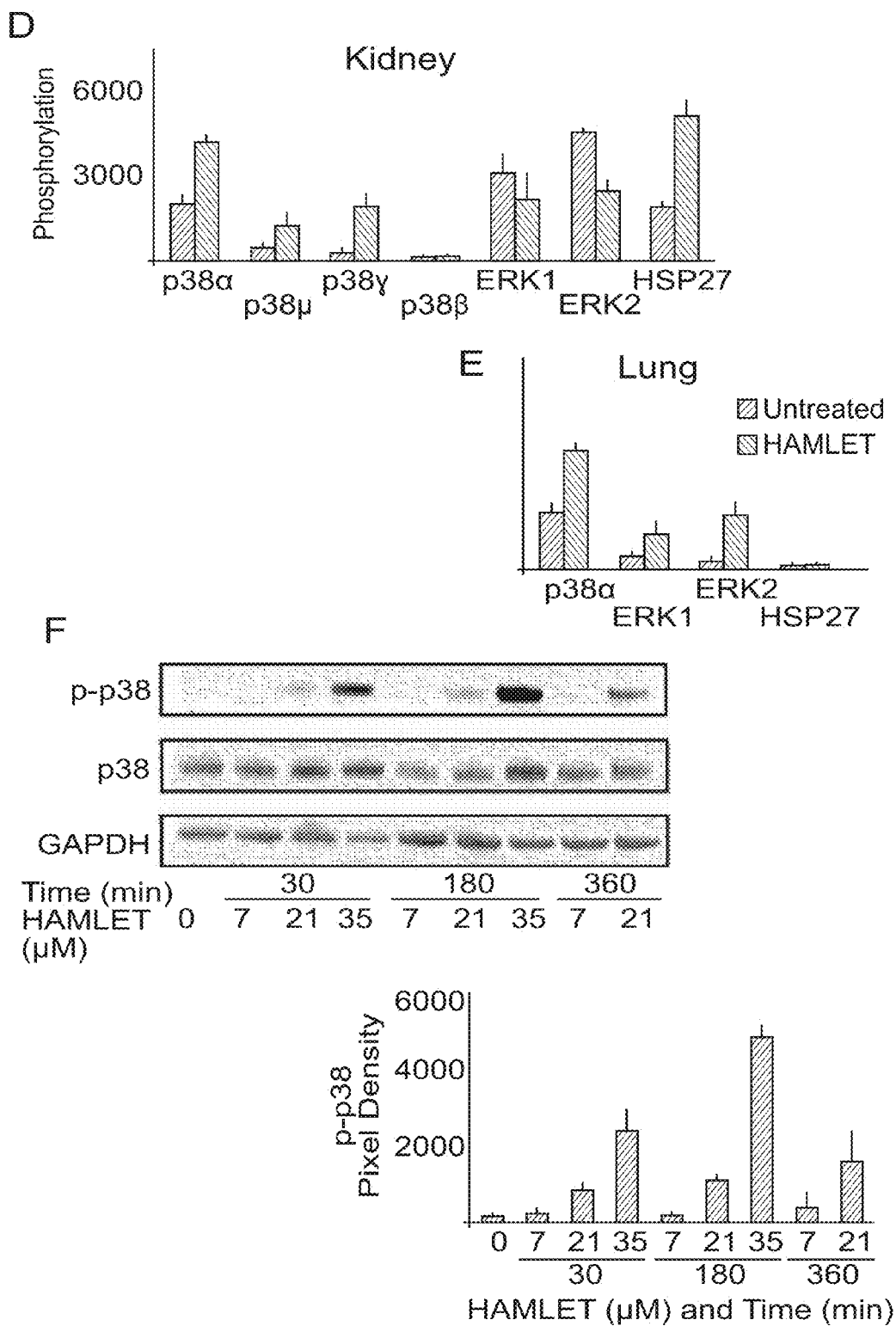

Ion channel inhibition caused a dramatic reduction of the transcriptional response to HAMLET. In the absence of inhibitor, a total of 336 genes were found differentially expressed in response to HAMLET treatment (FIG. 3B, Table 1).

TABLE 1

| Gene_Symbol | Gene_name |
|---|---|
| ATF3 | activating transcription factor 3 |
| ATF7IP2 | activating transcription factor 7 interacting protein 2 |
| ARL17A | ADP-ribosylation factor-like 17A |
| ADRB1 | adrenergic, beta-1-, receptor |
| AHSA2 | AHA1, activator of heat shock 90 kDa protein ATPase homolog 2 (yeast) |
| AREG | amphiregulin |
| ANGPTL4 | angiopoietin-like 4 |
| ANKRD1 | ankyrin repeat domain 1 (cardiac muscle) |
| AADAC | arylacetamide deacetylase (esterase) |
| ABCD3 | ATP-binding cassette, sub-family D (ALD), member 3 |
| ABCE1 | ATP-binding cassette, sub-family E (OABP), member 1 |
| ATP6V1B2 | ATPase, H+ transporting, lysosomal 56/58 kDa, V1 subunit B2 |
| AXIN2 | axin 2 |
| BCL6 | B-cell CLL/lymphoma 6 |
| BHLHE40 | basic helix-loop-helix family, member e40 |
| BRI3BP | BRI3 binding protein |
| BTBD10 | BTB (POZ) domain containing 10 |
| BANP | BTG3 associated nuclear protein |
| CCL20 | chemokine (C-C motif) ligand 20 |
| CXCL2 | chemokine (C—X—C motif) ligand 2 |
| CXCL3 | chemokine (C—X—C motif) ligand 3 |
| CLCC1 | chloride channel CLIC-like 1 |
| C1orf59 | chromosome 1 open reading frame 59 |
| C10orf140 | chromosome 10 open reading frame 140 |

TABLE 1-continued

| Gene_Symbol | Gene_name |
|---|---|
| C14orf181 | chromosome 14 open reading frame 181 |
| C20orf177 | chromosome 20 open reading frame 177 |
| C20orf199 | chromosome 20 open reading frame 199 |
| C6orf141 | chromosome 6 open reading frame 141 |
| C8orf4 | chromosome 8 open reading frame 4 |
| CTGF | connective tissue growth factor |
| CUL3 | cullin 3 |
| CCNG2 | cyclin G2 |
| CCNL1 | cyclin L1 |
| CDKL3 | cyclin-dependent kinase-like 3 |
| CYR61 | cysteine-rich, angiogenic inducer, 61 |
| CSRNP1 | cysteine-serine-rich nuclear protein 1 |
| CYP27B1 | cytochrome P450, family 27, subfamily B, polypeptide 1 |
| DDX3X | DEAD (Asp-Glu-Ala-Asp) box polypeptide 3, X-linked |
| DERL1 | Der1-like domain family, member 1 |
| DDIT3 | DNA-damage-inducible transcript 3 |
| DNAJB1 | DnaJ (Hsp40) homolog, subfamily B, member 1 |
| DOT1L | DOT1-like, histone H3 methyltransferase (*S, cerevisiae*) |
| DUSP1 | dual specificity phosphatase 1 |
| DUSP10 | dual specificity phosphatase 10 |
| DUSP5 | dual specificity phosphatase 5 |
| DUSP6 | dual specificity phosphatase 6 |
| DUSP8 | dual specificity phosphatase 8 |
| EGR1 | early growth response 1 |
| EGR2 | early growth response 2 |
| ENGASE | endo-beta-N-acetylglucosaminidase |
| EPHA2 | EPH receptor A2 |
| EREG | epiregulin |
| EPM2AIP1 | EPM2A (laforin) interacting protein 1 |
| ERRFI1 | ERBB receptor feedback inhibitor 1 |
| EIF4A1 | eukaryotic translation initiation factor 4A1 |
| EIF4A2 | eukaryotic translation initiation factor 4A2 |
| FAM172A | family with sequence similarity 172, member A |
| FAM173B | family with sequence similarity 173, member B |
| FAM178A | family with sequence similarity 178, member A |
| FAM24B | family with sequence similarity 24, member B |
| FASTKD1 | FAST kinase domains 1 |
| FOS | FBJ murine osteosarcoma viral oncogene homolog |
| FOSB | FBJ murine osteosarcoma viral oncogene homolog B |
| FST | follistatin |
| FOXQ1 | forkhead box Q1 |
| FRAT2 | frequently rearranged in advanced T-cell lymphomas 2 |
| GPR125 | G protein-coupled receptor 125 |
| GXYLT1 | glucoside xylosyltransferase 1 |
| GPAM | glycerol-3-phosphate acyltransferase, mitochondrial |
| GADD45A | growth arrest and DNA-damage-inducible, alpha |
| GADD45B | growth arrest and DNA-damage-inducible, beta |
| GDF15 | growth differentiation factor 15 |
| HBS1L | HBS1-like (*S, cerevisiae*) |
| HSPD1 | heat shock 60 kDa protein 1 (chaperonin) |
| HSPA1L | heat shock 70 kDa protein 1-like |
| HSPA1A | heat shock 70 kDa protein 1A |
| HSPA1B | heat shock 70 kDa protein 1B |
| HSPA6 | heat shock 70 kDa protein 6 (HSP70B') |
| HERC4 | heat domain and RLD 4 |
| HBEGF | heparin-binding EGF-like growth factor |
| HNRNPA0 | heterogeneous nuclear ribonucleoprotein A0 |
| HNRNPH3 | heterogeneous nuclear ribonucleoprotein H3 (2H9) |
| HMGA2 | high mobility group AT-hook 2 |
| HINT1 | histidine triad nucleotide binding protein 1 |
| HIST1H1C | histone cluster 1, H1c |
| HIST1H2AK | histone cluster 1, H2ak |
| HIST1H2BK | histone cluster 1, H2bk |
| HIST1H4E | histone cluster 1, H4e |
| HIST1H4H | histone cluster 1, H4h |
| HIST2H2BE | histone cluster 2, H2be |
| HAS2 | hyaluronan synthase 2 |
| IER2 | immediate early response 2 |
| INHBA | inhibin, beta A |
| ID3 | inhibitor of DNA binding 3, dominant negative helix-loop-helix protein |
| IL11 | interleukin 11 |
| IL12A | interleukin 12A (natural killer cell stimulatory factor 1, cytotoxic lymphocyte maturation factor 1, p35) |
| IL6 | interleukin 6 (interferon, beta 2) |
| IL8 | interleukin 8 |
| JUN | jun oncogene |
| KLHL7 | kelch-like 7 (*Drosophila*) |
| KRT34 | keratin 34 |

TABLE 1-continued

| Gene_Symbol | Gene_name |
|---|---|
| hCG_1749898 | keratin associated protein 2-4-like |
| KRTAP4-8 | keratin associated protein 4-8 |
| KIAA0776 | KIAA0776 |
| KLF10 | Kruppel-like factor 10 |
| KLF2 | Kruppel-like factor 2 (lung) |
| KLF4 | Kruppel-like factor 4 (gut) |
| KLF6 | Kruppel-like factor 6 |
| KLF7 | Kruppel-like factor 7 (ubiquitous) |
| LRRC49 | leucine rich repeat containing 49 |
| LIF | leukemia inhibitory factor (cholinergic differentiation factor) |
| LMBR1 | limb region 1 homolog (mouse) |
| LEAP2 | liver expressed antimicrobial peptide 2 |
| LRP5L | low density lipoprotein receptor-related protein 5-like |
| MCTS1 | malignant T cell amplified sequence 1 |
| MAP7D3 | MAP7 domain containing 3 |
| MALAT1 | metastasis associated lung adenocarcinoma transcript 1 (non-protein coding) |
| MEX3B | mex-3 homolog B (*C. elegans*) |
| MIB1 | mindbomb homolog 1 (*Drosophila*) |
| MYH9 | myosin, heavy chain 9, non-muscle |
| NA | NA |
| NDUFC2 | NADH dehydrogenase (ubiquinone) 1, subcomplex unknown, 2, 14, 5 kDa |
| NANOS1 | nanos homolog 1 (*Drosophila*) |
| NEDD9 | neural precursor cell expressed, developmentally down-regulated 9 |
| NEK2 | NIMA (never in mitosis gene a)-related kinase 2 |
| NKX3-1 | NK3 homeobox 1 |
| NFKBIZ | nuclear factor of kappa light polypeptide gene enhancer in B-cells inhibitor, zeta |
| ATF7IP2 | activating transcription factor 7 interacting protein 2 |
| ARL17A | ADP-ribosylation factor-like 17A |
| ADRB1 | adrenergic, beta-1-, receptor |
| AHSA2 | AHA1, activator of heat shock 90 kDa protein ATPase homolog 2 (yeast) |
| AREG | amphiregulin |
| ANGPTL4 | angiopoietin-like 4 |
| ANKRD1 | ankyrin repeat domain 1 (cardiac muscle) |
| AADAC | arylacetamide deacetylase (esterase) |
| ABCD3 | ATP-binding cassette, sub-family D (ALD), member 3 |
| ABCE1 | ATP-binding cassette, sub-family E (OABP), member 1 |
| ATP6V1B2 | ATPase, H+ transporting, lysosomal 56/58 kDa, V1 subunit B2 |
| AXIN2 | axin 2 |
| BCL6 | B-cell CLL/lymphoma 6 |
| BHLHE40 | basic helix-loop-helix family, member e40 |
| BRI3BP | BRI3 binding protein |
| BTBD10 | BTB (POZ) domain containing 10 |
| BANP | BTG3 associated nuclear protein |
| CCL20 | chemokine (C-C motif) ligand 20 |
| CXCL2 | chemokine (C—X—C motif) ligand 2 |
| CXCL3 | chemokine (C—X—C motif) ligand 3 |
| CLCC1 | chloride channel CLIC-like 1 |
| C1orf59 | chromosome 1 open reading frame 59 |
| C10orf140 | chromosome 10 open reading frame 140 |
| C14orf181 | chromosome 14 open reading frame 181 |
| C20orf177 | chromosome 20 open reading frame 177 |
| C20orf199 | chromosome 20 open reading frame 199 |
| C6orf141 | chromosome 6 open reading frame 141 |
| C8orf4 | chromosome 8 open reading frame 4 |
| CTGF | connective tissue growth factor |
| CUL3 | cullin 3 |
| CCNG2 | cyclin G2 |
| CCNL1 | cyclin L1 |
| CDKL3 | cyclin-dependent kinase-like 3 |
| CYR61 | cysteine-rich, angiogenic inducer, 61 |
| CSRNP1 | cysteine-serine-rich nuclear protein 1 |
| CYP27B1 | cytochrome P450, family 27, subfamily B, polypeptide 1 |
| DDX3X | DEAD (Asp-Glu-Ala-Asp) box polypeptide 3, X-linked |
| DERL1 | Der1-like domain family, member 1 |
| DDIT3 | DNA-damage-inducible transcript 3 |
| DNAJB1 | DnaJ (Hsp40) homolog, subfamily B, member 1 |
| DOT1L | DOT1-like, histone H3 methyltransferase (*S. cerevisiae*) |
| DUSP1 | dual specificity phosphatase 1 |
| DUSP10 | dual specificity phosphatase 10 |
| DUSP5 | dual specificity phosphatase 5 |
| DUSP6 | dual specificity phosphatase 6 |
| DUSP8 | dual specificity phosphatase 8 |
| EGR1 | early growth response 1 |
| EGR2 | early growth response 2 |
| ENGASE | endo-beta-N-acetylglucosaminidase |
| EPHA2 | EPH receptor A2 |
| EREG | epiregulin |
| EPM2AIP1 | EPM2A (laforin) interacting protein 1 |

TABLE 1-continued

| Gene_Symbol | Gene_name |
|---|---|
| ERRFI1 | ERBB receptor feedback inhibitor 1 |
| EIF4A1 | eukaryotic translation initiation factor 4A1 |
| EIF4A2 | eukaryotic translation initiation factor 4A2 |
| FAM172A | family with sequence similarity 172, member A |
| FAM173B | family with sequence similarity 173, member B |
| FAM178A | family with sequence similarity 178, member A |
| FAM24B | family with sequence similarity 24, member B |
| FASTKD1 | FAST kinase domains 1 |
| FOS | FBJ murine osteosarcoma viral oncogene homolog |
| FOSB | FBJ murine osteosarcoma viral oncogene homolog B |
| FST | follistatin |
| FOXQ1 | forkhead box Q1 |
| FRAT2 | frequently rearranged in advanced T-cell lymphomas 2 |
| GPR125 | G protein-coupled receptor 125 |
| GXYLT1 | glucoside xylosyltransferase 1 |
| GPAM | glycerol-3-phosphate acyltransferase, mitochondrial |
| GADD45A | growth arrest and DNA-damage-inducible, alpha |
| GADD45B | growth arrest and DNA-damage-inducible, beta |
| GDF15 | growth differentiation factor 15 |
| HBS1L | HBS1-like (S, cerevisiae) |
| HSPD1 | heat shock 60 kDa protein 1 (chaperonin) |
| HSPA1L | heat shock 70 kDa protein 1-like |
| HSPA1A | heat shock 70 kDa protein 1A |
| HSPA1B | heat shock 70 kDa protein 1B |
| HSPA6 | heat shock 70 kDa protein 6 (HSP70B') |
| HERC4 | heat domain and RLD 4 |
| HBEGF | heparin-binding EGF-like growth factor |
| HNRNPA0 | heterogeneous nuclear ribonucleoprotein A0 |
| HNRNPH3 | heterogeneous nuclear ribonucleoprotein H3 (2H9) |
| HMGA2 | high mobility group AT-hook 2 |
| HINT1 | histidine triad nucleotide binding protein 1 |
| HIST1H1C | histone cluster 1, H1c |
| HIST1H2AK | histone cluster 1, H2ak |
| HIST1H2BK | histone cluster 1, H2bk |
| HIST1H4E | histone cluster 1, H4e |
| HIST1H4H | histone cluster 1, H4h |
| HIST2H2BE | histone cluster 2, H2be |
| HAS2 | hyaluronan synthase 2 |
| IER2 | immediate early response 2 |
| INHBA | inhibin, beta A |
| ID3 | inhibitor of DNA binding 3, dominant negative helix-loop-helix protein |
| IL11 | interleukin 11 |
| IL12A | interleukin 12A (natural killer cell stimulatory factor 1, cytotoxic lymphocyte maturation factor 1, p35) |
| IL6 | interleukin 6 (interferon, beta 2) |
| IL8 | interleukin 8 |
| JUN | jun oncogene |
| KLHL7 | kelch-like 7 (Drosophila) |
| KRT34 | keratin 34 |
| hCG_1749898 | keratin associated protein 2-4-like |
| KRTAP4-8 | keratin associated protein 4-8 |
| KIAA0776 | KIAA0776 |
| KLF10 | Kruppel-like factor 10 |
| KLF2 | Kruppel-like factor 2 (lung) |
| KLF4 | Kruppel-like factor 4 (gut) |
| KLF6 | Kruppel-like factor 6 |
| KLF7 | Kruppel-like factor 7 (ubiquitous) |
| LRRC49 | leucine rich repeat containing 49 |
| LIF | leukemia inhibitory factor (cholinergic differentiation factor) |
| LMBR1 | limb region 1 homolog (mouse) |
| LEAP2 | liver expressed antimicrobial peptide 2 |
| LRP5L | low density lipoprotein receptor-related protein 5-like |
| MCTS1 | malignant T cell amplified sequence 1 |
| MAP7D3 | MAP7 domain containing 3 |
| MALAT1 | metastasis associated lung adenocarcinoma transcript 1 (non-protein coding) |
| MEX3B | mex-3 homolog B (C, elegans) |
| MIB1 | mindbomb homolog 1 (Drosophila) |
| MYH9 | myosin, heavy chain 9, non-muscle |
| NA | NA |
| NDUFC2 | NADH dehydrogenase (ubiquinone) 1, subcomplex unknown, 2, 14, 5 kDa |
| NANOS1 | nanos homolog 1 (Drosophila) |
| NEDD9 | neural precursor cell expressed, developmentally down-regulated 9 |
| NEK2 | NIMA (never in mitosis gene a)-related kinase 2 |
| NKX3-1 | NK3 homeobox 1 |
| NFKBIZ | nuclear factor of kappa light polypeptide gene enhancer in B-cells inhibitor, zeta |
| NR4A1 | nuclear receptor subfamily 4, group A, member 1 |
| NUBPL | nucleotide binding protein-like |
| OBFC2A | oligonucleotide/oligosaccharide-binding fold containing 2A |

TABLE 1-continued

| Gene_Symbol | Gene_name |
|---|---|
| PER1 | period homolog 1 (*Drosophila*) |
| PMAIP1 | phorbol-12-myristate-13-acetate-induced protein 1 |
| PHLDA1 | pleckstrin homology-like domain, family A, member 1 |
| PARP1 | poly (ADP-ribose) polymerase 1 |
| PABPC1L | poly(A) binding protein, cytoplasmic 1-like |
| PABPN1 | poly(A) binding protein, nuclear 1 |
| POLR2B | polymerase (RNA) II (DNA directed) polypeptide B, 140 kDa |
| PRDM1 | PR domain containing 1, with ZNF domain |
| PCYOX1 | prenylcysteine oxidase 1 |
| PREPL | prolyl endopeptidase-like |
| PTGS2 | prostaglandin-endoperoxide synthase 2 (prostaglandin G/H synthase and cyclooxygenase) |
| PSMD12 | proteasome (prosome, macropain) 26S subunit, non-ATPase, 12 |
| PPP1CB | protein phosphatase 1, catalytic subunit, beta isoform |
| PPP1R15A | protein phosphatase 1, regulatory (inhibitor) subunit 15A |
| PRPF3 | PRP3 pre-mRNA processing factor 3 homolog (*S, cerevisiae*) |
| RHOB | ras homolog gene family, member B |
| RGS2 | regulator of G-protein signaling 2, 24 kDa |
| RTN4IP1 | reticulon 4 interacting protein 1 |
| RND3 | Rho family GTPase 3 |
| RNGTT | RNA guanylyltransferase and 5'-phosphatase |
| SKP2 | S-phase kinase-associated protein 2 (p45) |
| SAMHD1 | SAM domain and HD domain 1 |
| SGK1 | serum/glucocorticoid regulated kinase 1 |
| SNHG12 | small nucleolar RNA host gene 12 (non-protein coding) |
| SNORA12 | small nucleolar RNA, H/ACA box 12 |
| SLC25A24 | solute carrier family 25 (mitochondrial carrier; phosphate carrier), member 24 |
| SLC9A2 | solute carrier family 9 (sodium/hydrogen exchanger), member 2 |
| SFRS2 | splicing factor, arginine/serine-rich 2 |
| SFRS5 | splicing factor, arginine/serine-rich 5 |
| SPRY2 | sprouty homolog 2 (*Drosophila*) |
| SBNO1 | strawberry notch homolog 1 (*Drosophila*) |
| SUMF1 | sulfatase modifying factor 1 |
| TAF1D | TATA box binding protein (TBP)-associated factor, RNA polymerase I, D, 41 kDa |
| THBS1 | thrombospondin 1 |
| TRA2A | transformer 2 alpha homolog (*Drosophila*) |
| TM9SF2 | transmembrane 9 superfamily member 2 |
| TMEM168 | transmembrane protein 168 |
| TMEM30A | transmembrane protein 30A |
| TRIB1 | tribbles homolog 1 (*Drosophila*) |
| WRB | tryptophan rich basic protein |
| TSC22D3 | TSC22 domain family, member 3 |
| TUFT1 | tuftelin 1 |
| TNFRSF10D | tumor necrosis factor receptor superfamily, member 10d, decoy with truncated death domain |
| TNFAIP3 | tumor necrosis factor, alpha-induced protein 3 |
| TP53INP1 | tumor protein p53 inducible nuclear protein 1 |
| USP9X | ubiquitin specific peptidase 9, X-linked |
| UXS1 | UDP-glucuronate decarboxylase 1 |
| UNC119B | unc-119 homolog B (*C, elegans*) |
| MAFF | v-maf musculoaponeurotic fibrosarcoma oncogene homolog F (avian) |
| MYC | v-myc myelocytomatosis viral oncogene homolog (avian) |
| ZC3HAV1 | zinc finger CCCH-type, antiviral 1 |
| ZNF280D | zinc finger protein 280D |
| ZFP36L1 | zinc finger protein 36, C3H type-like 1 |
| ZFYVE27 | zinc finger, FYVE domain containing 27 |
| ZMAT3 | zinc finger, matrin type 3 |

The gene list was dominated by pathway controlling p38 MAPK signaling (n=15, Adjusted p-value=$1.6*10^{-3}$), cell death regulation (Enrichment Score (ES)=4.7, n=22) or ER stress (ES=2.22, n=8). In contrast, only 52 genes were differentially expressed in cells pretreated with amiloride (Table 2).

TABLE 2

| SYMBOL | GENE NAME |
|---|---|
| EGR1 | early growth response 1 |
| FOS | FBJ murine osteosarcoma viral oncogene homolog |
| KLF2 | Kruppel-like factor 2 (lung) |
| FST | follistatin |
| MYLIP | myosin regulatory light chain interacting protein |

TABLE 2-continued

| SYMBOL | GENE NAME |
|---|---|
| NFKBIZ | nuclear factor of kappa light polypeptide gene enhancer in B-cells inhibitor, zeta |
| JUN | jun oncogene |
| RPL18 | ribosomal protein L18 |
| CXCL3 | chemokine (C—X—C motif) ligand 3 |
| PDK4 | pyruvate dehydrogenase kinase, isozyme 4 |
| HNRPDL | heterogeneous nuclear ribonucleoprotein D-like |
| RHOB | ras homolog gene family, member B |
| RPS24 | ribosomal protein S24 |
| CCNL1 | cyclin L1 |
| KLF6 | Kruppel-like factor 6 |
| NA | NA |

TABLE 2-continued

| SYMBOL | GENE NAME |
|---|---|
| ATF3 | activating transcription factor 3 |
| KLF10 | Kruppel-like factor 10 |
| CCL20 | chemokine (C-C motif) ligand 20 |
| CXCL2 | chemokine (C—X—C motif) ligand 2 |
| C8orf4 | chromosome 8 open reading frame 4 |
| HAS2 | hyaluronan synthase 2 |
| MEX3B | mex-3 homolog B (*C. elegans*) |
| IL6 | interleukin 6 (interferon, beta 2) |
| MAT2A | methionine adenosyltransferase II, alpha |
| CUZD1 | CUB and zona pellucida-like domains 1 |
| HBP1 | HMG-box transcription factor 1 |
| CD55 | CD55 molecule, decay accelerating factor for complement (Cromer blood group) |
| PRC1 | protein regulator of cytokinesis 1 |
| PTGS2 | prostaglandin-endoperoxide synthase 2 (prostaglandin G/H synthase and cyclooxygenase) |
| BTG2 | BTG family, member 2 |
| DDIT3 | DNA-damage-inducible transcript 3 |
| DUSP5 | dual specificity phosphatase 5 |
| PRDM1 | PR domain containing 1, with ZNF domain |
| AREG | amphiregulin |
| RPL37A | ribosomal protein L37a |

Detected genes were mainly involved in transcriptional regulation and did not include genes involved in p38 signaling, cell death or ER stress. Amiloride alone had no significant effect on transcription. The results implied that ion channel activation is needed for the transcriptional response to HAMLET to occur.

HAMLET Triggers ER Stress in Carcinoma Cells.

Disturbances in ER $Ca^{2+}$ regulation can impair protein folding in the ER by inactivation of $Ca^{2+}$ dependent chaperones, such as GRP78 and calreticulin. An increase in unfolded proteins may activate a conserved series of signal-transduction events. Spanning the ER membrane, three ER stress sensors PERK, ATF6 and IRE1 are activated by an overload of unfolded proteins. Upon PERK activation, eIF2α is phosphorylated, shutting down protein translation to avoid unfolded protein overload. To examine if HAMLET disturbs the ER and triggers an unfolded protein response, we analyzed the transcription of ER stress-induced genes. The microarray analysis revealed an ER stress response in HAMLET-treated lung carcinoma cells, with increased transcription of key ER stress-related genes such as ATF4 (activating transcription factor 4), BiP (GRP78), IRE1 (inositol-requiring enzyme 1), PERK (PKR-like ER kinase), and XBP1 (X-box binding protein 1), (FIGS. 4A and 4B). At the protein level, HAMLET triggered time—(30 minutes) and dose-dependent eIF2α phosphorylation in A549 tumor cells (FIG. 3C). Western blotting additionally revealed an increase in cleaved as well as full-length ATF6 after three hours of HAMLET treatment (FIG. 3D). XBP1 splicing through IRE1 (Yoshida et al., 2001) was detected by PCR in HAMLET-treated carcinoma cells (30 minutes), yielding a 442 bp PCR product (XBP1) and a smaller product lacking 26 bp (XBP1s), (FIG. 3E). This response was more rapid than XBP1 splicing in response to the tunicamycin control despite the high concentration of tunicamycin applied (15 mg/mL). Finally, CHOP mRNA, which encodes a pro-apoptotic transcription factor strongly implicated in ER stress-induced cell death (Wang et al., 1996 Science 272: 1347-1349), increased 30-fold after HAMLET treatment (3 hours, FIG. 3F) confirming the strong regulation of CHOP also observed in the microarray studies. The results are consistent with a direct and rapid disturbance of the ER by HAMLET, as reflected by $Ca^{2+}$ mobilization.

HAMLET Triggers a p38-Dependent Death Response in Tumor Cells.

To identify the pathways that execute tumor cell death downstream of the ion channels, we further examined the global transcriptional responses to HAMLET in human lung carcinoma (A549) and kidney carcinoma (A498) cells over an extended period of 15 min to 24 hours. The p38 MAPK signaling pathway was identified as a top-scoring canonical pathway in A549 cells (FIG. 4A).

The MKK3 gene, which acts directly upstream of p38 and is responsible for its phosphorylation and activation, was upregulated, along with nine p38-pathway genes (FIG. 4B,C). Two dual-specificity phosphatases (DUSPs, DUSP1 and DUSP10) were upregulated with log 2-fold changes of 1.34 and 1.98, respectively. DUSPs are known feedback regulators of MAPK signaling, up-regulated when the pathway is active (Owens et al., 2007 Oncogene 26: 3203-3213). Additionally, both DUSP1 and DUSP10 are promiscuous and known to regulate both JNK (DUSP1 and DUSP10) as well as ERK (DUSP1). Genes downstream of p38 included CREB5, CHOP and HIST2H3C. The response to HAMLET was biphasic for most of the regulated genes, with an initial increase that peaked after three hours and continued for six hours. After 24 hours, transcriptional activity returned to baseline levels for six of the ten genes, while IRAK2, PLA2G4C, CHOP and CREB5 sustained elevated expression. Other genes affected by HAMLET treatment were involved in cell death and chromatin structure, consistent with previous observations (Aits et al., 2009 Int. J. Cancer 124: 1008-1019; Svanborg et al., 2003). The results were confirmed in A498 kidney carcinoma cells, where the p38 pathway again emerged as the top-scoring canonical pathway (FIG. 11).

Figure 4:
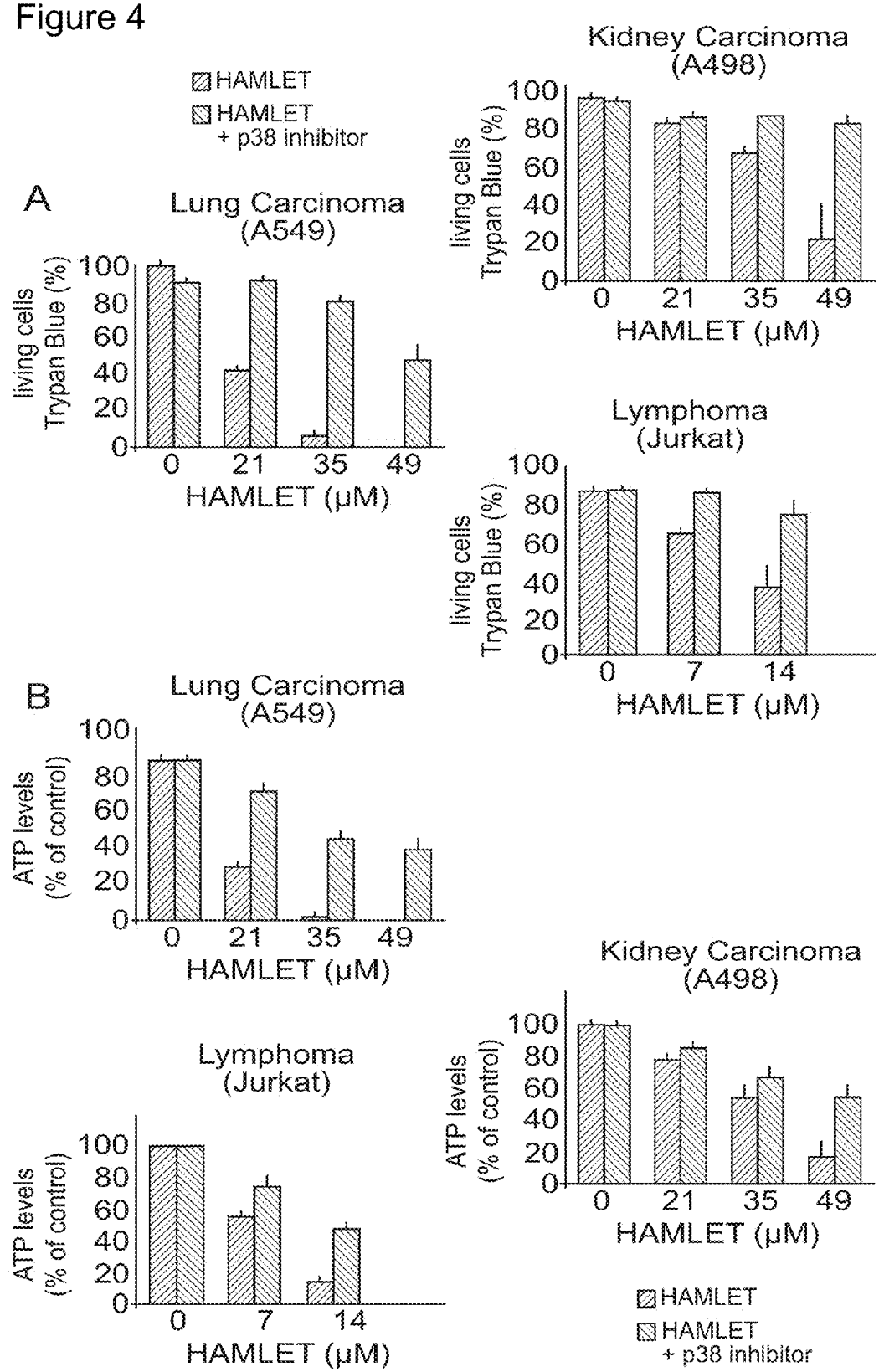
FIG. 4. p38 inhibition rescues carcinoma and lymphoma cells from death and morphological change in response to HAMLET.
(A, B) p38 inhibition (SB202190, 20 μM) rescued carcinoma (A549 and A498) and T-cell lymphoma (Jurkat) cells from death in response to HAMLET (7-49 μM, 3 h). Viability was quantified by Trypan blue exclusion (A) or as ATP levels (B). Data are means+SEMs for 3 independent experiments. (C) Real-time images of cell morphology after HAMLET exposure, showing that p38 inhibition prevents morphological changes in carcinoma cells (nuclear condensation, rounding up and blebbing). (D-E) A549 lung carcinoma cells were transfected using siRNA against p38a/MAPK14 and/or p38β/MAPK11 or non-targeting siRNA. Relative MAPK11 and MAPK14 mRNA levels are shown (MAPK/GAPDH, in % of non-transfected cells) as means+SEMs for 4 independent experiments. Knockdown was also confirmed on the protein level by western blot against total p38 (representative blot shown). GAPDH was used as a loading control. (F) The cytotoxic effect of HAMLET was quantified 48 hours after transfection as reduction in ATP levels. Data are means+SEM for four independent experiments. * p<0.05, *** p<0.001.
Figure 4:
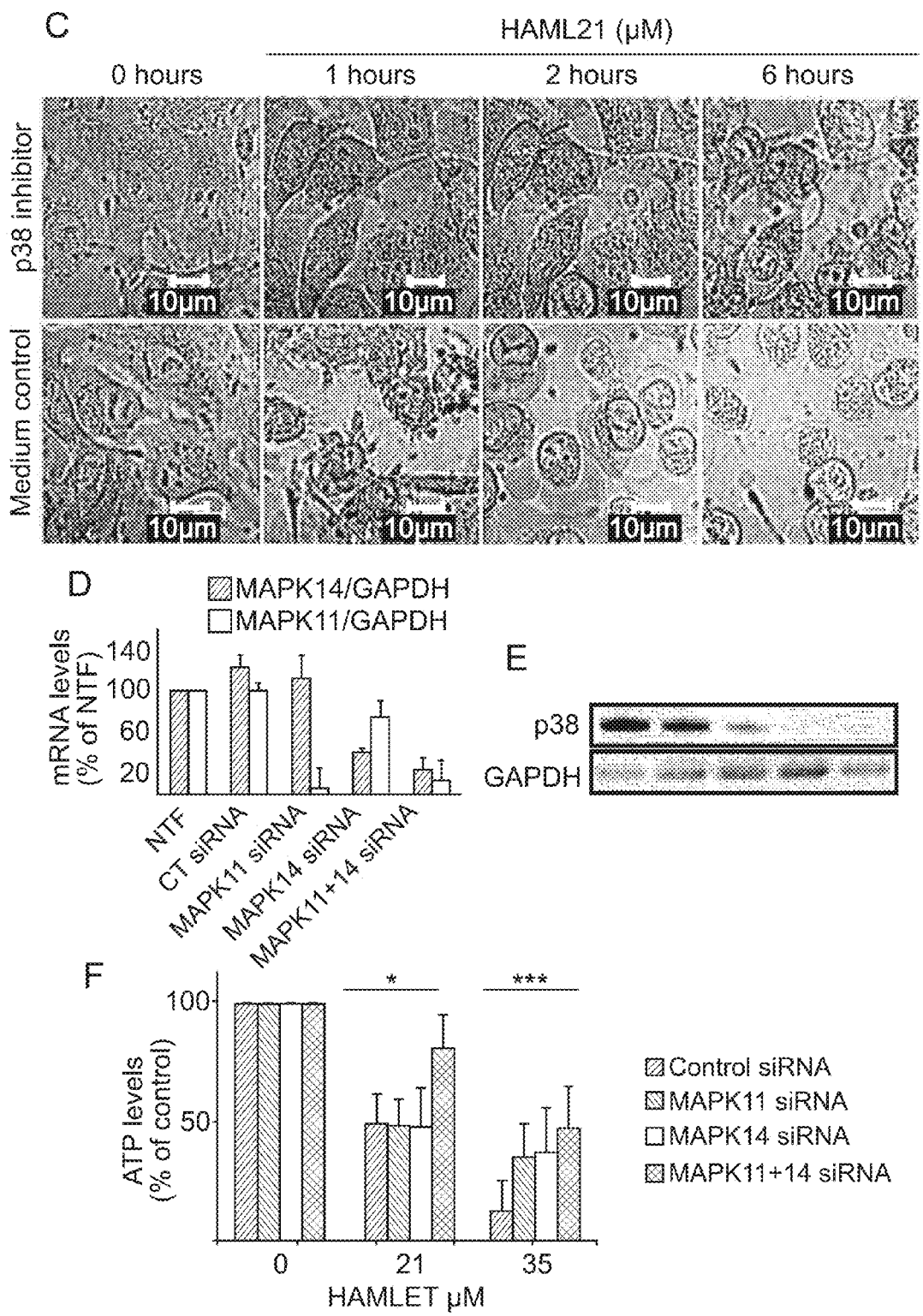

P38 MAPKs are activated by dual phosphorylation on conserved threonine and tyrosine residues by MKK3/6 and when phosphorylated, a wide variety of effector proteins, including MAPKAPK2 kinases, HSP27 chaperones and ATF2 and CHOP transcription factors become active (Cuenda et al., 2007 Biochimica et Biophysica Acta 1773: 1358-1375). In phospho-MAPK antibody arrays, both kidney and lung carcinoma cells were shown to rapidly respond to HAMLET (30 minutes) by phosphorylating p38a and HSP27 (FIG. 3D,E; phosphoarray images given in FIG. 12A, B). In addition, p38β and p38γ were phosphorylated in kidney carcinoma cells (FIG. 4D). There was a parallel loss of ERK1/2 phosphorylation in both cell types, consistent with a shift from cell proliferation to cell death (FIG. 4 D,E), (Xia et al., 1995 Science 270: 1326-1331). JNK kinase showed minimal alterations after 30 minutes (FIG. S2A, B). Phosphorylation of p38 was also confirmed by Western blot and was shown to be dose- and time-dependent (FIG. 3F). In marked contrast, no phosphorylation of p38, its isoforms, or HSP27 occurred in healthy, differentiated kidney cells in response to HAMLET (FIG. 12E).

Figure 5:
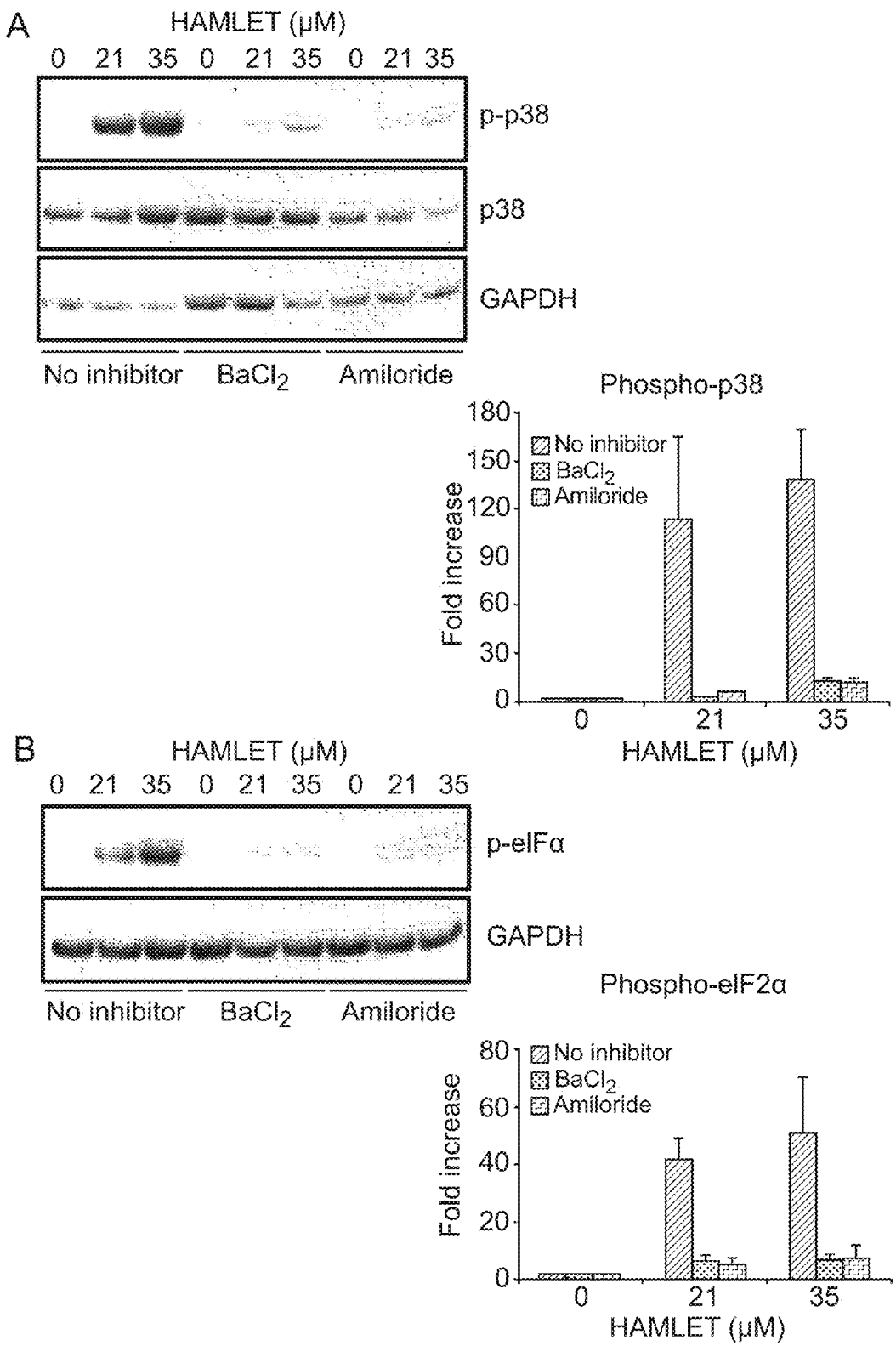
FIG. 5. Ion channel inhibitors reduce protein phosphorylation.
Amiloride or $BaCl_2$ reduced phosphorylation of targets in the p38 signaling and ER stress pathways. Lung carcinoma cells were exposed to HAMLET (21 and 35 μM) for 1 hour, protein lysates were blotted, incubated with antibodies as noted in the figure and quantified using ImageJ (Representative blot, +SEMs of 2-3 independent experiments). (A) Amiloride or $BaCl_2$ (30 minutes pretreatment) inhibited HAMLET-induced p38 phosphorylation and (B) ER stress, as shown by reduced eIF2α phosphorylation. (C) Amiloride or $BaCl_2$ inhibited the change Ras/RAF/MEK-MAPK signaling as suppression of p-ERK1/2 phosphorylation by HAMLET was reversed.
Figure 5:
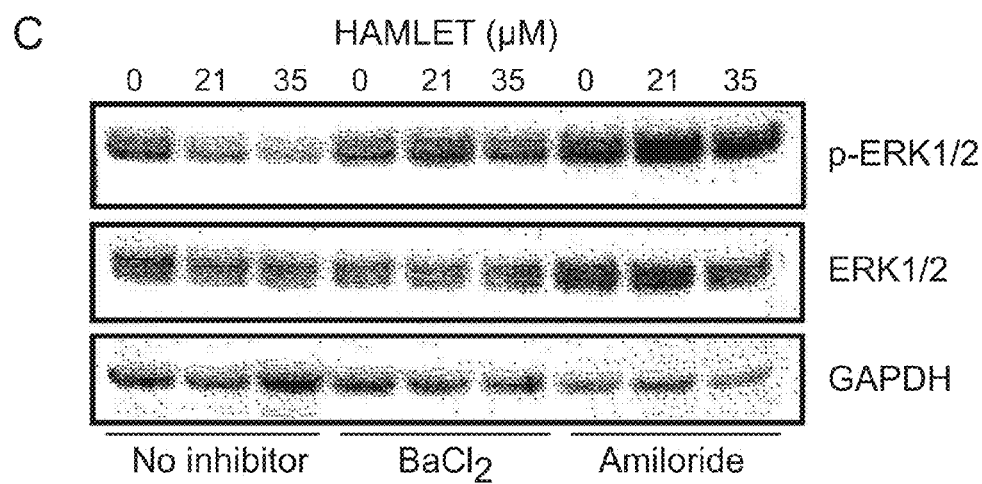
Figure 5:
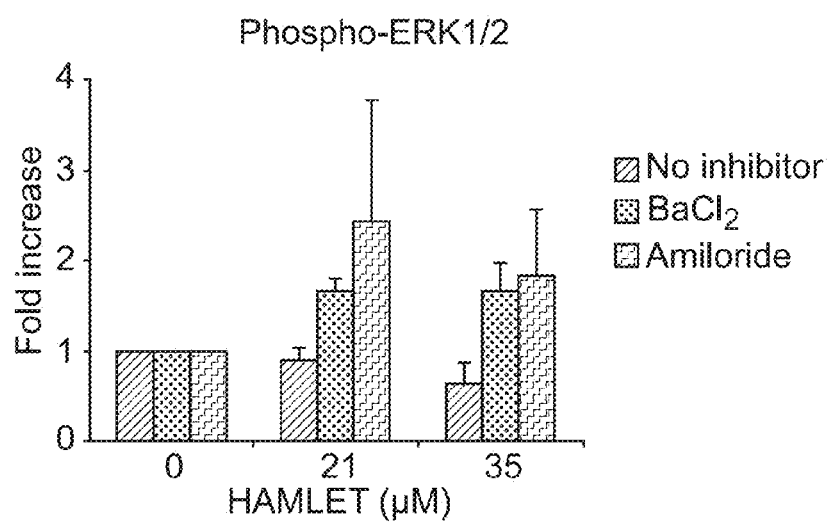

To determine if p38 signaling was involved in cell death, we inhibited p38a and p38β in lung and kidney carcinoma and Jurkat lymphoma cells with two small-molecule p38 inhibitors: SB202190, a highly specific pyridinyl-imidazole inhibitor; and BIRB796, a diaryl urea compound, which bears little structural similarity to SB202190 (Fabian et al., 2005 Nature Biotechnology 23: 329-336), (FIGS. 5A-B and FIG. 12B). The rapid, dose-dependent tumoricidal response to HAMLET was clearly attenuated by the SB202190, as measured by trypan blue staining (FIG. 5A) and ATP levels (FIG. 5B). The effect of p38 inhibition on cell death was also observed by real-time confocal imaging of lung carcinoma cells exposed to fluorescently labeled HAMLET. Images of unfixed cells, recorded in real time, revealed rapid morphological changes with blebbing, rounding up, loss of cytoplasm and nuclear condensation (FIG. 5C). The p38 inhibitor delayed these changes for about six hours (FIG. 5C). To rule out that the observed effects were due to p38 un-related effects, we also used siRNA targeting p38a and p38β. siRNA-mediated suppression of p38α and p38β in combination blocked HAMLET induced cell death (FIG. 5D), but neither of the siRNAs had any effect, indicating that one isoform is enough to induce cell death. The inhibition of p38 MAPK activity by SB202190 was accompanied by a marked decrease in p38 and HSP27 phosphorylation (FIG. 12C, D) upon HAMLET treatment.

These results identify p38 MAPK pathway genes as major effectors of the early death response to HAMLET and suggest that when p38 is blocked, significant rescue occurs.

In Healthy, Differentiated Cells HAMLET Activates Innate Immunity without a p38 Response.

Figure 6:
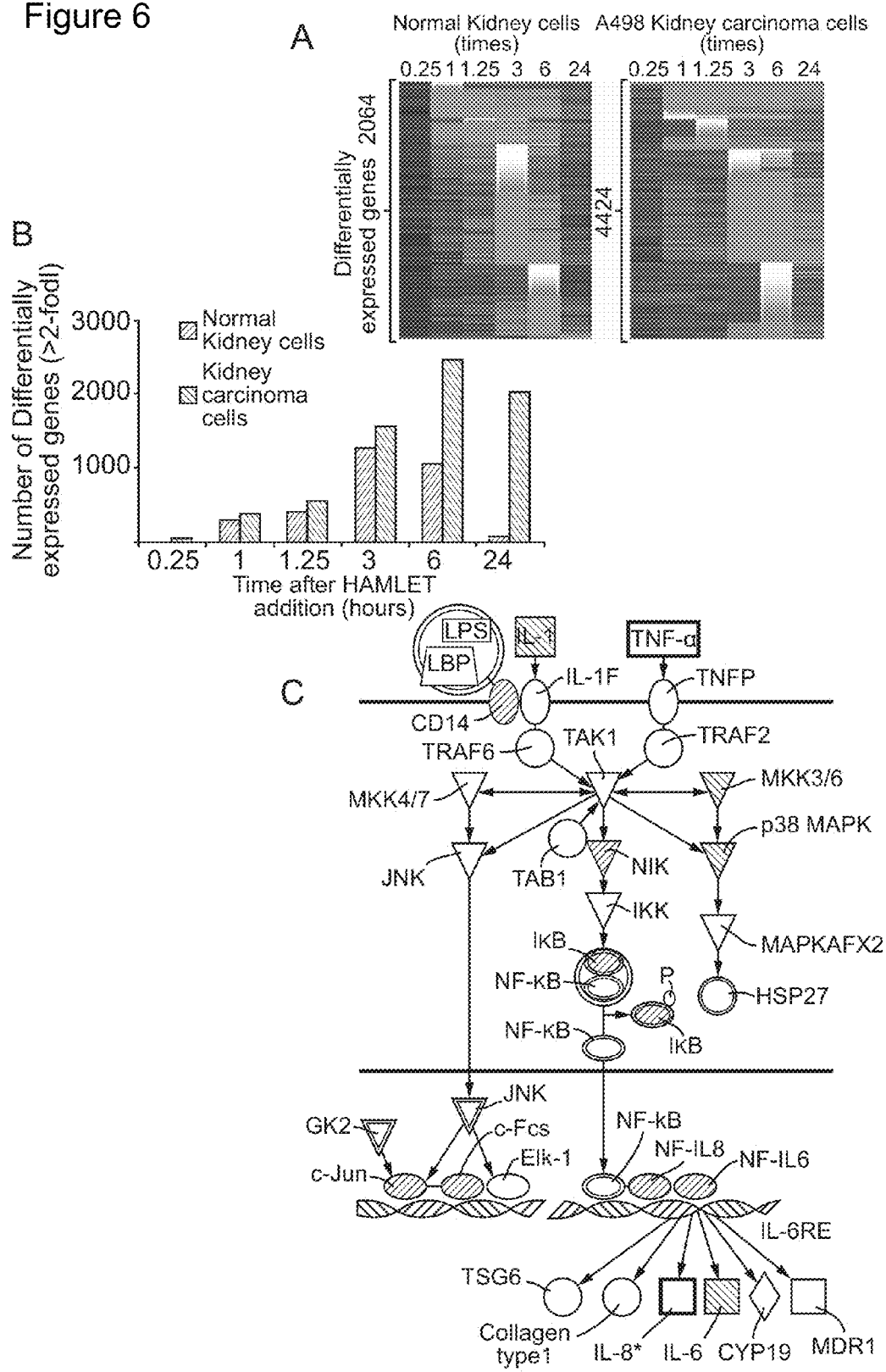
FIG. 6. Innate immune response to HAMLET in normal, differentiated cells.
Figure 6:
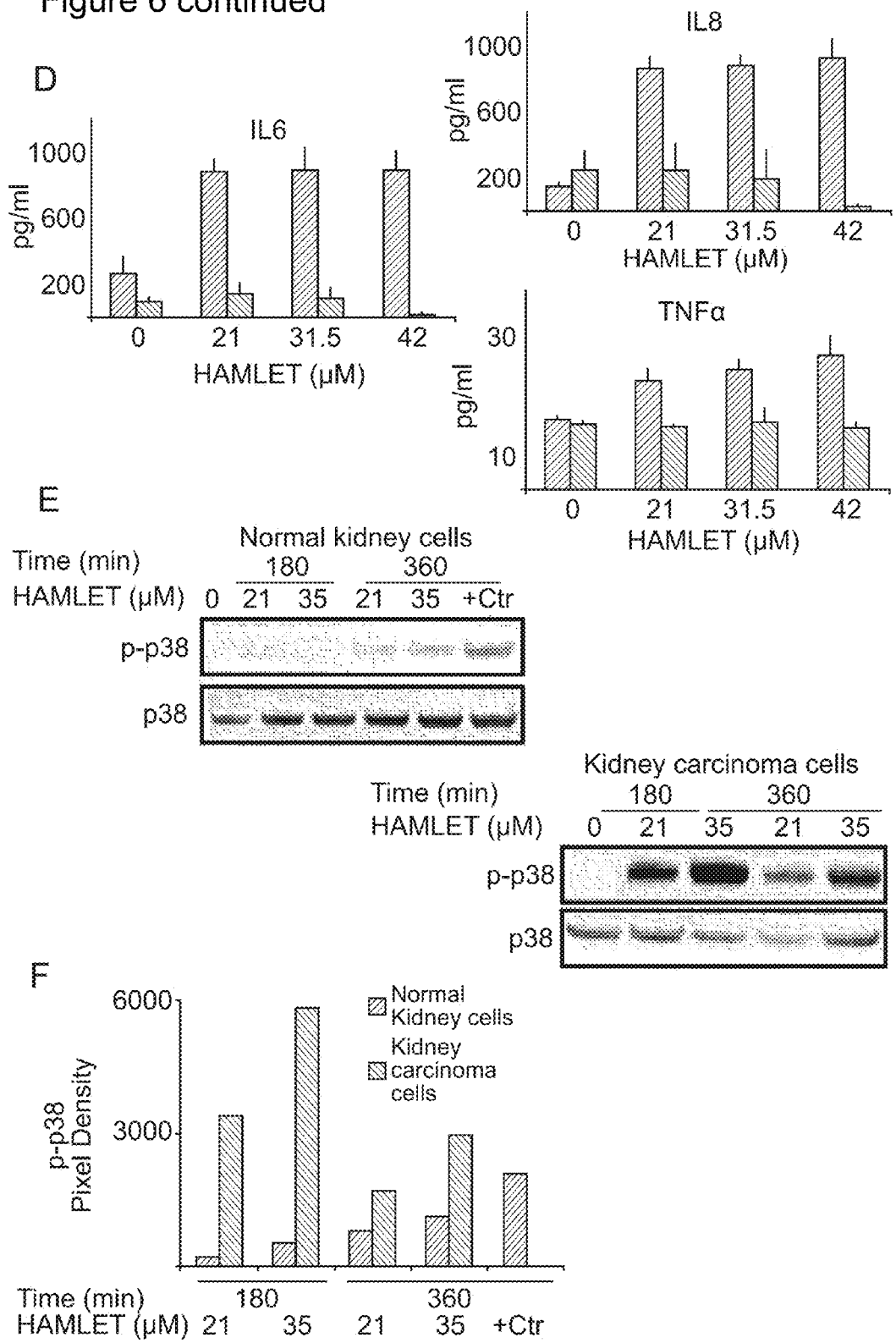

To examine the molecular basis of the difference in HAMLET susceptibility between carcinoma cells and healthy, differentiated cells, transcriptional profiles were compared. Healthy cells responded less strongly to HAMLET than kidney carcinoma cells (2064 genes in pediatric kidney compared to 4424 in kidney carcinoma cells, FIG. 6A) and exhibited a transient, rather than a sustained, response (FIG. 6B). Strikingly, the p38-signaling pathway showed evidence of downregulation at early time points with decreased expression of MKK3, p38 and HSP27 after 60 and 75 minutes of HAMLET exposure (FIG. 6E). Pathways significantly regulated by HAMLET in healthy cells were found to be involved in innate immune regulation (IL-6 pathway, FIG. 6C) and glucocorticoid signaling. Those prominent upregulated genes identified included IL-1, IL-6, c-Jun, c-Fos, IkB and TNFα, and a clear increase in secreted protein levels was confirmed for IL-6, IL-8, and TNFα (FIG. 6D). These cytokines were not secreted by the carcinoma cells. Moreover, other death-related signaling pathways identified as differentially expressed in carcinoma cells such as the death receptor, p53, and ER stress showed no significant regulation in healthy, differentiated cells. Thus, healthy, differentiated cells exposed to HAMLET exhibited a restricted, p38-independent innate immune response.

HAMLET-Induced p38 and eIF2a Phosphorylation and Innate Immune Responses are Prevented by Ion Channel Inhibitors.

To examine if ion channels also controlled phosphorylation in response to HAMLET, tumor cells were pretreated with ion channel inhibitors and p38-, eIF2α- and ERK1/2-phosphorylation were quantified using phospho-specific antibodies. The ion channel blockers reduced p38 or eIF2α phosphorylation in carcinoma cells (FIGS. 7A and B) and in parallel, the reduction in ERK1/2 phosphorylation was reversed (FIG. 7B). Thus, ion channel blockers were able to not only block transcriptional changes in response to HAMLET, but also to abrogate the phospho-signaling within these pathways.

To further examine if the innate immune response in healthy, differentiated cells requires functional ion channels, the expression of IL-6, IL-8 and TNFα mRNA was quantified in cells pretreated with amiloride and $BaCl_2$, using qRT-PCR. HAMLET (21 μM, 1 hour) caused a 30-fold increase in IL-6 mRNA that was abolished by amiloride (FIG. 7D). Similar results were seen for IL-6 and TNFα. $BaCl_2$ did not inhibit the IL-6 and IL-8 response to HAMLET, but caused a reduction in HAMLET induced TNFα expression.

These results confirm that ion fluxes and ion channel activation is an essential step to activate the different cellular responses to HAMLET in both carcinoma cells and healthy, differentiated cells. Interestingly, the Ras/MAPK-pathway, which is crucial for cell survival, was sustained when the HAMLET cells were pretreated with inhibitors.

Example 2

Comparison of the Cellular Responses Evoked by HAMLET/Oleate and Oleic Acid

Methods
Preparations of Stock Solutions:
Oleic acid: 5 μl of oleic acid was "diluted" in 1 ml of RPMI to give a 16 mM "cloudy solution".
Oleate: 5 mg of sodium oleate was dissolved in 1 ml of RPMI to give a 16 mM clear solution.
HAMLET, prepared as described for example in WO9926979: 1 mg diluted in 100 ul of PBS. $0.001/15200=6.6\times10^{-8}$ mol
Added to Each of the Wells:
  HAMLET: 50 ul=$3.3\times10^{-8}$ mol ALA, $16.5\times10^{-8}$ mol OA
  Oleate/OA: 10 ul=$1\times10^{-5}$ L×$16\times10^{-3}$=$1.6\times10^{-7}$=16 mol OA (10 ul of the Oleate and Oleic acid stock solutions is molar equivalent to the moles of OA/Na-olate present in 0.5 mg HAMLET).
Cell Death Assay:
A549 cells were seeded to a density of $0.8-1.0\times10^6$ cells/well in RPMI without FCS. Different volumes of HAMLET/oleate and oleic acid solutions were added. The cells were incubated for 1 hour at 37° C. 5% $CO_2$ for 1 hour before 50 μl of FCS (5% final concentration) were added to the wells. The cells were then further incubated for additional 2 hours before the viability were determined by trypan blue exclusion and ATP measurements.

The results are shown in FIG. 14 wherein FIG. 14A shows the mean value of the trypan blue assay and FIG. 14B shows the mean ATP values, where Ct is the control, HL is HAMLET, OA is oleic acid at a concentration in mol, equivalent to that which occurs in 0.5 mg HAMLET and Na-OA represents sodium oleate also at a concentration in a molar equivalent to the amount in HAMLET-oleate.

The experiment was repeated but with various concentrations of oleic acid and sodium oleate to try to ascertain a dose response. The results are shown in FIG. 15.

This series of experiments shows that HAMLET kills tumor cells more efficiently than protein free oleate or oleic acid (OA). The molar concentrations were chosen based on the known stoichiometry in HAMLET.

However, it was found that the oleate was also tumoricidal, as shown using a dose response design. Oleate killed the tumor cells at concentrations three to five times higher than the concentration in HAMLET. This effect was stronger than that of oleic acid.

Example 3

Conversion of Partially Unfolded Alphalactalbumin on an Oleate-Conditioned Column; Comparison with HAMLET after OA Conditioning Methods:
10 μl oleic acid was dissolved in 100 μl of EtOH and 10 ml of A buffer (10 mM TRIS, 0.15 mM Na CI, pH 8.5) was added during agitation. The oleic acid was added to the column, as previously described, and used for conversion of EDTA treated alphalactalbumin.

10 mg of Sodium oleate were dissolved in 1 ml of A×1 buffer as mentioned above and then further diluted to a total volume of 10 ml and added to the column corresponding to procedure used for oleic acid procedure. The column was then used for conversion of EDTA treated alphalactalbumin.

The results are shown in FIG. 16. The ability of oleate to form HAMLET-like complexes was compared to that of OA. Conversion efficiencies were similar, in terms of the position of the peak eluted with high salt, but proper stoichiometry of protein vs oleate needs to be examined (FIG. 16A). In this work, the yield of active fraction obtained with a column conditioned with sodium oleate was comparable or better than when using oleic acid.

In addition, the cell death response of the two complexes was investigated using the method described in Example 1. The results are shown in the following table.

| Tumoricidal activity of Oleate-HAMLET | | | |
|---|---|---|---|
| Substance | Conc. (mg/ml) | Trypan blue | ATP Activity |
| Control | — | 88 | 100 |
| HAMLET | 0.5 | 8 | 21 |
| Oleate-HAMLET | 0.5 | 1 | 27 |

In this data set, the oleate complex was at least as tumoricidal as the OA complex.

Example 4

Circular Dichroism (CD) Spectroscopy of HAMLET and NaOA-HAMLET

Materials and Methods

Far- and near-UV CD spectra were collected on HAMLET and NaOA-HAMLET at 25° C. using a Jasco J-810 spectropolarimeter. Lyophilized materials were dissolved in PBS to 1 mg/ml (32 µM for HAMLET and 43 µM HAMLET-NaOA as measured by $A_{280}$). Near-UV spectra were obtained between 240 and 320 nm and far-UV spectra between 195 and 250 nm. The wavelength step was 1 nm, the response time was 8 s, and scan rate was 10 nm/min. An average of six scans was presented where the mean residue ellipticity, $\theta_m$ in deg $cm^2$ $dmol^{-1}$, was calculated as described previously (Svensson et al., 1999, *J. Biol. Chem.*, 274: 6388-96).

The results are shown in FIG. 17. The tertiary structure of HAMLET (black continuous line) and NaOA-HAMLET (dashed line) were examined by near-UV CD spectroscopy. The spectra were recorded at 1 mg/ml in PBS. The spectra of both HAMLET and NaOA-HAMLET were essentially identified, showing a decrease in intensity as compared to that of a fully folded protein. The difference in the intensity of the two spectra was due to a difference in their molar concentrations (32 µM for HAMLET; 43 µM for NaOA-HAMLET. The secondary structure of the two complexes was examined by far-UV CD spectroscopy. Both complexes retained an almost identical content of secondary structure, as shown by K2D secondary structure analysis.

Example 5

Transcriptomic Studies

The relative effects on gene expression in the cells treated as described in Example 1 was investigated to try to determine at the genomic level, the effects of the various components.

In total 12 RNA samples were generated (triplicate of control, oleic Acid, HAMLET, and oleate-treated) and hybridized to Affymetrix Whole Genome microarrays U219. The resulting hybridization profiles were assessed pre- and post-RMA normalization and found to be of excellent quality. For statistical analysis normalized data were linear model fitted and Empirical Bayesian analysis, coupled with p-value adjustment, performed.

From the resulting comparison a total of 336 and 426 genes were identified as differentially expressed with an adjusted p-value <0.05 and log 2-foldchange of 1 for HAMLET and oleate treated cells, respectively. In contrast, oleic acid treated cells had a transcriptional program very similar to that of control cells with only two genes differentially expressed.

The resulting gene lists from HAMLET (Table 4) and oleate treated cells (Table 5) were compared and found to share a great number of genes (n=145, Table 3). In the following tables, abbreviations are as given above in Table 1 and Table 2.

TABLE 3

ATF3, AHSA2, AREG, ANGPTL4, ANKRD1, AADAC, ABCD3, ABCE1, ATP6V1B2, BCL6, BHLHE40, BANP, CCL20, CXCL2, CXCL3, CLCC1, C10orf140, C14orf181, C6orf141, C8orf4, CTGF, CUL3, CCNL1, CDKL3, CYR61, CSRNP1, DDX3X, DERL1, DDIT3, DNAJB1, DOT1L, DUSP1, DUSP10, DUSP5, DUSP6, DUSP8, EGR1, EGR2, EPHA2, EREG, ERRFI1, EIF4A2, FAM172A, FAM173B, FASTKD1, FOS, FOSB, FST, FOXQ1, GPR125, GPAM, GADD45A, GADD45B, GDF15, HBS1L, HSPD1, HSPA1L, HSPA1A, HSPA1B, HSPA6, HERC4, HBEGF, HNRNPA0, HNRNPH3, HMGA2, HINT1, HIST1H1C, HIST1H2AK, HIST1H2BK, HIST1H4E, HIST2H2BE, HAS2, IER2, INHBA, ID3, IL11, IL12A, IL6, IL8, JUN, KLHL7, KRT34, hCG_1749898, KRTAP4-8, KIAA0776, KLF10, KLF2, KLF4, KLF6, KLF7, LRRC49, LIF, LRP5L, MCTS1, MAP7D3, MALAT1, NA, NDUFC2, NANOS1, NEDD9, NEK2, NKX3-1, NFKBIZ, NR4A1, NUBPL, PER1, PMAIP1, PHLDA1, PABPC1L, POLR2B, PRDM1, PCYOX1, PREPL, PTGS2, PSMD12, PPP1R15A, RHOB, RGS2, RTN4IP1, RND3, SKP2, SAMHD1, SGK1, SNHG12, SNORA12, SLC9A2, SFRS2, SPRY2, SBNO1, SUMF1, TAF1D, TRA2A, TM9SF2, TMEM168, TMEM30A, TRIB1, WRB, TSC22D3, TNFAIP3, UXS1, UNC119B, MAFF, MYC, ZC3HAV1, ZFP36L1.

TABLE 4

ATF7IP2, ARL17A, ADRB1, AXIN2, BRI3BP, BTBD10, C1orf59, C20orf177, C20orf199, CCNG2, CYP27B1, ENGASE, EPM2AIP1, EIF4A1, FAM178A, FAM24B, FRAT2, GXYLT1, HIST1H4H, LMBR1, LEAP2, MEX3B, MIB1, MYH9, OBFC2A, PARP1, PABPN1, PPP1CB, PRPF3, RNGTT, SLC25A24, SFRS5, THBS1, TUFT1, TNFRSF10D, TP53INP1, USP9X, ZNF280D, ZFYVE27, ZMAT3.

TABLE 5

DERA, ALCAM, ACOT9, ADAMTS1, ARL14, ARL4D, ADRB2, ADM, AKNAD1, ANKRD37, ANXA1, API5, ARRDC3, ABCC4, BAG3, BDNF, CAPN7, CALU, CREB5, CEBPB, C1orf63, C18orf55, C20orf3, DEDD2, DDIT4, DNAJB4, DNAJC27, EGR4, ERMP1, EDN2, FBXO3, FAR1, FBN2, FOXD3, FOSL1, GBE1, GAD1, GPCPD1, GEM, HES1, HIST1H2AG, HIST1H2BD, HIST1H2BN, HDAC1, HOXB2, HTRA1, IER5, IGF2R, JMJD6, JUNB, LIPA, MXD1, MAT2A, METTL11A, MCL1, NF2, NCRNA00201, NFIL3, OPA1, KCNJ2, PPP1R10, PDK3, RCN2, RPL4, RPS27A, SIK1, SEL1L, SERTAD1, STAM, SNRPA1, SNORD14D, SNORA41, NALCN, SAT1, SPRY4, SOX9, STC1, SMARCA4, TBC1D7, TPM1, TSPYL2, VEGFA, VLDLR, WSB1, ZFP36, ZNF57, ZNF655, ZFAND2A Consistent with previous findings, the lists included a high number of genes in the p38-pathway, including CREB5, DDIT3, DUSP1, DUSP10, GADD45A, GADD45B and MYC, all up-regulated in response to HAMLET. Nine ER-stress associated genes were also found differentially expressed, including members of the heat shock protein 70 family (HSPA1A, HSPA1B, HSPA1 L, HSP1 D), other chaperones (DNAJB1, HSPA6), members of the endoplasmic-associated degradation machinery (DERL1) as well as ER-associated phosphatases (PP1R15A).

We next set out to investigate the genes specific for HAMLET and oleate, respectively. In HAMLET treated cells, predominant hits included genes involved in DNA damage and chromatin repair (OBFCA2, PARP1, PPP1CB, TP53INP1 and ZMAT3), RNA processing (PRPF3, RNGTT, PABN1 and SFRS5) and cell death (AXIN2, THBS1, TNFRSF10D and ZMAT3). The oleate specific genes (n=143) were dominated by cell death genes (API5, BAG3, HDAC1, MCL1) and transcription factors (MXD1, DEDD2, EGR4, HOXB3, NFIL2).

These results suggest that sodium oleate has a greater intrinsic effect that may be supportive of HAMLET activity whereas oleic acid is less active at the gene level. The combined gene list (Table 1) may thus define a gene signature evoked by lipid-protein complexes. This signature enables a screening of similar compounds with the goal of identification of other tumoricidal protein-lipid complexes. Additionally, in this instance, it could be beneficial from an activity viewpoint to ensure that the complex itself contains oleate in preference to oleic acid.

Example 6

α-Lactalbumin Peptides and Potassium Channel Activation

HAMLET triggers a rapid potassium flux in tumor cells. Potassium channel activity was therefore measured in A549, lung carcinoma cell lines using a indicator, which emits fluorescence signal upon entering the cells via opened potassium channels, Thallium (Tl$^+$) indicator (FIG. 18). To address if α-lactalbumin peptides alone or in combination with oleate have similar ion channel activating activity, the tumor cells were exposed to three peptides, covering the entire α-lactalbumin sequence—Alpha 1 (residue 1-40), Beta (residue 41-80), Alpha 2 (residue 81-123) (FIG. 20). Adding the peptides alone or in different mixtures with one another did not open potassium channels (FIGS. 18A and 18B).

In HAMLET, oleate contributes to the ion channel activating and the tumoricidal activities. At a concentration of 175 uM (5× the HAMLET concentration based on 4-8 oleate residues in HAMLET), potassium channels were activated by oleate alone, but at lower efficiency than HAMLET. Single peptide combinations with oleate were subsequently tested. The peptides alone or in different combinations were mixed with oleate and immediately added to the cells. Both the Alpha 1-oleate and Alpha 2-oleate mixtures activated the potassium channels more efficiently than oleate alone (FIG. 18C). Beta-oleate mixture, however, inhibited the fluxes, resulting in a lower-than-baseline fluorescence signal. An Alpha 1+Alpha 2-oleate mixture (FIG. 18D), gave a fluorescence increase comparable to HAMLET after approximately 4 minutes, but activation occurred more slowly than for the HAMLET complex. Alpha 2-Beta-oleate mixture gave a similar signal to oleate alone after approximately 3 minutes whereas Alpha 1-Beta-oleate mixture gave a slightly lower signal. The mixture that consists of all three peptides and oleate gave the lowest signal, between the baseline and Alpha 1-Beta-oleate mixture.

The results suggest that the Alpha1- and Alpha 2 peptides can present oleate to tumor cell membranes in a manner that activates ion fluxes. The beta domain did not show this capacity, however.

Example 7

α-Lactalbumin Peptides and Sodium Channel Activation

Sodium influx in Jurkat cells was measured by using CoroNa Green Sodium indicator. The fluorescence was quantified every 20-second interval for a 10-minute total measurement period. HAMLET triggered an immediate increase of fluorescence signal when added to the cells while the PBS control gave a slight decrease in fluorescence signal over time. In contrast, single peptide and mixtures of two or all three of the peptides did not trigger an increase in fluorescence (FIGS. 19A and 19B).

Oleate alone did not trigger a sodium flux, as there was no increase in the fluorescence signal (FIG. 19C). The Alpha 1-oleate and Alpha 2-oleate mixtures triggered an intermediate fluorescence increase as compared with HAMLET, and the Alpha 1-oleate mixture gave a lower fluorescence signal than the Alpha 2-oleate mixture. The Beta-oleate mixture triggered a fluorescence signal, similar to that of oleate.

Mixtures of two or more peptides with oleate are shown in FIG. 19D. The Alpha 1-Alpha 2-oleate mixture gave a slightly lower fluorescence increase than the Alpha 1-oleate mixture. Both Alpha 1-Beta-oleate and Alpha 2-Beta-oleate mixtures gave a fluorescence signal similar to that of oleate alone. The mixture that consists of all three peptides and oleate gave a signal similar to that of Alpha 1-Alpha 2-oleate mixture.

Example 8

α-Lactalbumin Peptides and Oleate Causes Cell Death

To investigate the effect of the α-lactalbumin peptide in causing tumoricidal activity, Jurkat cells were treated with peptide(s) and the extent of cell death was accessed by two cell death assays, namely ATP assay and PrestoBlue assay. Briefly, the cells were incubated with respective peptide alone or in combination with 5 times equivalent sodium oleate. The mixture of peptide and oleate was prepared as described in Example 7, and added immediately to the cells. Peptide alone did not cause a decrease in cell viability, as measured by both assays. Alpha 1-oleate and Alpha 2-oleate mixtures cause cell death, an extent similar to HAMLET, measured by both assays (FIG. 21). On the other hand, Beta-oleate caused about 50% cell death, as measured by ATP assay, but not in PrestoBlue assay.

The invention claimed is:

1. A biologically active complex comprising a peptide comprising the sequence KQFTKXELSQLLKDIDGYGGIALPELIXTMFHTSGYDTQA (SEQ ID NO: 3), wherein X is an amino acid residue other than cysteine and the peptide is up to 50 amino acids in length, and a pharmaceutically acceptable salt of a fatty acid or lipid.

2. The biologically active complex of claim 1, wherein the peptide comprises the sequence KQFTKAELSQLLKDIDGYGGIALPELIATMFHTSGYDTQA (SEQ ID NO: 5).

3. The biologically active complex of claim 1, wherein the salt of the fatty acid or lipid is a sodium or potassium salt.

4. The biologically active complex of claim 1, wherein the salt of the fatty acid or lipid is a salt of oleic acid.

5. The biologically active complex of claim 1, which further comprises a secondary reagent.

6. A pharmaceutical composition comprising the biologically active complex of claim 1 and a pharmaceutically acceptable carrier.

7. A method for preparing a biologically active complex comprising a peptide comprising SEQ ID NO: 3, wherein the peptide is up to 50 amino acids in length, and a pharmaceutically acceptable salt of a fatty acid or lipid, wherein the method comprises mixing together the peptide and the salt of a fatty acid or lipid.

8. A method for treating a cancer selected from the group consisting of skin papilloma, bladder cancer, glioblastoma, lung cancer, kidney cancer, ovarian cancer, and lymphoma, the method comprising administering to a patient in need thereof a biologically active complex comprising a peptide comprising SEQ ID NO: 3, wherein the peptide is up to 50 amino acids in length, and a fatty acid or lipid salt, or a pharmaceutical composition comprising the biologically active complex.

9. The method of claim 8, wherein the peptide comprises SEQ ID NO: 5.

10. The method of claim 8, wherein the fatty acid or lipid salt is an oleate salt.

11. A kit comprising a peptide comprising SEQ ID NO: 3, wherein the peptide is up to 50 amino acids in length, and a pharmaceutically acceptable salt of a fatty acid or lipid.

12. The kit of claim 11, wherein the peptide comprises SEQ ID NO: 5.

13. The kit of claim 11, wherein the salt of the fatty acid or lipid is a salt of oleic acid.

14. A peptide consisting of SEQ ID NO: 3.

15. The peptide of claim 14, wherein the peptide consists of SEQ ID NO:5.

* * * * *

SEQUENCE LISTING

<160> NUMBER OF SEQ ID NOS: 6

<210> SEQ ID NO 1
<211> LENGTH: 123
<212> TYPE: PRT
<213> ORGANISM: Artificial sequence
<220> FEATURE:
<223> OTHER INFORMATION: Synthesized

<400> SEQUENCE: 1

Lys Gln Phe Thr Lys Ala Glu Leu Ser Gln Leu Leu Lys Asp Ile Asp
1               5                   10                  15

Gly Tyr Gly Gly Ile Ala Leu Pro Glu Leu Ile Ala Thr Met Phe His
            20                  25                  30

Thr Ser Gly Tyr Asp Thr Gln Ala Ile Val Glu Asn Asn Glu Ser Thr
        35                  40                  45

Glu Tyr Gly Leu Phe Gln Ile Ser Asn Lys Leu Trp Ala Lys Ser Ser
    50                  55                  60

Gln Val Pro Gln Ser Arg Asn Ile Ala Asp Ile Ser Ala Asp Lys Phe
65                  70                  75                  80

Leu Asp Asp Asp Ile Thr Asp Asp Ile Met Ala Ala Lys Lys Ile Leu
                85                  90                  95

Asp Ile Lys Gly Ile Asp Tyr Trp Leu Ala His Lys Ala Leu Ala Thr
            100                 105                 110

Glu Lys Leu Glu Gln Trp Leu Ala Glu Lys Leu
        115                 120

<210> SEQ ID NO 2
<211> LENGTH: 124
<212> TYPE: PRT
<213> ORGANISM: Artificial sequence
<220> FEATURE:
<223> OTHER INFORMATION: Synthesized

<400> SEQUENCE: 2

Met Lys Gln Phe Thr Lys Ala Glu Leu Ser Gln Leu Leu Lys Asp Ile
1               5                   10                  15

Asp Gly Tyr Gly Gly Ile Ala Leu Pro Glu Leu Ile Ala Thr Met Phe
            20                  25                  30

His Thr Ser Gly Tyr Asp Thr Gln Ala Ile Val Glu Asn Asn Glu Ser
        35                  40                  45

Thr Glu Tyr Gly Leu Phe Gln Ile Ser Asn Lys Leu Trp Ala Lys Ser
    50                  55                  60

Ser Gln Val Pro Gln Ser Arg Asn Ile Ala Asp Ile Ser Ala Asp Lys
65                  70                  75                  80

Phe Leu Asp Asp Asp Ile Thr Asp Asp Ile Met Ala Ala Lys Lys Ile
                85                  90                  95

Leu Asp Ile Lys Gly Ile Asp Tyr Trp Leu Ala His Lys Ala Leu Ala
            100                 105                 110

Thr Glu Lys Leu Glu Gln Trp Leu Ala Glu Lys Leu
        115                 120

<210> SEQ ID NO 3
<211> LENGTH: 40
<212> TYPE: PRT
<213> ORGANISM: Artificial sequence
<220> FEATURE:
<223> OTHER INFORMATION: Synthesized
<220> FEATURE:
<221> NAME/KEY: VARIANT
<222> LOCATION: (6)..(6)
<223> OTHER INFORMATION: Xaa is an amino acid residue other than
      cysteine
<220> FEATURE:
<221> NAME/KEY: VARIANT
<222> LOCATION: (28)..(28)
<223> OTHER INFORMATION: Xaa is an amino acid residue other than
      cysteine

<400> SEQUENCE: 3

Lys Gln Phe Thr Lys Xaa Glu Leu Ser Gln Leu Leu Lys Asp Ile Asp
1               5                   10                  15

Gly Tyr Gly Gly Ile Ala Leu Pro Glu Leu Ile Xaa Thr Met Phe His
            20                  25                  30

Thr Ser Gly Tyr Asp Thr Gln Ala
        35                  40

<210> SEQ ID NO 4
<211> LENGTH: 43
<212> TYPE: PRT
<213> ORGANISM: Artificial sequence
<220> FEATURE:
<223> OTHER INFORMATION: Synthesized
<220> FEATURE:
<221> NAME/KEY: VARIANT
<222> LOCATION: (11)..(11)
<223> OTHER INFORMATION: Xaa is an amino acid residue other than
      cysteine
<220> FEATURE:
<221> NAME/KEY: VARIANT
<222> LOCATION: (31)..(31)
<223> OTHER INFORMATION: Xaa is an amino acid residue other than
      cysteine
<220> FEATURE:
<221> NAME/KEY: VARIANT
<222> LOCATION: (40)..(40)
<223> OTHER INFORMATION: Xaa is an amino acid residue other than
      cysteine

<400> SEQUENCE: 4

Leu Asp Asp Asp Ile Thr Asp Asp Ile Met Xaa Ala Lys Lys Ile Leu
1               5                   10                  15

Asp Ile Lys Gly Ile Asp Tyr Trp Leu Ala His Lys Ala Leu Xaa Thr
            20                  25                  30

Glu Lys Leu Glu Gln Trp Leu Xaa Glu Lys Leu
        35                  40

<210> SEQ ID NO 5
<211> LENGTH: 40
<212> TYPE: PRT
<213> ORGANISM: Artificial sequence
<220> FEATURE:
<223> OTHER INFORMATION: Synthesized

<400> SEQUENCE: 5

Lys Gln Phe Thr Lys Ala Glu Leu Ser Gln Leu Leu Lys Asp Ile Asp
1               5                   10                  15

Gly Tyr Gly Gly Ile Ala Leu Pro Glu Leu Ile Ala Thr Met Phe His
            20                  25                  30

Thr Ser Gly Tyr Asp Thr Gln Ala
        35                  40

<210> SEQ ID NO 6
<211> LENGTH: 43
<212> TYPE: PRT
<213> ORGANISM: Artificial sequence
<220> FEATURE:

```
<223> OTHER INFORMATION: Synthesized

<400> SEQUENCE: 6

Leu Asp Asp Asp Ile Thr Asp Asp Ile Met Ala Ala Lys Lys Ile Leu
1               5                   10                  15

Asp Ile Lys Gly Ile Asp Tyr Trp Leu Ala His Lys Ala Leu Ala Thr
            20                  25                  30

Glu Lys Leu Glu Gln Trp Leu Ala Glu Lys Leu
        35                  40
```